Figure 4A:
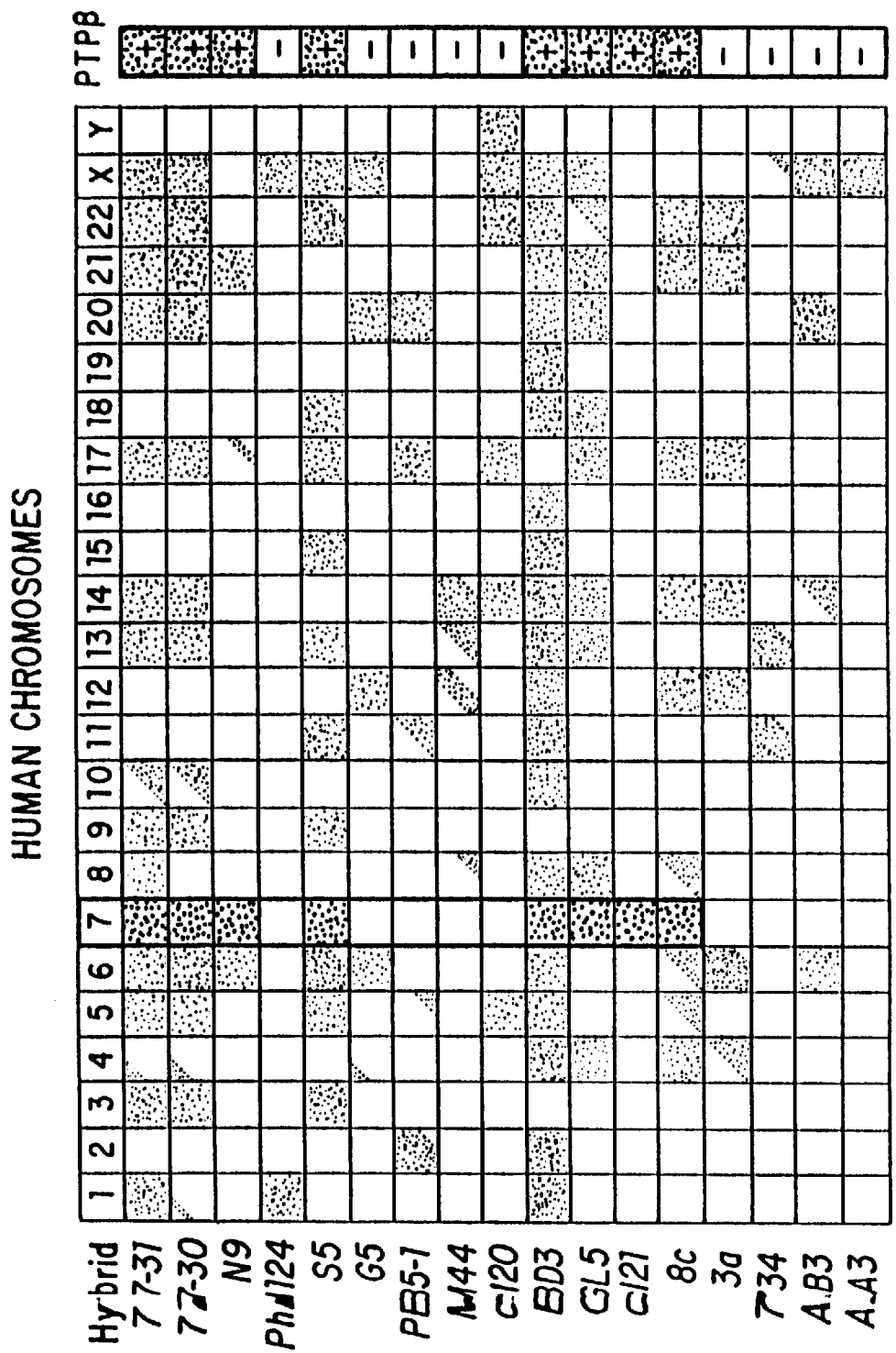

United States Patent [19]
Schlessinger

[11] Patent Number: 5,925,536
[45] Date of Patent: Jul. 20, 1999

[54] RECEPTOR-TYPE PHOSPHOTYROSINE PHOSPHATASE-β

[75] Inventor: Joseph Schlessinger, New York, N.Y.

[73] Assignee: New York University, New York, N.Y.

[21] Appl. No.: 08/448,164

[22] Filed: May 24, 1995

Related U.S. Application Data

[60] Division of application No. 08/015,973, Feb. 10, 1993, Pat. No. 5,604,094, which is a continuation-in-part of application No. 07/654,188, Feb. 26, 1991, abandoned, which is a continuation-in-part of application No. 07/551,270, Jul. 11, 1990, abandoned.

[51] Int. Cl.$^6$ ............................... C12Q 1/42; C12N 9/16; C12N 15/55
[52] U.S. Cl. ........................... 435/21; 435/196; 536/23.2
[58] Field of Search ..................... 435/21, 196; 536/23.2

[56] References Cited

FOREIGN PATENT DOCUMENTS

PCT WO92/01050  1/1992  WIPO.

OTHER PUBLICATIONS

Kaplan et al., Cloning of three human tyrosine phosphatases reveals a multigene family of receptor–linked protein–tyrosine–phosphatases expressed in brain, Proc. Natl. Acad. Sci. USA 87: 7000–7004 (1990).
Sap et al., Cloning and expression of a widely expressed receptor tyrosine phosphatase, Proc. Natl. Acad. Sci. USA 87: 6112–6116 (1990).
Daum et al., Characterization of a human recombinant receptor–linked protein tyrosine phosphatase, J. Biol. Chem., 266: 12211–12215 (1991).
Gebbink et al., Cloning, expression and chromosomal localization of a new putative receptor–like protein tyrosine phosphatase, FEBS Lett. 290: 123–130 (1991).
Tsai et al., Isolation and characterization of temperature–sensitive and thermostable mutants of the human receptor–like protein tyrosine phosphatase LAR, J. Biol. Chem. 266(16): 10534–10543 (1991).
George and Parker, Preliminary characterization of phosphotyrosine phosphatase activities in human peripheral blood lymphocytes: Identification of CD45 as a phosphotyrosine phosphatase, J. Cell Biochem. 42: 71–81 (1990).
Jirik et al., Cloning of a novel receptor–linked protein tyrosine phosphatase from a human hepatoblastoma cell line, FASEB J. 4A: 2082 (Abstr. 2253) (1990).
Jirik et al., Cloning and chromosomal asignment of a widely expressed human receptor–like protein–tyrosine phosphatase, FEBS Lett. 273: 239–242 (1990).
Krueger et al., Structural diversity and evolution of human receptor–like protein tyrosine phosphatases, EMBO J. 9: 3241–3252 (1990).
Matthews et al., Identification of an additional member of the protein–tyrosine–phosphatase family: Evidence for alternative splicing in the tyrosine phosphatase domain, Proc. Natl. Acad. Sci. USA 87: 4444–4448 (1990).

Ohagi et al., Sequence of a cDNA encoding human LRP (leukocyte common antigen–related peptide), Nucl. Acids Res. 18: 7159 (1990).
Streuli et al., Distinct functional roles of two intracellular phosphatase like domains of the receptor–linked protein tyrosine phosphatases LCA and LAR, EMBO Journal 9: 2399–2407 (1990).
Kiener and Mittler, CD45–protein tyrosine phosphatase cross–linking inhibits T–cell receptor CD3–mediated activation in human T–cells, J. Immunol. 143: 23–28 (1989).
Mustelin et al., Rapid activation of the T–cell tyrosine protein kinase pp56lck by the CD45 phosphotyrosine phosphatase, Proc. Natl. Acad. Sci. USA 86: 6302–6306 (1989).
Ostergaard et al., Expression of CD45 alters phosphorylation of the lck–encoded tyrosine protein kinase in murine lymphoma T–cell lines, Proc. Natl. Acad. Sci. USA 86: 8959–8963 (1989).
Hall et al., Complete exon–intron organization of the human leukocyte common antigen (CD45) gene, J. Immunol. 141: 2781–2787 (1988).
Streuli et al., A new member of the immunoglobulin superfamily that has a cytoplasmic region homologous to the leukocyte common antigen, J. Exp. Med. 168: 1523–1530 (1988).
Charbonneau et al., The leukocyte common antigen (CD45): A putative receptor–linked protein tyrosine phosphatase, Proc. Natl. Acad. Sci. USA 85: 7182–7186 (1988).
Ralph et al., Structural variants of human T200 glycoprotein (leukocyte–common antigen), EMBO J. 6: 1251–1257 (1987).
Streuli et al., Differential usage of three exons generates at least five different mRNAs encoding human leukocyte common antigens, J. Exp. Med. 166: 1548–1566 (1987).
Hariharan et al., Cloning and characterization of a receptor–class phosphotyrosine phosphatase gene expressed on central nervous system axons in *Drosophila melanogaster*, Proc. Natl. Acad. Sci. USA 88: 11266–11270 (1991).
Streuli et al., A family of receptor–linked protein tyrosine phosphatases in humans and Drosophila, Proc. Natl. Acad. Sci. USA 86: 8698–8702 (1989).
Gu et al., Identification, cloning, and expression of a cytosolic megakaryocyte protein–tyrosine–phophatase with sequence homology to cytoskeletal protein 4.1, Proc. Natl. Acad. Sci. USA 88: 5867–5871 (1991).
Lombroso et al., Molecular characterization of a protein–tyrosine–phophatase enriched in striatum, Proc. Natl. Acad. Sci. USA 88: 7242–7246 (1991).

(List continued on next page.)

*Primary Examiner*—Rebecca E. Prouty
*Attorney, Agent, or Firm*—Pennie & Edmonds LLP

[57] ABSTRACT

A novel receptor-type protein tyrosine phosphatase-β (RPTPβ) protein or glycoprotein, and the DNA coding therefor is disclosed. This protein is naturally expressed in the brain and in neural cell lines. The RPTPβ protein or glycoprotein may be produced by recombinant means. Antibodies to the protein, methods for measuring the quantity of the protein, methods for screening compounds, such as drugs, which can bind to the protein and inhibit or stimulate it phosphatase enzymatic activity, are provided.

10 Claims, 26 Drawing Sheets

OTHER PUBLICATIONS

Yang and Tonks, Isolation of a cDNA clone encoding a human protein–tyrosine phosphatse with homology to the cytoskeletal–associated proteins band 4.1, ezrin, and talin, Proc. Natl. Acad. Sci. USA 88: 5949–5953 (1991).

Chernon et al., Cloning of a cDNA for a major human protein–tyrosine–phosphatase, Proc. Natl. Acad. Sci. USA, 87: 2735–2739 (1990).

Cool et al., Overexpression of a T–cell protein tyrosine phosphatase (PTPase) in BHK Cells, FASEB J. 4: A2078 (abstr. 2230) (1990).

Guan et al., Cloning and expression of a protein–tyrosine–phosphatase, Proc. Natl. Acad. Sci. USA 87: 1501–1505 (1990).

Thomas et al., ABA, A novel member of the tyrosine phosphatase family, FASEB J. 4: A2078 (Abstr. 3140) (1990).

Tonks et al., CD45, an integral membrane protein tyrosine phosphatase, J. Biol. Chem. 265: 10674–10680 (1990).

Charbonneau et al., Human placenta protein–tyrosine–phosphatase: Amino acid sequence and relationship to a family of receptor–like proteins, Proc. Natl. Acad. Sci. USA 86: 5252–5256 (1989).

Cool et al., cDNA isolated from human T–cell library encodes a member of the protein–tyrosine–phosphatase family, Proc. Natl. Acad. Sci. USA 86: 5257–5261 (1989).

Tonks et al., Purification of the major protein–tyrosine–phosphatases of human placenta, J. Biol. Chem. 263: 6722–6730 (1988).

Tonks et al., Demonstration that the leukocyte common antigen CD45 is a protein tyrosine phosphatase, Biochemistry 27: 8695–8701 (1988).

Matthews et al., Characterization of hematopoietic intracelluar protein tyrosine phosphatases: Description of a phosphatase containing an SH2 Domain and another enriched in proline–, glutamic acid–, serine–, and threonine–rich sequences, Molec. and Cell. Biol. 12: 2396–2405 (1992).

Plutzky et al., Isolation of a src homology 2–containing tyrosine phosphatase, Proc. Natl. Acad, Sci. USA 89: 1123–1127 (1992).

Yi et al., Protein tyrosine phosphatase containing SH2 domains: characterization, preferential expression in hematopoietic cells, and localization to human chromosome 12p12–p13, Mol. and Cell. Biol. 12: 836–846 (1992).

Shen et al., A protein–tyrosine phosphatase with sequence similarity to the SH2 domain of the protein–tyrosine kinases, Nature 352: 736–739 (1991).

Klarlund, Transformation of cells by an inhibitor of phosphatases acting on phosphotyrosine in proteins, Cell 41: 707–717 (1985).

Pallen et al., Purification of a phosphotyrosine phosphatase that dephosphorylates the epidermal growth factor receptor autophosphorylation sites, Ann. N.Y. Acad. Sci. 551: 299–308 (1988).

Butler et al., Characterization of a membrane–associated phosphotyrosyl protein phosphatase from the A431 human epidermoid carcinoma cell line, Eur. J. Biochem. 185: 475–483 (1989).

Cyert and Thorner, Putting it on and taking it off: Phosphoprotein phosphatase involvement in cell cycle regulation, Cell 57: 891–893 (1989).

Jones et al., Phosphotyrosyl–protein phosphatases, J. Biol. Chem. 264: 7747–7753 (1989).

Pingel and Thomas, Evidence that the leukocyte–common antigen is required for antigen–induced T lymphocyte proliferation, Cell 58: 1055–1065 (1989).

Pot and Dixon, A thousand and two protein tyrosine phosphatases, Biochem. Biophys. Acta. 1136: 35–43 (1992).

Fischer et al., Protein tyrosine phosphatases: A diverse family of intracellular and transmembrane enzymes, Science 253: 401–406 (1991).

Hunter, Protein–tyrosine phosphatases: the other side of the coin, Cell 58: 1013–1016 (1989).

Thomas, The leukocyte common antigen family, Ann. Rev. Immunol. 7: 339–369 (1989).

Tonks and Charbonneau, Protein tyrosine dephosphorylation and signal transduction, Trends in Biochem. Sci. 14: 497–500 (1989).

Neil X. Krueger and Haruo Saito, A Human Transmembrane Protein–Tyrosine–Phosphatase, PTPS, is Expressed in Brain and Has an N–Terminal Receptor Domain Homologous to Carbonic Anhydrases; Proc. Natl. Acad. Sci. USA, 89: 7417–7421 (1992).

Guan et al., Protein Tyrosine Phosphatase Activity of an Essential Virulence Determinant in Yersinia Science, 249: 553–556 (1990).

Berger et al., Guide to Molecular Cloning Techniques, Meth. Enzymol., 152: 393–399, 415–423, 432–447, 661–703 (1987).

```
          1  ATGCGAATCCTAAAGCGTTTCCTCGCTTGCATTCAGCTCCTCTGTGTTTGCCGCCTGGAT  60
SIGNAL    1 [M  R  I  L  K  R  F  L  A  C  I  Q  L  L  C  V  C  R  L  D   20
PEPTIDE

61  TGGGCTAATGGATACTACAGACAACAGAGAAAACTTGTTGAAGAGATTGGCTGGTCCTAT 120
         21  W  A  N  G] Y  Y  R  Q  Q  R  K  L [V  E  E  I  G  W  S  Y   40

CAH-LIKE
        121  ACAGGAGCACTGAATCAAAAAAATTGGGGAAAGAAATATCCAACATGTAATAGCCCAAAA 180
         41  T  G  A  L  N  Q  K  N  W  G  K  K  Y  P  T  C  N  S  P  K   60

181  CAATCTCCTATCAATATTGATGAAGATCTTACACAAGTAAATGTGAATCTTAAGAAACTT 240
         61  Q  S  P  I  N  I  D  E  D  L  T  Q  V  N  V  N  L  K  K  L   80

241  AAATTTCAGGGTTGGGATAAAACATCATTGGAAAACACATTCATTCATAACACTGGGAAA 300
         81  K  F  Q  G  W  D  K  T  S  L  E  N  T  F  I  H  N  T  G  K  100

301  ACAGTGGAAATTAATCTCACTAATGACTACCGTGTCAGCGGAGGAGTTTCAGAAATGGTG 360
        101  T  V  E  I  N  L  T  N  D  Y  R  V  S  G  G  V  S  E  M  V  120

361  TTTAAAGCAAGCAAGATAACTTTTCACTGGGGAAAATGCAATATGTCATCTGATGGATCA 420
        121  F  K  A  S  K  I  T  F  H  W  G  K  C  N  M  S  S  D  G  S  140

421  GAGCACAGTTTAGAAGGACAAAAATTTCCACTTGAGATGCAAATCTACTGCTTTGATGCA 480
        141  E  H  S  L  E  G  Q  K  F  P  L  E  M  Q  I  Y  C  F  D  A  160

481  GACCGATTTTCAAGTTTTGAGGAAGCAGTCAAAGGAAAAGGGAAGTTAAGAGCTTTATCC 540
        161  D  R  F  S  S  F  E  E  A  V  K  G  K  G  K  L  R  A  L  S  180

541  ATTTTGTTTGAGGTTGGGACAGAAGAAAATTTGGATTTCAAAGCGATTATTGATGGAGTC 600
        181  I  L  F  E  V  G  T  E  E  N  L  D  F  K  A  I  I  D  G  V  200
```

FIG.1A

```
601  GAAAGTGTTAGTCGTTTTGGGAAGCAGGCTGCTTTAGATCCATTCATACTGTTGAACCTT  660
201   E  S  V  S  R  F  G  K  Q  A  A  L  D  P  F  I  L  L  N  L   220

661  CTGCCAAACTCAACTGACAAGTATTACATTTACAATGGCTCATTGACATCTCCTCCCTGC  720
221   L  P  N  S  T  D  K  Y  Y  I  Y  N  G  S  L  T  S  P  P  C   240

721  ACAGACACAGTTGACTGGATTGTTTTTAAAGATACAGTTAGCATCTCTGAAAGCCAGTTG  780
241   T  D  T  V  D  W  I  V  F  K  D  T  V  S  I  S  E  S  Q  L   260

781  GCTGTTTTTTGTGAAGTTCTTACAATGCAACAATCTGGTTATGTCATGCTGATGGACTAC  840
261   A  V  F  C  E  V  L  T  M  Q  Q  S  G  Y  V  M  L  M  D  Y   280

841  TTACAAAACAATTTTCGAGAGCAACAGTACAAGTTCTCTAGACAGGTGTTTTCCTCATAC  900
281   L  Q  N  N  F  R  E  Q  Q  Y  K  F  S  R  Q  V  F  S  S  Y   300

901  ACTGGAAAGGAAGAGATTCATGAAGCAGTTTGTAGTTCAGAACCAGAAAATGTTCAGGCT  960
301   T  G  K  E  E  I  H  E  A  V  C  S  S  E  P  E  N  V  Q  A   320

961  GACCCAGAGAATTATACCAGCCTTCTTGTTACATGGGAAAGACCTCGAGTCGTTTATGAT  1020
321   D  P  E  N  Y  T  S  L  L  V  T  W  E  R  P  R  V  V  Y  D   340

1021 ACCATGATTGAGAAGTTTGCAGTTTTGTACCAGCAGTTGGATGGAGAGGACCAAACCAAG  1080
341   T  M  I  E  K  F  A  V  L  Y  Q  Q  L  D  G  E  D  Q  T  K   360

1081 CATGAATTTTTGACAGATGGCTATCAAGACTTGGGTGCTATTCTCAATAATTTGCTACCC  1140
361   H  E  F  L  T  D  G  Y  Q  D  L  G  A  I  L  N  N  L  L  P   380

1141 AATATGAGTTATGTTCTTCAGATAGTAGCCATATGCACTAATGGCTTATATGGAAAATAC  1200
381   N  M  S  Y  V  L  Q  I  V  A  I  C  T  N  G  L  Y  G  K  Y   400
```

FIG.1B

```
1201  AGCGACCAACTGATTGTCGACATGCCTACTGATAATCCTGAACTTGATCTTTTCCCTGAA  1260
401    S  D  Q  L  I  V  D  M  P  T  D  N  P  E  L  D  L  F  P  E   420

1261  TTAATTGGAACTGAAGAAATAATCAAGGAGGAGGAAGAGGGAAAAGACATTGAAGAAGGC  1320
421    L  I  G  T  E  E  I  I  K  E  E  E  E  G  K  D  I  E  E  G   440

1321  GCTATTGTGAATCCTGGTAGAGACAGTGCTACAAACCAAATCAGGAAAAAGGAACCCCAG  1380
441    A  I  V  N  P  G  R  D  S  A  T  N  Q  I  R  K  K  E  P  Q   460

1381  ATTTCTACCACAACACACTACAATCGCATAGGGACGAAATACAATGAAGCCAAGACTAAC  1440
461    I  S  T  T  H  Y  N  R  I  G  T  K  Y  N  E  A  K  T  N     480

1441  CGATCCCCAACAAGAGGAAGTGAATTCTCTGGAAAGGGTGATGTTCCCAATACATCTTTA  1500
481    R  S  P  T  R  G  S  E  F  S  G  K  G  D  V  P  N  T  S  L   500

1501  AATTCCACTTCCCAACCAGTCACTAAAATTAGCCACAGAAAAAGATATTTCCTTGACTTCT  1560
501    N  S  T  S  Q  P  V  T  K  L  A  T  E  K  D  I  S  L  T  S   520

1561  CAGACTGTGACTGAACTGCCACCTCACACTGTGGAAGGTACTTCAGCCTCTTTAAATGAT  1620
521    Q  T  V  T  E  L  P  P  H  T  V  E  G  T  S  A  S  L  N  D   540

1621  GGCTCTAAAACTGTTCTTAGATCTCCACATATGAACTTGTCGGGGACTGCAGAATCCTTA  1680
541    G  S  K  T  V  L  R  S  P  H  M  N  L  S  G  T  A  E  S  L   560

1681  AATACAGTTTCTATAACAGAATATGAGGAGGAGAGTTTATTGACCAGTTTCAAGCTTGAT  1740
561    N  T  V  S  I  T  E  Y  E  E  E  S  L  L  T  S  F  K  L  D

1741  ACTGGAGCTGAAGATTCTTCAGGCTCCAGTCCCGCAACTTCTGCTATCCCATTCATCTCT  1800
581    T  G  A  E  D  S  S  G  S  S  P  A  T  S  A  I  P  F  I  S   600
```

FIG.1C

1801 GAGAACATATCCCAAGGGTATATATTTTCCTCCGAAAACCCAGAGACAATAACATATGAT 1860
601  E   N   I   S   Q   G   Y   I   F   S   S   E   N   P   E   T   I   T   Y   D  620

1861 GTCCTTATACCAGAATCTGCTAGAAATGCTTCCGAAGATTCAACTTCATCAGGTTCAGAA 1920
621  V   L   I   P   E   S   A   R   N   A   S   E   D   S   T   S   S   G   S   E  640

1921 GAATCACTAAAGGATCCTTCTATGGAGGGAAATGTGTGGTTTCCTAGCTCTACAGACATA 1980
641  E   S   L   K   D   P   S   M   E   G   N   V   W   F   P   S   S   T   D   I  660

1981 ACAGCACAGCCCGATGTTGGATCAGGCAGAGAGAGCTTTCTCCAGACTAATTACACTGAG 2040
661  T   A   Q   P   D   V   G   S   G   R   E   S   F   L   Q   T   N   Y   T   E  680

2041 ATACGTGTTGATGAATCTGAGAAGACAACCAAGTCCTTTTCTGCAGGCCCAGTGATGTCA 2100
681  I   R   V   D   E   S   E   K   T   T   K   S   F   S   A   G   P   V   M   S  700

2101 CAGGGTCCCTCAGTTACAGATCTGGAAATGCCACATTATTCTACCTTTGCCTACTTCCCA 2160
701  Q   G   P   S   V   T   D   L   E   M   P   H   Y   S   T   F   A   Y   F   P  720

2161 ACTGAGgTAACACCTCATGCTTTTACCCCATCCTCCAGACAACAGGATTTGGTCTCCACG 2220
721  T   E   V   T   P   H   A   F   T   P   S   S   R   Q   Q   D   L   V   S   T  740

2221 GTCAACGTGGTATACTCGCAGACAACCCAACCGGTATACAATGGTGAGACACCTCTTCAA 2280
741  V   N   V   V   Y   S   Q   T   T   Q   P   V   Y   N   G   E   T   P   L   Q  760

2281 CCTTCCTACAGTAGTGAAGTCTTTCCTCTAGTCACCCCTTTGTTGCTTGACAATCAGATC 2340
761  P   S   Y   S   S   E   V   F   P   L   V   T   P   L   L   L   D   N   Q   I  780

2341 CTCAACACTACCCCTGCTGCTTCAAGTAGTGATTCGGCCTTGCATGCTACGCCTGTATTT 2400
781  L   N   T   T   P   A   A   S   S   S   D   S   A   L   H   A   T   P   V   F  800

FIG. 1D

```
2401 CCCAGTGTCGATGTGTCATTTGAATCCATCCTGTCTTCCTATGATGGTGCACCTTTGCTT 2460
 801  P  S  V  D  V  S  F  E  S  I  L  S  S  Y  D  G  A  P  L  L  820

2461 CCATTTTCCTCTGCTTCCTTCAGTAGTGAATTGTTTCGCCATCTGCATACAGTTTCTCAA 2520
 821  P  F  S  S  A  S  F  S  S  E  L  F  R  H  L  H  T  V  S  Q  840

2521 ATCCTTCCACAAGTTACTTCAGCTACCGAGAGTGATAAGGTGCCCTTGCATGCTTCTCTG 2580
 841  I  L  P  Q  V  T  S  A  T  E  S  D  K  V  P  L  H  A  S  L  860

2581 CCAGTGGCTGGGGGTGATTTGCTATTAGAGCCCAGCCTTGCTCAGTATTCTGATGTGCTG 2640
 861  P  V  A  G  G  D  L  L  L  E  P  S  L  A  Q  Y  S  D  V  L  880

2641 TCCACTACTCATGCTGCTTCAAAGACGCTGGAATTTGGTAGTGAATCTGGTGTTCTTTAT 2700
 881  S  T  T  H  A  A  S  K  T  L  E  F  G  S  E  S  G  V  L  Y  900

2701 AAAACGCTTATGTTTTCTCAAGTTGAACCACCCAGCAGTGATGCCATGATGCATGCACGT 2760
 901  K  T  L  M  F  S  Q  V  E  P  P  S  S  D  A  M  M  H  A  R  920

2761 TCTTCAGGGCCTGAACCTTCTTATGCCTTGTCTGATAATGAGGGCTCCCAACACATCTTC 2820
 921  S  S  G  P  E  P  S  Y  A  L  S  D  N  E  G  S  Q  H  I  F  940

2821 ACTGTTTCTTACAGTTCTGCAATACCTGTGCATGATTCTGTGGGTGTAACTTATCAGGGT 2880
 941  T  V  S  Y  S  S  A  I  P  V  H  D  S  V  G  V  T  Y  Q  G  960

2881 TCCTTATTTAGCGGCCCTAGCCATATACCAATACCTAAGTCTTCGTTAATAACCCCAACT 2940
 961  S  L  F  S  G  P  S  H  I  P  I  P  K  S  S  L  I  T  P  T  980
```

FIG.1E

```
2941  GCATCATTACTGCAGCCTACTCATGCCCTCTCTGGTGATGGGGAATGGTCTGGAGCCTCT  3000
 981   A  S  L  L  Q  P  T  H  A  L  S  G  D  G  E  W  S  G  A  S   1000

3001  TCTGATAGTGAATTTCTTTTACCTGACACAGATGGGCTGACAGCCCTTAACATTTCTTCA  3060
1001   S  D  S  E  F  L  L  P  D  T  D  G  L  T  A  L  N  I  S  S   1020

3061  CCTGTTTCTGTAGCTGAATTTACATATACAACATCTGTGTTTGGTGATGATAATAAGGCG  3120
1021   P  V  S  V  A  E  F  T  Y  T  T  S  V  F  G  D  D  N  K  A   1040

3121  CTTTCTAAAAGTGAAATAATATATGGAAATGAGACTGAACTGCAAATTCCTTCTTTCAAT  3180
1041   L  S  K  S  E  I  I  Y  G  N  E  T  E  L  Q  I  P  S  F  N   1060

3181  GAGATGGTTTAcCCTTCTGAAAGCACAGTCATGCCCAACATGTATGATAATGTAAATAAG  3240
1061   E  M  V  Y  P  S  E  S  T  V  M  P  N  M  Y  D  N  V  N  K   1080

3241  TTGAATGCGTCTTTACAAGAAACCTCTGTTTCCATTTCTAGCACCAAGGGCATGTTTCCA  3300
1081   L  N  A  S  L  Q  E  T  S  V  S  I  S  S  T  K  G  M  F  P   1100

3301  GGGTCCCTTGCTCATACCACCACTAAGGTTTTTGATCATGAGATTAGTCAAGTTCCAGAA  3360
1101   G  S  L  A  H  T  T  T  K  V  F  D  H  E  I  S  Q  V  P  E   1120

3361  AATAACTTTTCAGTTCAACCTACACATACTGTCTCTCAAGCATCTGGTGACACTTCGCTT  3420
1121   N  N  F  S  V  Q  P  T  H  T  V  S  Q  A  S  G  D  T  S  L   1140

3421  AAACCTGTGCTTAGTGCAAACTCAGAGCCAGCATCCTCTGACCCTGCTTCTAGTGAAATG  3480
1141   K  P  V  L  S  A  N  S  E  P  A  S  S  D  P  A  S  S  E  M   1160

3481  TTATCTCCTTCAACTCAGCTCTTATTTTATGAGACCTCAGCTTCTTTTAGTACTGAAGTA  3540
1161   L  S  P  S  T  Q  L  L  F  Y  E  T  S  A  S  F  S  T  E  V   1180
```

FIG.1F

```
3541  TTGCTACAACCTTCCTTtCAGGCTTCTGATGTTGACACCTTGCTTAAAACTGTTCTTCCA  3600
1181   L  L  Q  P  S  F  Q  A  S  D  V  D  T  L  L  K  T  V  L  P   1200

3601  GCTGTGCCCAGTGATCCAATATTGGTTGAAACCCCCAAAGTTGATAAAATTAGTTCTACA  3660
1201   A  V  P  S  D  P  I  L  V  E  T  P  K  V  D  K  I  S  S  T   1220

3661  ATGTTGCATCTCATTGTATCAAATTCTGCTTCAAGTGAAAACATGCTGCACTCTACATCT  3720
1221   M  L  H  L  I  V  S  N  S  A  S  S  E  N  M  L  H  S  T  S   1240

3721  GTACCAGTTTTTGATGTGTCGCCTACTTCTcATATGCACTCTGCTTCACTTCAAGGTTTG  3780
1241   V  P  V  F  D  V  S  P  T  S  H  M  H  S  A  S  L  Q  G  L   1260

3781  ACCATTTCCTATGCAAGTGAGAAATATGAACCAGTTTTGTTAAAAAGTGAAAGTTCCCAC  3840
1261   T  I  S  Y  A  S  E  K  Y  E  P  V  L  L  K  S  E  S  S  H   1280

3841  CAAGTGGTACCTTCTTTGTACAGTAATGATGAGTTGTTCCAAACGGCCAATTTGGAGATT  3900
1281   Q  V  V  P  S  L  Y  S  N  D  E  L  F  Q  T  A  N  L  E  I   1300

3901  AACCAGGCCCATCCCCCAAAAGGAAGGCATGTATTTGCTACACCTGTTTTATCAATTGAT  3960
1301   N  Q  A  H  P  P  K  G  R  H  V  F  A  T  P  V  L  S  I  D   1320

3961  GAACCATTAAATACACTAATAAATAAGcTtATACATTCCGATGAAATTTTAACCTCCACC  4020
1321   E  P  L  N  T  L  I  N  K  L  I  H  S  D  E  I  L  T  S  T   1340

4021  AAAaGTTCTGTTACTGGTAAGGTATTTGCTGGTATTCCAACAGTTGCTTCTGATACATTT  4080
1341   K  S  S  V  T  G  K  V  F  A  G  I  P  T  V  A  S  D  T  F   1360

4081  GTATCTACTGATCATTCTGTTCCTATAGGAAATGGgCATGTTGCCaTTACAGCTGTTTCT  4140
1361   V  S  T  D  H  S  V  P  I  G  N  G  H  V  A  I  T  A  V  S   1380
```

FIG.1G

```
4141  CCCCACAGAGATGGTTCTGTAACCTCAACAAAGTTGCTGTTTCCTTCTAAGGCAACTTCT  4200
1381   P  H  R  D  G  S  V  T  S  T  K  L  L  F  P  S  K  A  T  S   1400

4201  GAGCTGAGTCATAGTGCCAAATCTGATGCCGGTTTAGTGGGTGGTGGTGAAGATGGTGAC  4260
1401   E  L  S  H  S  A  K  S  D  A  G  L  V  G  G  G  E  D  G  D   1420

4261  ACTGATGATGATGGTGATGATGATGATGATGACAGAGGTAGTGATGGCTTATCCATTCAT  4320
1421   T  D  D  D  G  D  D  D  D  D  D  R  G  S  D  G  L  S  I  H   1440

4321  AAGTGTATGTCATGCTCATCCTATAGAGAATCACAGGAAAAGGTAATGAATGATTCAGAC  4380
1441   K  C  M  S  C  S  S  Y  R  E  S  Q  E  K  V  M  N  D  S  D   1460

4381  ACCCACGAAAACAGTCTTATGGATCAGAATAATCCAATCTCATACTCACTATCTGAGAAT  4440
       T  H  E  N  S  L  M  D  Q  N  N  P  I  S  Y  S  L  S  E  N   1480

4441  TCTGAAGAAGATAATAGAGTCACAAGTGTATCCTCAGACAGTCAAACTGGTATGGACAGA  4500
1481   S  E  E  D  N  R  V  T  S  V  S  S  D  S  Q  T  G  M  D  R   1500

4501  AGTCCTGGTAAATCACCATCAGCAAATGGGCTATCCCAAAAGCACAATGATGGAAAAGAG  4560
1501   S  P  G  K  S  P  S  A  N  G  L  S  Q  K  H  N  D  G  K  E   1520

4561  GAAAATGACATTCAGACTGGTAGTGCTCTGCTTCCTCTCAGCCCTGAATCTAAAGCATGG  4620
1521   E  N  D  I  Q  T  G  S  A  L  L  P  L  S  P  E  S  K  A  W   1540

4621  GCAGTTCTGACAAGTGATGAAGAAAGTGGATCAGGGCAAGGTACCTCAGATAGCCTTAAT  4680
1541   A  V  L  T  S  D  E  E  S  G  S  G  Q  G  T  S  D  S  L  N   1560

4681  GAGAATGAGACTTCCACAGATTTCAGTTTTGCAGACACTAATGAAAAAGATGCTGATGGG  4740
1561   E  N  E  T  S  T  D  F  S  F  A  D  T  N  E  K  D  A  D  G   1580
```

FIG.1H

```
            4741  ATCCTGGCAGCAGGTGACTCAGAAATAACTCCTGGATTCCCACAGTCCCCAACATCATCT  4800
            1581   I   L   A   A   G   D   S   E   I   T   P   G   F   P   Q   S   P   T   S   S   1600

4801  GTTACTAGCGAGAACTCAGAAGTGTTCCACGTTTCAGAGGCAGAGGCCAGTAATAGTAGC  4860
            1601   V   T   S   E   N   S   E   V   F   H   V   S   E   A   E   A   S   N   S   S   1620

4861  CATGAGTCTCGTATTGGTCTAGCTGAGGGGTTGGAATCCGAGAAGAAGGCAGTTATACCC  4920
            1621   H   E   S   R   I   G   L   A   E   G   L   E   S   E   K   K  [A   V   I   P   1640
TRANS-
MEMBRANE
            4921  CTTGTGATCGTGTCAGCCCTGACTTTTATCTGTCTAGTGGTTCTTGTGGGTATTCTCATC  4980
            1641   L   V   I   V   S   A   L   T   F   I   C   L   V   V   L   V   G   I   L   I   1660

4981  TACTGGAGGAAATGCTTCCAGACTGCACACTTTTACTTAGAGGACAGTACATCCCCTAGA  5040
            1661   Y   W]  R   K   C   F   Q   T   A   H   F   Y   L   E   D   S   T   S   P   R   1680

5041  GTTATATCCACACCTCCAACACCTATCTTTCCAATTTCAGATGATGTCGGAGCAATTCCA  5100
            1681   V   I   S   T   P   P   T   P   I   F   P   I   S   D   D   V   G   A   I   P   1700

5101  ATAAAGCACTTTCCAAAGCATGTTGCAGATTTACATGCAAGTAGTGGGTTTACTGAAGAA  5160
            1701   I   K   H   F   P   K   H   V   A   D   L   H   A   S   S   G   F   T   E   E   1720

5161  TTTGAGGAAGTGCAGAGCTGTACTGTTGACTTAGGTATTACAGCAGACAGCTCCAACCAC  5220
            1721   F   E   E   V   Q   S   C   T   V   D   L   G   I   T   A   D   S   S   N   H   1740

5221  CCAGACAACAAGCACAAGAATCGATACATAAATATCGTTGCCTATGATCATAGCAGGGTT  5280
            1741   P   D  [N   K   H   K   N   R   Y   I   N   I   V   A   Y   D   H   S   R   V   1760
PTPASE
DOMAIN I
            5281  AAGCTAGCACACCTTGCTGAAAAGGATGGCAAACTGACTGATTATATCAATGCCAATTAT  5340
            1761   K   L   A   Q   L   A   E   K   D   G   K   L   T   D   Y   I   N   A   N   Y   1780
```

FIG.11

```
5341  GTTGATGGCTACAACAGACCAAAAGCTTATATTGCTGCCCAAGGCCCACTGAAATCCACA  5400
1781   V  D  G  Y  N  R  P  K  A  Y  I  A  A  Q  G  P  L  K  S  T   1800

5401  GCTGAAGATTTCTGGAGAATGATATGGGAACATAATGTGGAAGTTATTGTCATGATAACA  5460
1801   A  E  D  F  W  R  M  I  W  E  H  N  V  E  V  I  V  M  I  T   1820

5461  AACCTCGTGGAGAAAGGAAGGAGAAAATGTGATCAGTACTGGCCTGCCGATGGGAGTGAG  5520
1821   N  L  V  E  K  G  R  R  K  C  D  Q  Y  W  P  A  D  G  S  E   1840

5521  GAGTACGGGAACTTTCTGGTCACTCAGAAGAGTGTGCAAGTGCTTGCCTATTATACTGTG  5580
1841   E  Y  G  N  F  L  V  T  Q  K  S  V  Q  V  L  A  Y  Y  T  V   1860

5581  AGGAATTTTACTCTAAGAAACACAAAAAATAAAAAAGGGCTCCCAGAAAGGAAGACCCAGT  5640
1861   R  N  F  T  L  R  N  T  K  I  K  K  G  S  Q  K  G  R  P  S   1880

5641  GGACGTGTGGTCACACAGTATCACTACACGCAGTGGCCTGACATGGGAGTACCAGAGTAC  5700
1881   G  R  V  V  T  Q  Y  H  Y  T  Q  W  P  D  M  G  V  P  E  Y   1900

5701  TCCCTGCCAGTGCTGACCTTTGTGAGAAAGGCAGCCTATGCCAAGCGCCATGCAGTGGGG  5760
1901   S  L  P  V  L  T  F  V  R  K  A  A  Y  A  K  R  H  A  V  G   1920

5761  CCTGTTGTCGTCCACTGCAGTGCTGGAGTTGGAAGAACAGGCACATATATTGTGCTAGAC  5820
1921   P  V  V  V  H  C  S  A  G  V  G  R  T  G  T  Y  I  V  L  D   1940

5821  AGTATGTTGCAGCAGATTCAACACGAAGGAACTGTCAACATATTTGGCTTCTTAAAACAC  5880
1941   S  M  L  Q  Q  I  Q  H  E  G  T  V  N  I  F  G  F  L  K  H   1960

5881  ATCCGTTCACAAAGAAATTATTTGGTACAAACTGAGGAGCAATATGTCTTCATTCATGAT  5940
1961   I  R  S  Q  R  N  Y  L  V  Q  T  E  E  Q  Y  V  F  I  H  D   1980
```

FIG. 1J

```
5941 ACACTGGTTGAGGCCATACTTAGTAAAGAAACTGAGGTGCTGGACAGTCATATTCATGCC 6000
1981  T  L  V  E] A  I  L  S  K  E  T  E  V  L  D  S  H  I  H  A  2000

6001 TATGTTAATGCACTCCTCATTCCTGGACCAGCAGGCAAAACAAAGCTAGAGAAACAATTC 6060
2001  Y  V  N  A  L  L  I  P  G  P  A  G  K  T  K  L  E  K  Q  F  2020

6061 CAGCTCCTGAGCCAGTCAAATATACAGCAGAGTGACTATTCTGCAGCCCTAAAGCAATGC 6120
2021  Q  L  L  S  Q  S  N  I  Q  Q  S  D  Y  S  A  A  L  K  Q  C  2040

6121 AACAGGGAAAAGAATCGAACTTCTTCTATCATCCCTGTGGAAAGATCAAGGGTTGGCATT 6180
2041 [N  R  E  K  N  R  T  S  S  I  I  P  V  E  R  S  R  V  G  I  2060
```
PTPASE
DOMAIN II
```
6181 TCATCCCTGAGTGGAGAAGGCACAGACTACATCAATGCCTCCTATATCATGGGCTATTAC 6240
2061  S  S  L  S  G  E  G  T  D  Y  I  N  A  S  Y  I  M  G  Y  Y  2080

6241 CAGAGCAATGAATTCATCATTACCCAgcoCCCTCTCCTTCATACCATCAAGGATTTCTGG 6300
2081  Q  S  N  E  F  I  I  T  Q  H  P  L  L  H  T  I  K  D  F  W  2100

6301 oGGATGATATGGGACCATAATGCCCAACTGGTGGTTATGATTCCTGATGGCCAAAACATG 6360
2101  R  M  I  W  D  H  N  A  Q  L  V  V  M  I  P  D  G  Q  N  M  2120

6361 GCAGAAGATGAATTTGTTTACTGGCCAAATAAAGATGAGCCTATAAATTGTGAGAGCTTT 6420
2121  A  E  D  E  F  V  Y  W  P  N  K  D  E  P  I  N  C  E  S  F  2140

6121 AAGGTCACTCTTATGGCTGAAGAACACAAATGTCTATCTAATGAGGAAAAACTTATAATT 6480
2141  K  V  T  L  M  A  E  E  H  K  C  L  S  N  E  E  K  L  I  I  2160

6481 CAGGACTTTATCTTAGAAGCTACACAGGATGATTATGTACTTGAAGTGAGGCACTTTCAG 6540
2161  Q  D  F  I  L  E  A  T  Q  D  D  Y  V  L  E  V  R  H  F  Q  2180
```

FIG.1K

```
6541  TGTCCTAAATGGCCAAATCCAGATAGCCCCATTAGTAAAACTTTTGAACTTATAAGTGTT  6600
2181   C  P  K  W  P  N  P  D  S  P  I  S  K  T  F  E  L  I  S  V   2200

6601  ATAAAAGAAGAAGCTGCCAATAGGGATGGGCCTATGATTGTTCATGATGAGCATGGAGGA  6660
2201   I  K  E  E  A  A  N  R  D  G  P  M  I  V  H  D  E  H  G  G   2220

6661  GTGACGGCAGGAACTTTCTGTGCTCTGACAACCCTTATGCACCAACTAGAAAAAGAAAAT  6720
2221   V  T  A  G  T  F  C  A  L  T  T  L  M  H  Q  L  E  K  E  N   2240

6721  TCCGTGGATGTTTACCAGGTAGCCAAGATGATCAATCTGATGAGGCCAGGAGTCTTTGCT  6780
2241   S  V  D  V  Y  Q  V  A  K  M  I  N  L  M  R  P  G  V  F  A   2260

6781  GACATTGAGCAGTATCAGTTTCTCTACAAAGTGATCCTCAGCCTTGTGAGCACAAGGCAG  6840
2261   D  I  E  Q  Y  Q  F  L  Y  K  V  I  L  S  L  V  S  T  R  Q   2280

6841  GAAGAGAATCCATCCACCTCTCTGGACAGTAATGGTGCAGCATTGCCTGATGGAAATATA  6900
2281   E  E  N  P  S  T  S  L  D  S  N  G  A  A  L  P  D  G  N  I   2300

6901  GCTGAGAGCTTAGAGTCTTTAGTT  6924
2301   A  E  S  L  E  S  L  V   2308
```

FIG.1L

CAH

```
      MRILKRFLACIQLLCVCRLDWANGYYRQQRKLVEEIGWSYTGALNQKNWGKKYPTCNSPKQSPINIDEDLTQVNVNLKKLKFQGWDKTSLENTFIHNTGK
 101  TVEINLTNDYRVSGGVSEMVFKASKITFHMGKCNMSSDGSEHSLEGQKFPLEMQIYCFDADRFSSFEEAVKGKGKLRALSILFEVGTEENLDFKAIIDGV
 201  ESVSRFGKQAALDPFILLNLLPNSTDKYYIYNGSLTSPPCTDTVDWIVFKDTVSISESQLAVFCEVLTMQQSGYVMLMDYLQNNFREQQYKFSRQVFSSY
 301  TGKEEIHEAVCSSEPENVQADPENYTSLLVTWERPRVVYDTMIEKFAVLYQQLDGEDQTKHEFLTDGYQDLGAILNNLLPNMSYVLQIVAICTNGLYGKY
 401  SDQLIVDMPTDNPELDLFPELIGTEEIIKEEEEGKDIEEGAIVNPGRDSATNQIRKKEPQISTTIHYNRIGTKYNEAKTNRSPTIRGSEFSGKGDVPNTSL
 501  NSTSQPVTKLATEKDISLTSQIVTELPPHTVEGTSASLNDGSKTVLRSPHMNLSGTAESLNTVSITEYEEESLLTSFKLDTGAEDSSGSSPATSAIPFIS
 601  ENISQGYIFSSENPETITYDVLIPESARNASEDSTSSGSEESLKDPSMEGNVWFPSSTDITAQPDVGSGRESFLQTNYTEIRVDESEKTTKSFSAGPVMS
 701  QGPSVTDLEMPHYSTFAYFPTEVTPHAFTPSSRQQDLVSTVNVVYSQTTQPVYNGETPLQPSYSSEVFPLVTPLLLDNQILNTTPAASSSDSALHATPVF
 801  PSVDVSFESILSSYDGAPLLPFSSASFSSELFRHLHTVSQILPQVTSATESDKVPLHASLPVAGGDLLLEPSLAQYSDVLSTTHAASETLEFGSESGVLY
 901  KTLMFSQVEPPSSDAMMHARSSGPEPSYALSDNEGSQHIFTVSYSSAIPVHDSVGVTYQGSLFSGPSHIPIPKSSLIIPTASLLQPTHALSGDGEWSGAS
1001  SDSEFLLPDTDGLTALNISSPVSVAEFTYTTSVFGDDNKALSKSEIIYGNETELQIPSFNEMVYPSESTVMPNMYDNVNKLNASLQETSVSISSTKGMFP
1101  GSLAHTTTKVFDHEISQVPENNFSVQPTHTVSQASGDTSLKPVLSANSEPASSDPASSEMLSPSTQLFYETSASFSTEVILQPSFQASDVDTILLKTVLP
1201  AVPSDPILVETPKVDISSTMLHLIVSNSASSENMLHSTSVPVFDVSPTSHMHSASLQCLTISYASEKYEPVLLKSESSHQVVPSLYSNDELFQTANLEEI
1301  MQAHPPKGRHVFATPVLSIDEPLNTLINKLIHSDEILTSTKSSVTGKVFAGIPTVASDIFVSTDHSVPIGNGHVAITAVSPHRDGSVTSTKLLFPSKATS
```

FIG. 2A

FIG. 2B

```
1401  ELSHSAKSDAGLVGGGEDGDTDDDGDDDDDRDSDGLSIHKCMSCSSYRESQEKVMNDSDTHENSLMDQNNPISYSLSENSEEDNRVTSVSSDSQTGMDRS
1501  PGKSPSANGLSQKHNDGKEENDIQTGSALLPLSPESKAWAVLTSDEESGSGQGTSDSLNENETSTDFSFADTNEKDADGILAAGDSEITPGFPQSPTSSV
1601  TSENSEVFHVSEAEASNSSHESRIGLAEGLESEKKAVIPLVIVSALTFICLVWLVGILIYMRKCFQTAHFYLEDSTSPRVISTPPTPIFPISDDVGAIPI
1701  KHFPKHIVADLHASSGFTEEFEEVQSCTVDLGITADSSNHPDNKHKNRYINIVAYDHSRVKLAQLAEKDGKLTDYINANYVDGYNRPKAYIAAQGPLKSTA
1801  EDFWRMIWEHNVEVIVMITNLVEKGRRKCDQYWPADGSEEYGNFLVTQKSVQVLAYYTVRNFTLRNTKIKKGSQKGRPSGRVVTQYHYTQMPDMGVPEYS
1901  LPVLTFVRKAAYAKRHAVGPVVVHCSAGVGRTGTYIVLDSMLQQIQHEGTVNIFGFLKHIRSQRNYLVQTEEQYVFIHDTLVEAILSKETEVLDSHIHAY
2001  VNALLIEPGPAGKTKLEKQFQLLSQSNIQQSDYSAALKQQNREKNRTSSIIPVERSRVGISSLSGEGTDYINASYIMGYYQSNEFIITQHPLLHTIKDFWR
2101  MIWDHNAQLVVMIPDGQNMAEDEFVYWPNKDEPINCESFKVTLMAEEHKCLSNEEKLIIQDFILEATQDDYVLEVRHFQCPKWPNPDSPISKTFELISVI
2201  KEEAANRDCPMIVHDEHCGVTAGTFCALTTLMHQLEKENSVDVYQVAKMINLMRPGVFADIEQYQFLYKVILSLVSTRQEENPSTSLDSNGAALPDGNIA
2301  ESLESLV*
```

PERCENT SIMILARITY

| | RPTP Beta | RPTP Gamma | CAH I | CAH II | CAH III | CAH IV | CAH VI | CAH VII |
|---|---|---|---|---|---|---|---|---|
| RPTP Beta | 100.0 | | | | | | | |
| RPTP Gamma | 58.1 | 100.0 | | | | | | |
| CAH I | 50.4 | 48.1 | 100.0 | | | | | 47.1 |
| CAH II | | | | 49.0 | | | | 49.0 |
| CAH III | | | | 51.7 | 48.7 | | | 65.0 |
| CAH IV | | | | 73.0 | 53.7 | 44.8 | | 69.9 |
| CAH VI | | | | 100.0 | 69.9 | 48.0 | 46.6 | 64.5 |
| CAH VII | | | | | 71.0 | 44.6 | 45.0 | 47.1 |
|  | | | | | 100.0 | 48.7 | 48.1 | 51.3 |
|  | | | | | | 48.6 | 51.7 | 100.0 |
|  | | | | | | 100.0 | 53.7 | |
|  | | | | | | | 47.7 | |
|  | | | | | | | 100.0 | |

FIG. 3D

RECEPTOR-TYPE PHOSPHOTYROSINE PHOSPHATASE-β

This is a division, of application Ser. No. 08/015,973 filed Feb. 10, 1993, now U.S. Pat. No. 5,604,094, which is a continuation-in-part of Ser. No. 07/654,188 filed Feb. 26, 1991, abandoned, which is a continuation-in-part of Ser. No. 07/551,270 filed Jul. 11, 1990, abandoned.

TABLE OF CONTENTS
1. INTRODUCTION
2. BACKGROUND OF THE INVENTION
 2.1. PTKases
 2.2. PTPases
3. SUMMARY OF THE INVENTION
4. DESCRIPTION OF THE FIGURES
5. DETAILED DESCRIPTION OF THE INVENTION
6. EXAMPLE: ISOLATION AND CHARACTERIZATION OF HUMAN RPTPβ cDNA
 6.1. MATERIALS
 6.2. METHODS
 6.3. RESULTS
7. EXAMPLE: CHROMOSOMAL LOCALIZATION OF THE HUMAN RPTPβ GENE
 7.1. METHODS
 7.2. RESULTS
8. EXAMPLE: EXPRESSION OF RPTPα RNA
 8.1. ISOLATION OF MOUSE SEQUENCES HOMOLOGOUS TO HUMAN RPTPβ
 8.4. CELL LABELING AND IMMUNOPRECIPITATION
 8.5. RESULTS: DETECTION OF RPTPβ EXPRESSION IN A HUMAN NEUROBLASTOMA CELL LINE, Lan 5
9. EXAMPLE: IDENTIFICATION OF A VARIANT FORM OF RPTPβ
10. EXAMPLE: TISSUE SPECIFIC EXPRESSION OF RPTPβ
 10.1. METHODS: IN SITU HYBRIDIZATION ANALYSIS
 10.2. RESULTS
  10.2.1. Tissue Specific Expression of RPTPβ
  10.2.2. Localization of RPTPβ Expression in the Brain
11. GENERAL DISCUSSION FOR SECTIONS 6–10

1. INTRODUCTION

The invention in the field of biochemistry and cell and molecular biology relates to novel receptor-type protein tyrosine phosphatase proteins or glycoproteins, termed RPTPα, β and γ, DNA coding therefor, methods for production and identification of the proteins, and methods for screening compounds capable of binding to and inhibiting or stimulating PTPase enzymatic activity.

2. BACKGROUND OF THE INVENTION

The identification of several growth factor receptors and retroviral oncogenes as tyrosine-specific protein kinases indicated that protein phosphorylation on tyrosine residues plays a key role in cellular growth control. This notion has recently received support by the observation that the level of tyrosine phosphorylation of enzymes thought to play an important role in signal transduction (such as phospholipase C) correlates with their increased activity upon growth factor stimulation, thus establishing a functional role for tyrosine phosphorylation (Ullrich, A., et al., *Cell* 61:203–212 (1990)).

The degree and pattern of phosphorylation of tyrosine residues on cellular proteins are regulated by the opposing activities of protein-tyrosine kinases (PTKases; ATP:protein-tyrosine O-phosphotransferase, EC 2.7.1.112) and protein-tyrosine-phosphatases (PTPases; protein-tyrosine-phosphate phosphohydrolase, EC 3.1.3.48). The structural characteristics and evolution of PTKases as well as their role in the regulation of cell growth have been reviewed (Hunter, T., et al., *Annu. Rev. Biochem.* 54:897–930 (1985); Ullrich, A., et al., supra).

2.1. PTKases

Tyrosine kinases comprise a discrete family of enzymes having common ancestry with, but major differences from, serine/threonine-specific protein kinases (Hanks, S. K. et al., (1988) *Science* 241, 42–52). The mechanisms leading to changes in activity of tyrosine kinases are best understood for receptor-type tyrosine kinases which have a transmembrane topology (Ullrich, A. et al., supra). With such kinases, the binding of specific ligands to the extracellular domain of these enzymes is thought to induce their oligomerization leading to an increase in tyrosine kinase activity and activation of the signal transduction pathways (Ullrich, A. et al., supra). The importance of this activity is supported by the knowledge that dysregulation of kinase activity through mutation or over-expression is a mechanism for oncogenic transformation (Hunter, T et al., supra; Ullrich, A. et al., 1990, supra).

2.2. PTPases

The protein phosphatases are composed of at least two separate and distinct families (Hunter, T. *Cell*, 58:1013–1016 (1989)), the protein serine/threonine phosphatases and the protein tyrosine phosphatases. This is in contrast to protein kinases, which show clear sequence similarity between serine/threonine-specific and tyrosine-specific enzymes.

There appear to be two varieties of PTPase molecules. The first group is comprised of small, soluble enzymes that contain a single conserved phosphatase catalytic domain, and include (1) placental PTPase 1B (Charbonneau, H. et al., *Proc. Natl. Acad. Sci.* 86:5252–5256 (1989); Chernoff, J. et al., *Proc. Natl. Acad. Sci. USA* 87:2735–2789 (1990)), (2) T-cell PTPase (Cool, D. E. et al., *Proc. Natl. Acad. Sci. USA* 86:5257–5261 (1989)), and (3) rat brain PTPase (Guan, K., et al., *Proc. Natl. Acad. Sci. USA*, 87:1501–1505 (1990).

The second group is made up of the more complex, receptor-linked PTPases, termed RPTPs, which are of high molecular weight and contain two tandemly repeated conserved domains separated by 56–57 amino acids. One example of RPTPs are the leukocyte common antigens (LCA) (Ralph, S. J., *EMBO J.*, 6:1251–1257 (1987); Charbonneau, H., et al., *Proc. Natl. Acad. Sci. USA*, 85:7182–7186 (1988)). LCA, also known as CD45, T200 and Ly-5 (reviewed in Thomas, M. L., *Ann. Rev. Immunol.* 7:339–369 (1989)) comprises a group of membrane glycoproteins expressed exclusively in hemopoietic (except late erythroid) cells, derived from a common gene by alternative splicing events involving the amino terminus of the proteins. Whereas the precise function of CD45 is unknown, many studies have implicated these antigens in a number of processes, including the activity of cytotoxic T lymphocytes and natural killer cells, IL-2 receptor expression, B-cell differentiation, and T lymphocyte proliferation (Pingel, J. T. et al., *Cell* 58:1055–1065 (1989)).

Other examples of RPTPs are the LCA-related protein, LAR (Streuli, M., et al., *J. Exp. Med.*, 168:1523–1530

(1988)), and the LAR-related Drosophila proteins DLAR and DPTP (Streuli, M., et al., *Proc. Natl. Acad. Sci. USA*, 86:8698–8702 (1989)). Jirik et al. screened a cDNA library derived from the human hepatoblastoma cell line, HepG2, with a probe encoding the two PTPase domains of LCA (FASEB J. 4: A2082 (1990), abstr. 2253) and discovered a cDNA clone encoding a new RPTP, named He-PTP. The HePTP gene appeared to be expressed in a variety of human and murine cell lines and tissues.

While we are beginning to understand more about the structure and diversity of the PTPases, much remains to be learned about their cellular functions. It has been suggested (Tonks, N. K., et al., *Biochemistry*, 27:8695–8701 (1988)) that the small, soluble PTPase enzymes may have a "housekeeping" function. On the other hand, the RPTPs would be expected to be more restricted in their activities because of their location in the cell membrane and their potential regulation by extracellular ligands. Regarding the role of LCA (CD45) in T cells, it was found that T cell clones deficient in the expression of LCA failed to proliferate when stimulated by a specific antigen or by cross-linking of CD3 (Pingel, J. T., et al., supra). PTPase cross-linking inhibits T cell receptor CD3-mediated activation in human T cells (Kiener, P. A. et al., *J. Immunol.* 143:23–28 (1989)). The PTPase activity of LCA plays a role in the activation of pp56$^{lck}$, a lymphocyte-specific PTKase (Mustelin, T., et al., *Proc. Natl. Acad. Sci. USA*, 86:6302–6306 (1989); Ostergaard, H. L., et al., *Proc. Natl. Acad. Sci. USA*, 86:8959–8963 (1989)). These authors hypothesized that the phosphatase activity of LCA activates pp56$^{lck}$ by dephosphorylation of a C-terminal tyrosine residue, which may, in turn, be related to T-cell activation.

Using site-directed mutagenesis to determine which of four conserved cysteines in LCA (two per phosphatase domain) was required for enzyme activity toward artificial substrates, Streuli et al. (1989, supra) found that only one cysteine residue (residue 177 of LCA phosphatase domain-1) of LCA was essential for activity, indicating that, most likely, only the first phosphatase domain has enzymatic activity. However, the possibility that the second domain can dephosphorylate a different substrate was not excluded. More recently, Streuli et. al. (*EMBO J.*, 9:2399–2407 (1990)) determined that the second conserved domain of LCA (and of LAR) lacked detectable phosphatase activity but sequences within the domain could influence substrate specificity.

In order to better understand and to be able to control phosphotyrosine metabolism, one must comprehend not only the role of kinase activity, but also the action of phosphatase enzymes as well. Elevation of cellular phosphotyrosine may occur through mechanisms not involving the activation of a tyrosine kinase itself. For instance, expression of the v-crk oncogene, though not a tyrosine kinase itself, induces the phosphorylation of tyrosine residues through a poorly understood mechanism (Mayer, B. J. et al. (1988) *Nature* 332, 272–275). Potentially, such an outcome could result from either mutation of the substrate or through a general decrease in cellular phosphatase activity, especially in view of the normally high turnover rate of cellular tyrosine-phosphate (Sefton, B. M. et al. (1980) *Cell* 20, 807–816). The latter possibility is suggested by the demonstration that tyrosine phosphatase inhibitors can "reversibly transform" cells (Klarlund, J. K. *Cell* 41: 707–717 (1985)). PTPases could therefore be viewed as potential recessive oncogenes.

It is becoming clear that dephosphorylation of tyrosine can by itself function as an important regulatory mechanism. Dephosphorylation of a C-terminal tyrosine residue stimulates tyrosine kinase activity in the src-family of tyrosine kinases (Hunter, T. (1987) *Cell* 49, 1–4). Tyrosine dephosphorylation has been suggested to be an obligatory step in the mitotic activation of the MPF (maturation promoting factor) kinase (Morla, A. O. et al. (1989) *Cell* 58, 193–203). Lastly, mutant analysis of primitive eukaryotes has established crucial roles for serine phosphatase in cellular physiology (Cyert, M. S. et al. (1989) *Cell* 57, 891–893). These observations point out the need in the art for increasing our understanding of the mechanisms that regulate tyrosine phosphatase activity.

It is clear in the art that further analysis of structure-function relationships among these membrane receptors are needed to gain important understanding of the mechanisms of cell growth, differentiation, and oncogenesis.

3. SUMMARY OF THE INVENTION

The present inventor has conceived of a role for RPTPs in cellular control mechanisms, both as potential anti-oncogenes, and as effectors in a newly discovered mechanism of transmembrane signalling. They therefore undertook a search for individual RPTP genes and proteins potentially involved in such processes, and describe herein the identification of a novel, member of the RPTP family, RPTPβ, which has a transmembrane topology. The extracellular domains of members of this RPTP family are unrelated to any other RPTPs previously described. The novel RPTPβ, in a manner analogous to receptor tyrosine kinases, is subject to direct regulation by extracellular ligands which bind to the extracellular portion.

The present invention thus provides a human receptor-type protein tyrosine phosphatase-β (RPTPβ) protein or glycoprotein molecule, a functional derivative of human RPTPβ or a homolog of human RPTPβ in another mammalian species. When the RPTPβ molecule is of natural origin, it is substantially free of other proteins or glycoproteins with which it is natively associated. RPTPβ is naturally expressed in mammalian brain and is developmentally and anatomically regulated. The RPTPβ molecule of the present invention may not be of natural origin, and, may be prepared by chemical or recombinant means. Thus, the substantially pure RPTPβ protein or glycoprotein of the present invention may be produced by biochemical purification of the protein or glycoprotein of natural origin; alternatively, the RPTPβ may be produced by recombinant means in prokaryotic or eukaryotic hosts.

In particular, the invention is directed to a RPTPβ having the amino acid sequence SEQ ID NO:1 of human RPTPβ, shown in FIGS. 1A–1L and 2A–2B, or a functional derivative thereof.

The invention is further directed to a nucleic acid molecule, preferably, DNA, consisting essentially of a nucleotide sequence encoding RPTPβ, preferably of human origin, or encoding a functional derivative thereof. The nucleic acid molecule, preferably comprises the sequence SEQ ID NO:2 (see FIGS. 1A–1L). The DNA molecule is preferably cDNA or genomic DNA. The invention is further directed to the DNA molecule in the form of an expression vehicle, as well as prokaryotic and eukaryotic hosts transformed or transfected with the DNA molecule.

Also included in the present invention is a process for preparing an RPTPβ protein or glycoprotein, or a functional derivative thereof, comprising:

(a) culturing a host capable of expressing the protein, glycoprotein or functional derivative under culturing conditions;

(b) expressing the protein, glycoprotein or functional derivative; and
(c) recovering the protein, glycoprotein or functional derivative from the culture.

The invention is directed to an antibody, either polyclonal, monoclonal, or chimeric, which is specific for the RPTPβ protein or glycoprotein.

The invention is also directed to a method for detecting the presence of nucleic acid encoding a normal or mutant RPTPβ in a subject comprising:
(a) contacting a cell or an extract thereof from the subject with an oligonucleotide probe encoding at least a portion of the normal or mutant RPTPβ under hybridizing conditions; and
(b) measuring the hybridization of the probe to the nucleic acid of the cell, thereby detecting the presence of the nucleic acid.

The DNA can be selectively amplified, using the polymerase chain reaction, prior to assay.

The invention is further directed to a method for detecting the presence, or measuring the quantity of RPTPβ in a cell or cells, comprising:
(a) contacting said cell or an extract thereof with an antibody specific for an epitope of the RPTPβ; and
(b) detecting the binding of the antibody to the cell or extract thereof, or measuring the quantity of antibody bound,
thereby detecting the presence or measuring the quantity of the RPTPβ.

The present invention is also directed to methods for identifying and isolating a compound capable of binding to RPTPβ from a chemical or biological preparation comprising:
(a) attaching the RPTPβ, or the ligand-binding portion thereof, to a solid phase matrix;
(b) contacting the chemical or biological preparation with the solid phase matrix allowing the compound to bind, and washing away any unbound material;
(c) detecting the presence of the compound bound to the solid phase; and, for purposes of isolation,
(d) eluting the bound compound, thereby isolating the compound.

Finally, the invention includes a method for identifying an agent capable of stimulating or inhibiting the phosphatase enzymatic activity of RPTPβ, comprising:
(a) contacting the agent with RPTPβ in pure form, in a membrane preparation, or in a whole live or fixed cell;
(b) incubating the mixture in step (a) for a sufficient interval;
(c) measuring the enzymatic activity of RPTPβ;
(d) comparing the enzymatic activity to that of RPTPβ incubated without the agent,
thereby determining whether the agent stimulates or inhibits the activity.

4. DESCRIPTION OF THE FIGURES

FIGS. 1(1)–1(8) show the nucleotide sequence (SEQ ID NO:2) and predicted amino acid sequence (SEQ ID NO:1) of human RPTPβ.

FIGS. 2A–2B presents the amino acid sequence of RPTPβ. The hydrophobic signal peptide is underlined and the transmembrane peptide is designated in bold. The 21 potential N-glycosylation sites are indicated by filled arrows. The CAH-related domain and the two phosphatase domains, DI and DII, are indicated by the boxes. The open arrows represent the boundaries of the deletion in the variant RPTPβ clones.

Figure 3A:
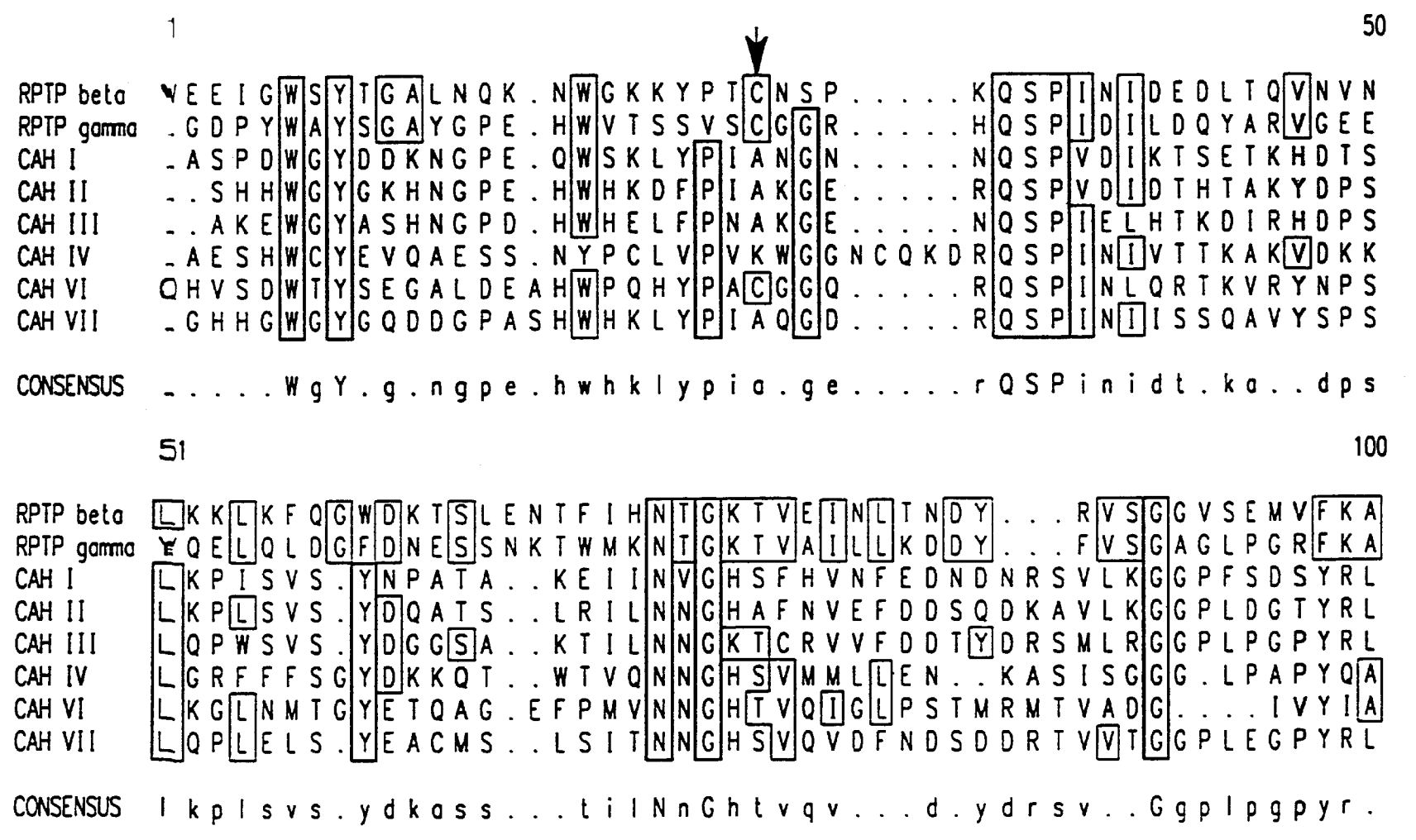
Figure 3B:
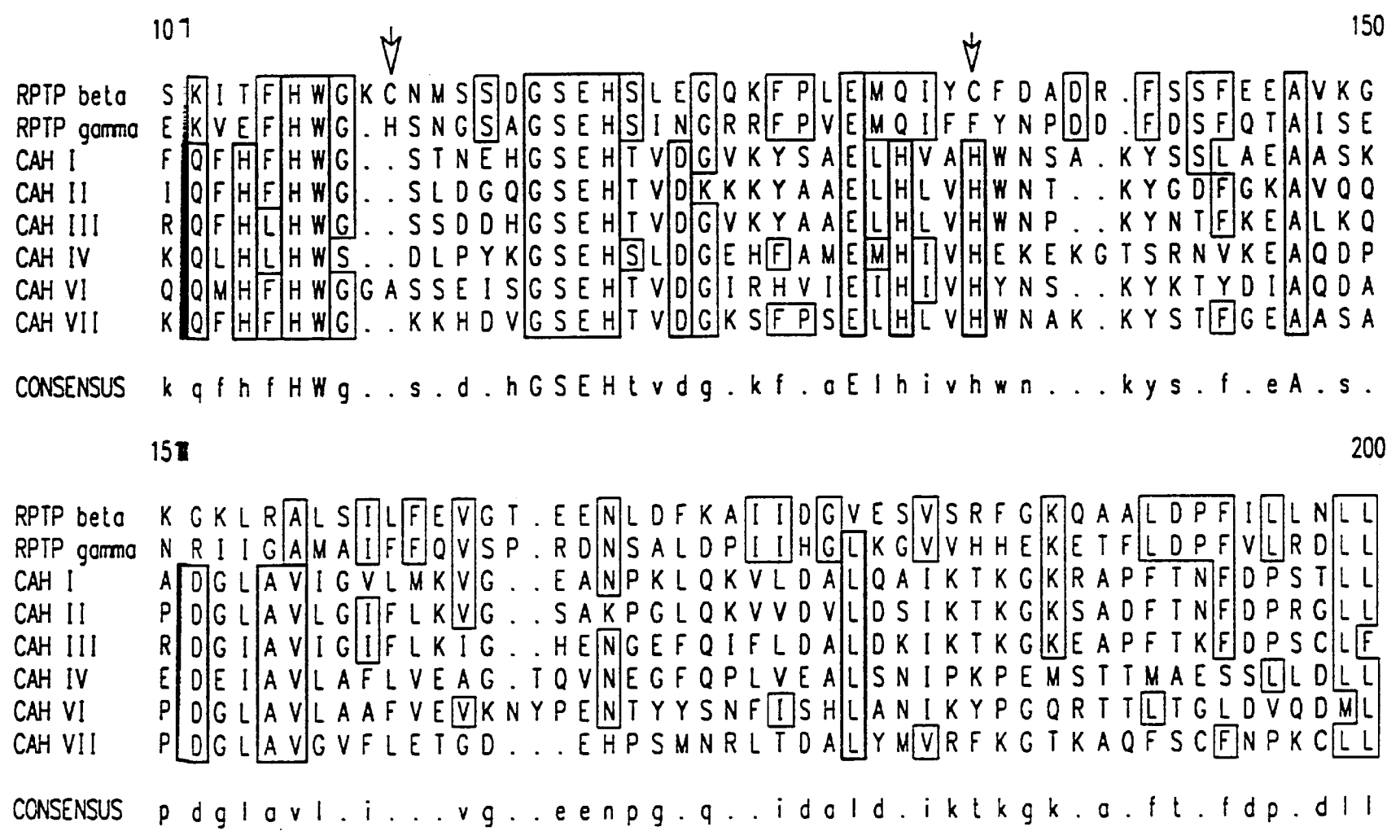
Figure 3C:
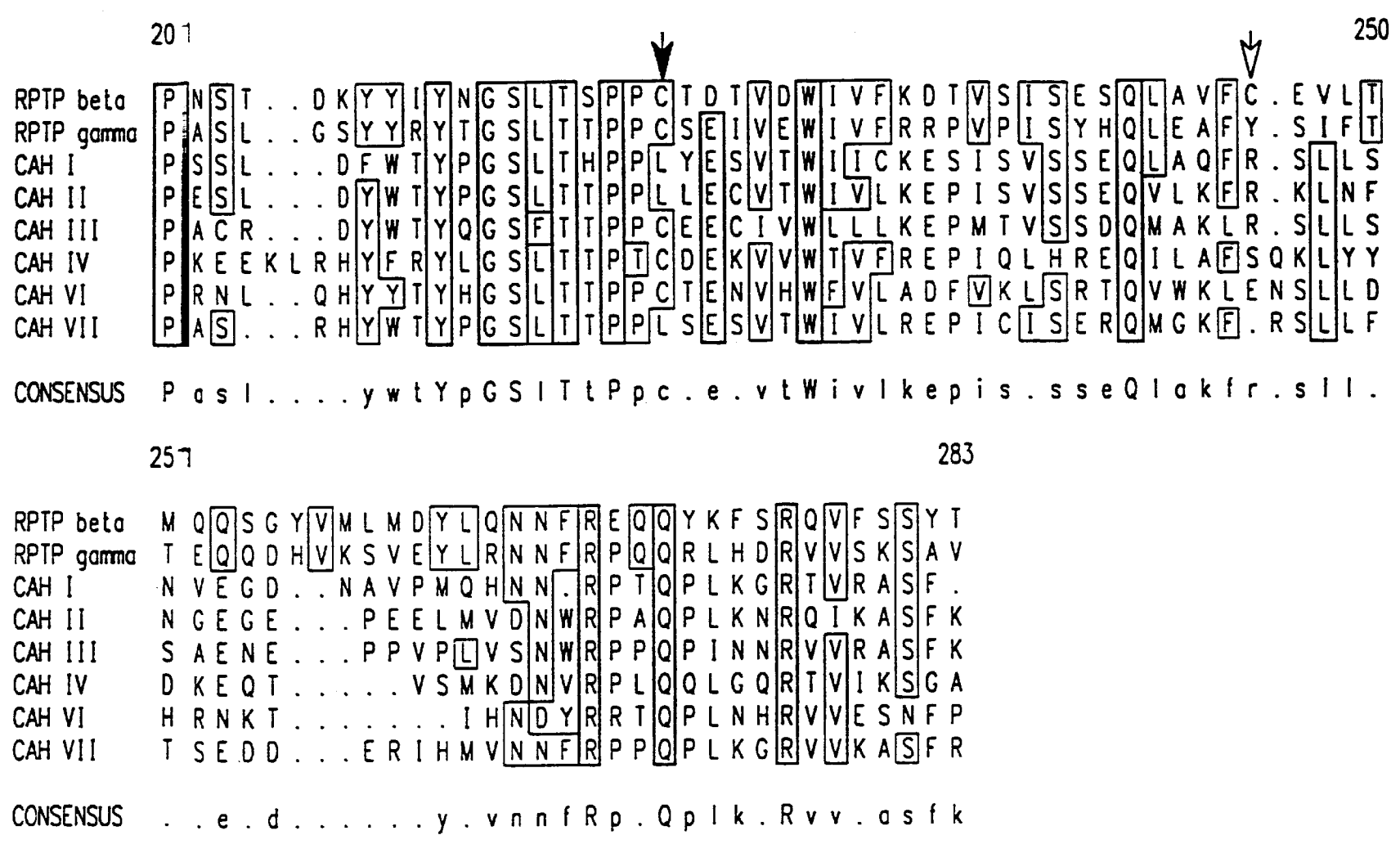

FIGS. 3A–3D describes the identification of a CAH-related domain in the extracellular region of RPTPβ. FIGS. 3A–3C shows an alignment of the amino acid sequence of the CAH-related domain of RPTPβ with the corresponding domain of RPTPγ and six different isoforms of CAH (I–VII). The amino acid sequences that are boxed in black are those that are identical in all six isoforms of CAH. The sequences boxed in the gray hatches are those that are identical between the CAH-related domains of RPTPβ and RPTPγ. FIG. 3D is a table showing the percent similarity (taking into account conservative amino acid substitutions) between the CAH-related domains of RPTPβ, RPTPγ and the six isoforms of CAH.

Figure 4B:
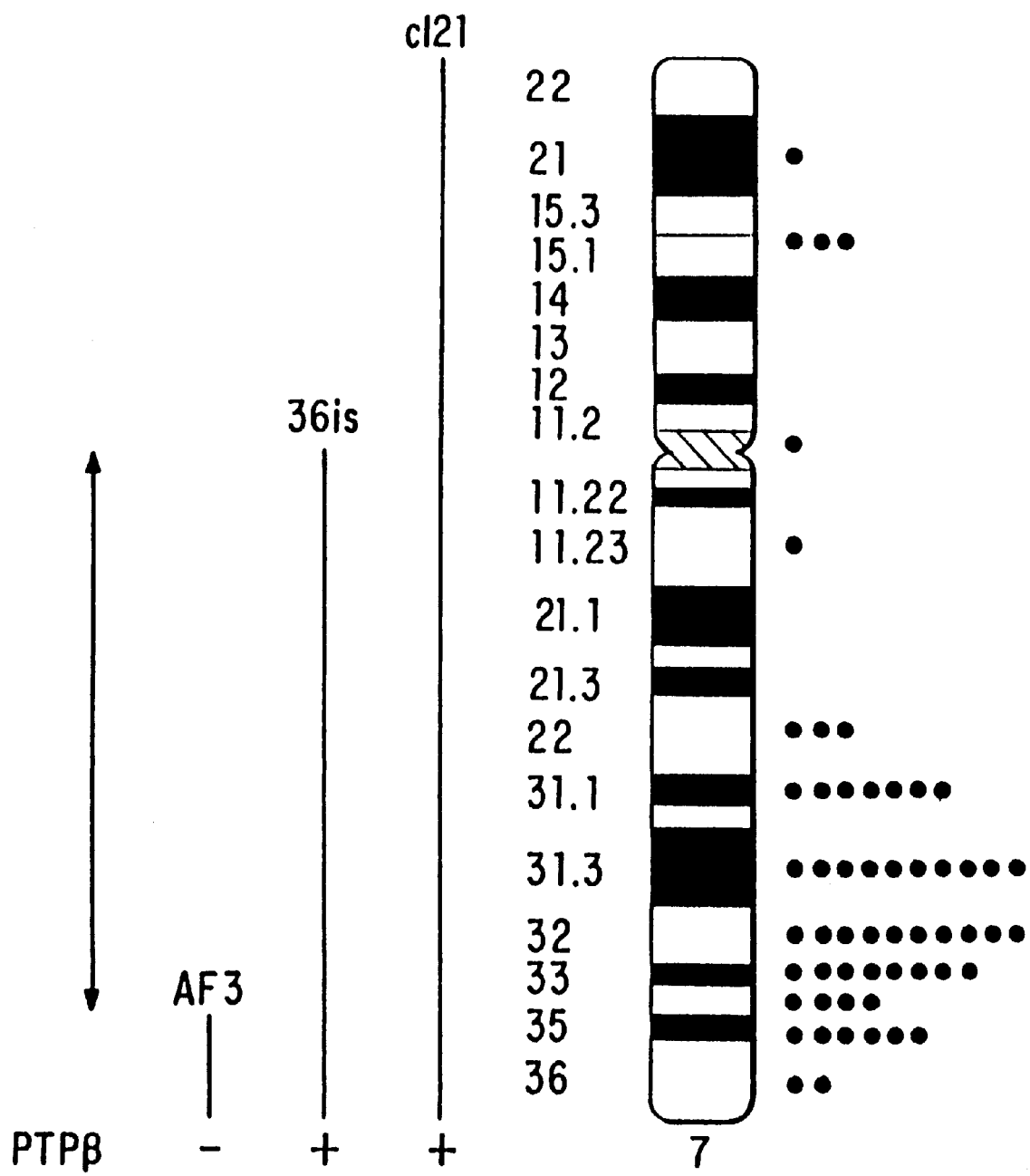

FIGS. 4A–4B shows the chromosomal localization of human RPTPβ. A completely stippled box indicates that the hybrid designated in the left column contains the chromosome indicated in the upper row; lower-right stippling indicates the presence of the long arm (or a part of the long arm, indicated by small fraction of stippling) of the chromosome indicated; upper left stippling indicates the presence of the short arm (or partial short arm) of the chromosome indicated; an open box indicates absence of the chromosome indicated; the column for chromosome 7 is boldly outlined and stippled to highlight the correlation of the presence of this chromosome with the presence of the RPTPβ gene. The pattern of retention of the RPTPβ sequences in the hybrids is shown on the right where the presence of the gene is indicated by a "+" sign in a stippled box and absence of the gene is indicated by a "−" sign in an open box. FIG. 4B shows a schematic diagram of chromosome 7, indicating that RPTPβ maps to 7q31–q33. chromosomal in situ hybridization of a 1.8 kb RPTPβ cDNA to normal human metaphase chromosomes confirmed localization of the gene to 7q and revealed a peak of grains centered over the 7q31.3–q32 region, as illustrated. Each dot to the right represents an autoradiographic grain.

Figure 5A:
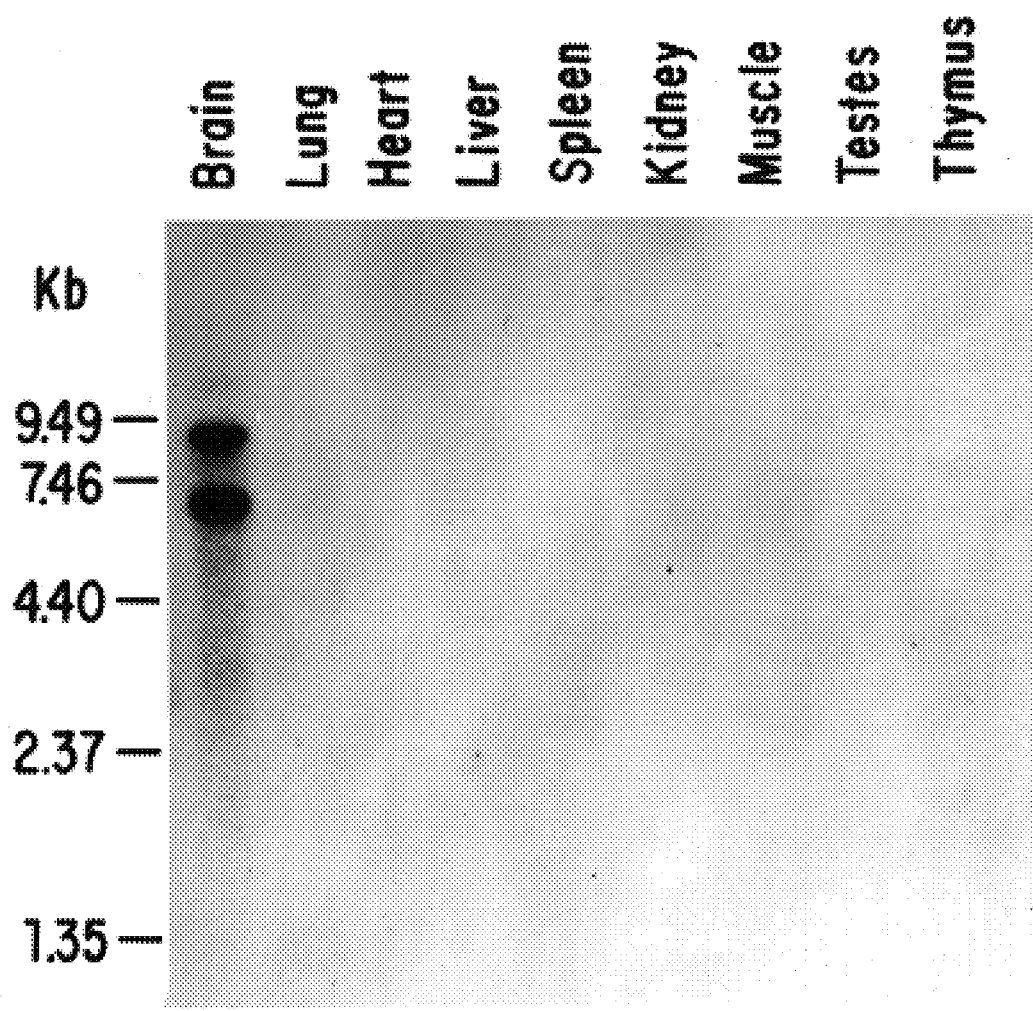
Figure 5B:
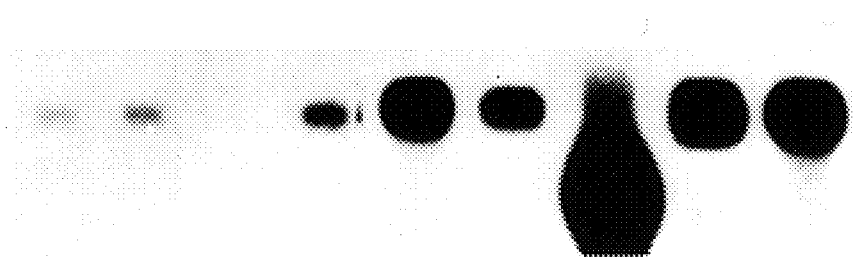
Figure 5C:
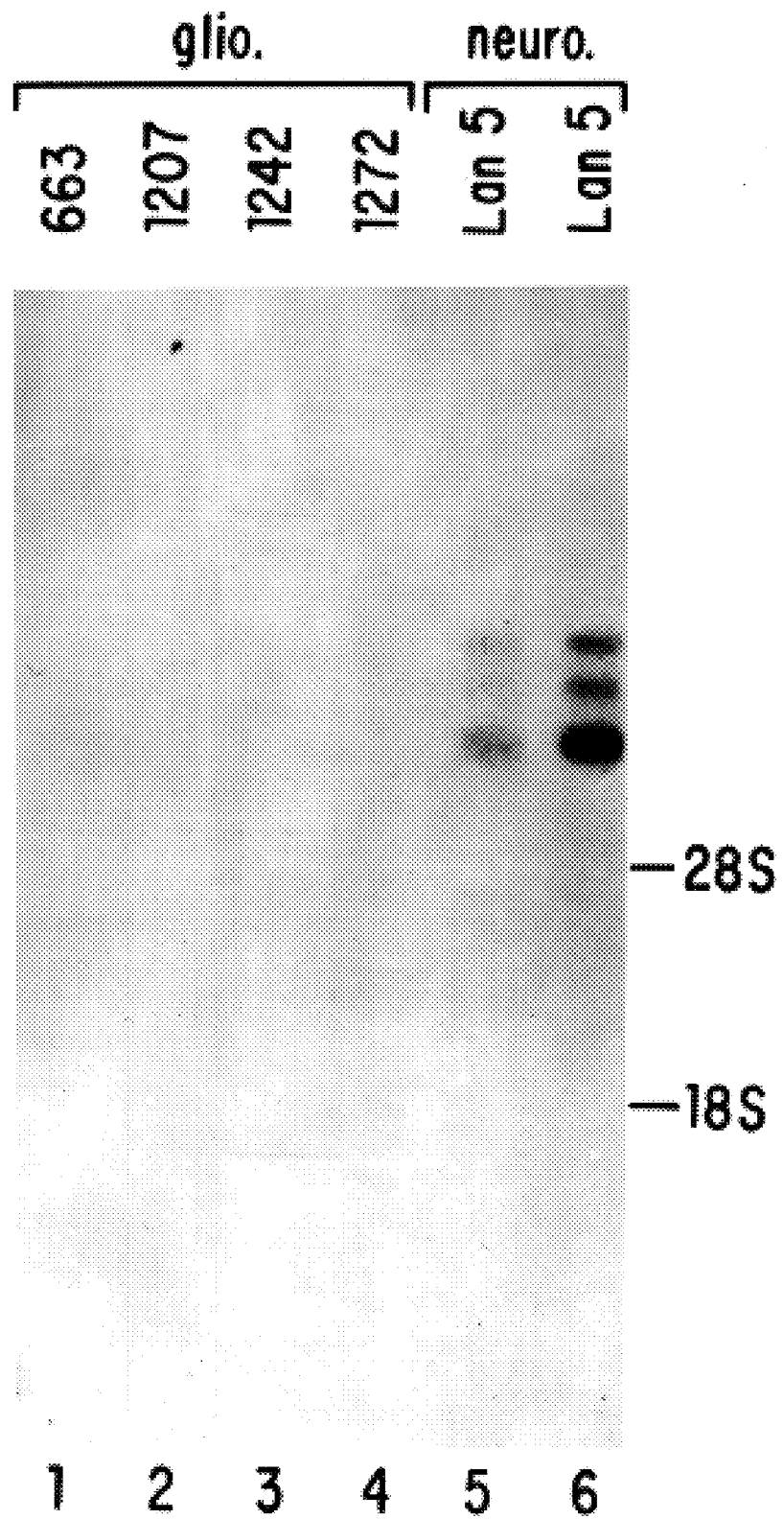

FIGS. 5A–5C show the expression of RPTPβ mRNA in various human cell lines and murine tissues using Northern blot analysis. In FIG. 5A, 20 μg of total cellular RNA (lanes 1–5) or 1 μg of poly-A$^+$ RNA (lane 6) isolated from the various indicated glioblastoma and neuroblastoma cell lines were loaded onto a 1% agarose/2.2M formaldehyde RNA gel and probed with a DNA fragment isolated from the human brain stem cDNA clone that begins with sequences just 5' of the region encoding the transmembrane region and extends and includes all of the sequence in the phosphatase domain I. In FIG. 5B, poly-A$^+$ RNA (1 μg/sample) from the indicated murine tissues were loaded onto an RNA gel and probed with the PCR-amplified murine DNA fragment, pBSMBDII. FIG. 5C shows the blot from FIG. 5B which was stripped of the probe and rehybridized with a $^{32}$P-labeled rat actin probe.

Figure 6:
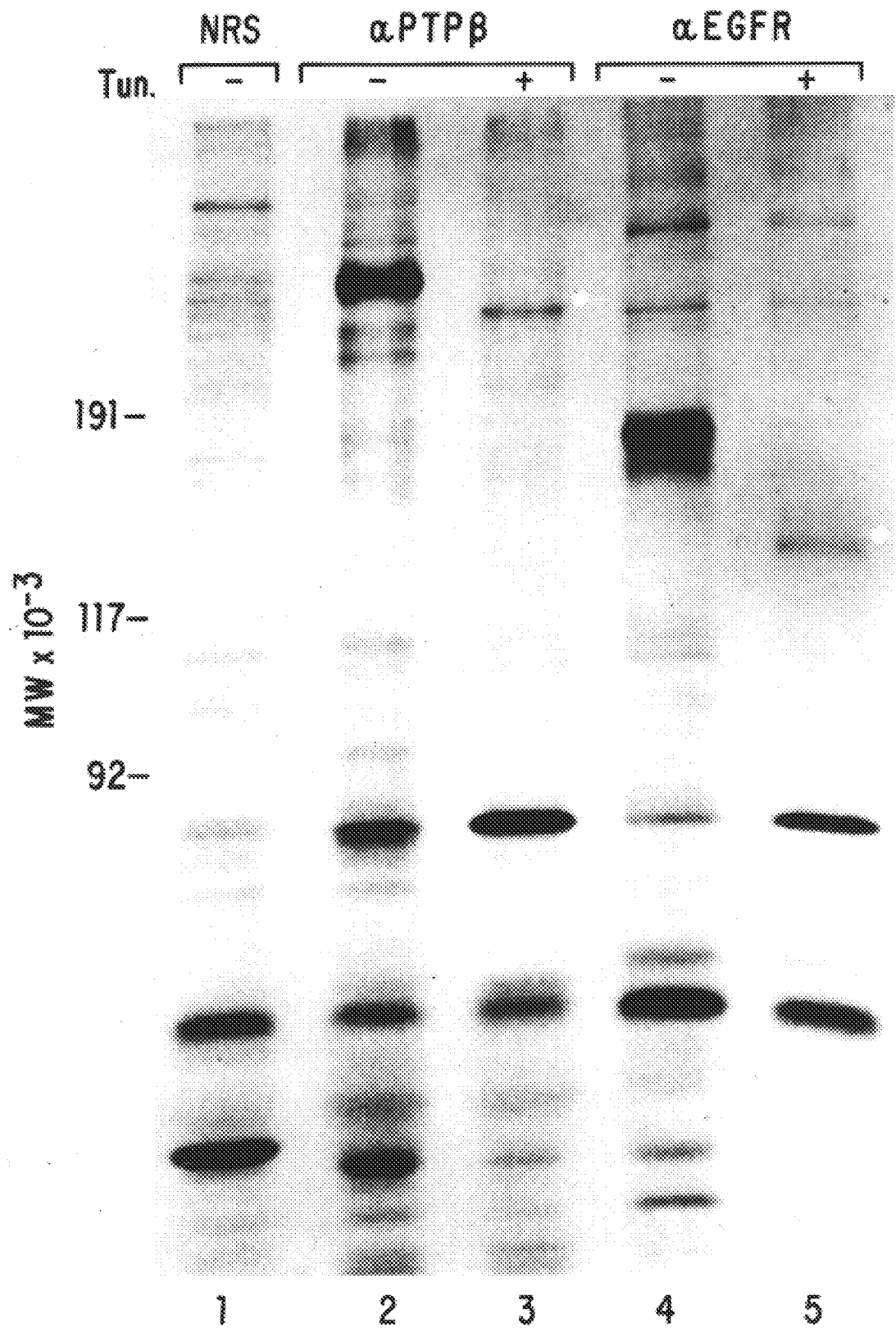

FIG. 6 is a gel pattern showing the identification of endogenous RPTPβ protein expressed in Lan 5cells. RPTPβ was immunoprecipitated with normal rabbit serum (NRS, lane 1) or immune anti-RPTPβ antiserum (αPTPβ, lanes 2 and 3) from lysates of [$^{35}$S]methionine-labeled Lan 5 cells in the absence (lanes 1 and 2) or presence (lane 3) of tunicamycin. Immunoprecipitation of the EGF receptor with RK2 antibody (αEGFR, lanes 4 and 5) from lysates of [$^{35}$S]methionine-labeled Lan 5 cells labeled in the absence (lane 4) or presence (lane 5) of tunicamycin.

Figure 7A:
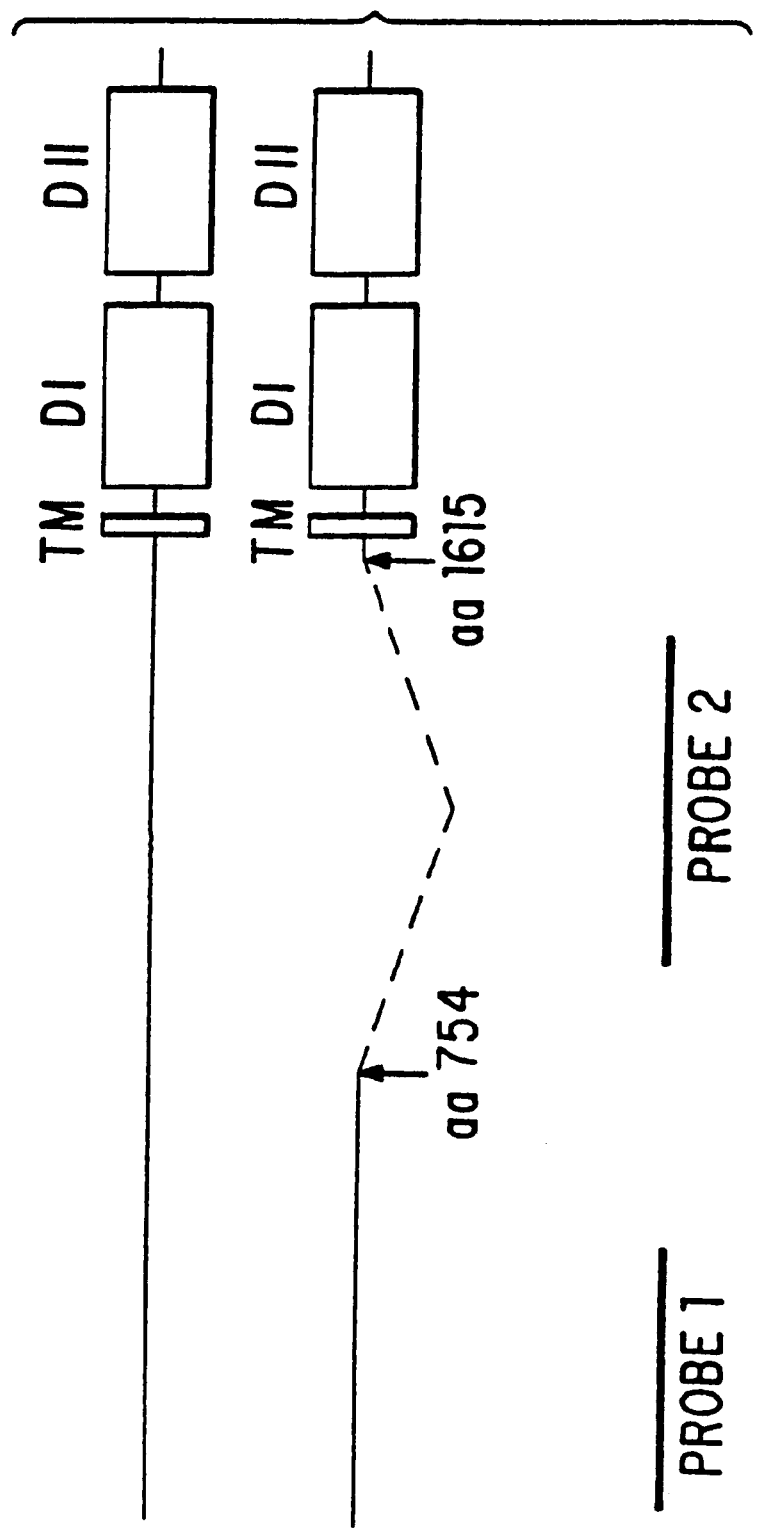
Figure 7B:
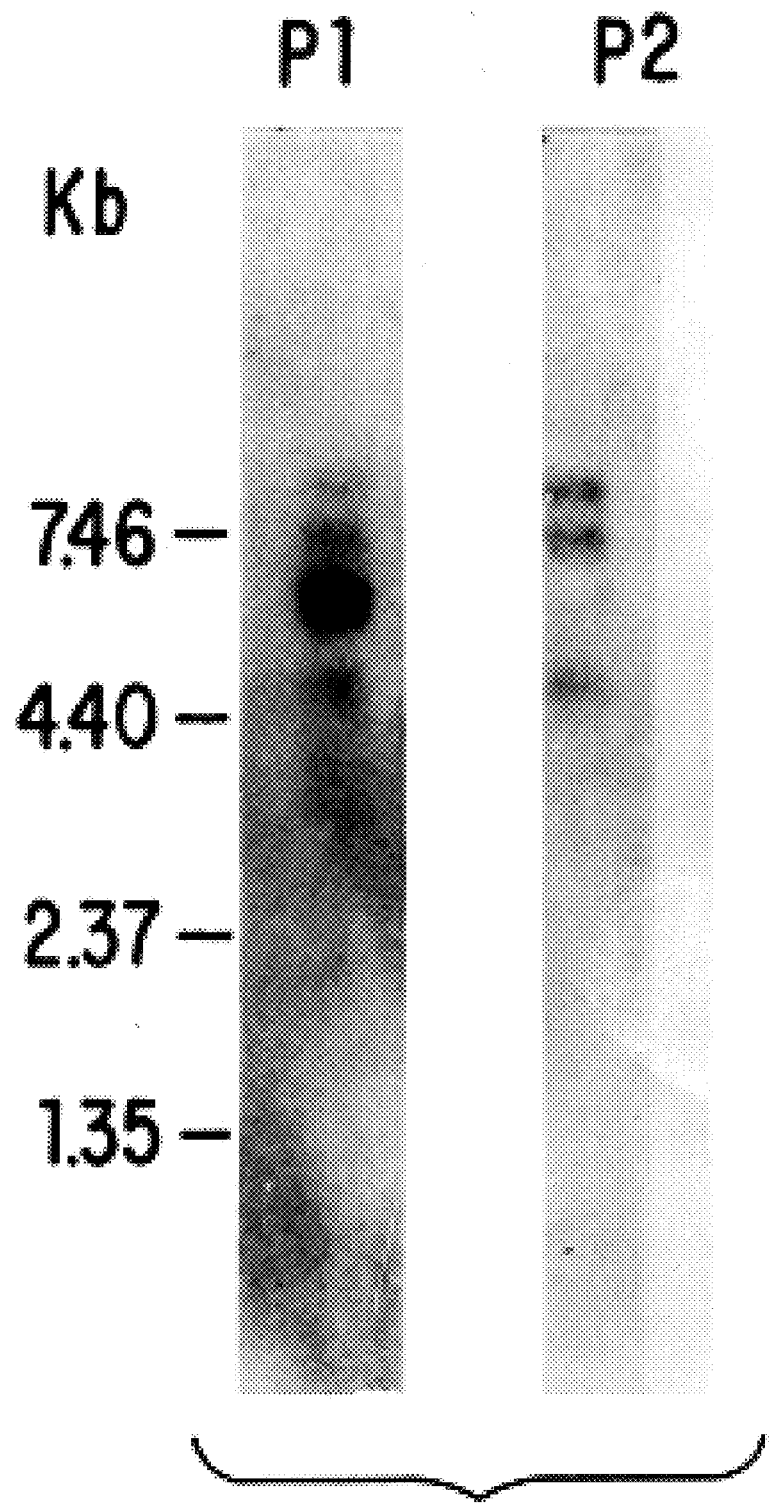

FIGS. 7A and 7B (FIG. 6) shows the identification of variant RPTPβ using Northern blots. FIG. 7A is a schematic diagram of the protein encoded by the full length RPTPβ cDNA compared to the putative protein encoded by the two independently isolated cDNA clones that carry an identical deletion of 2577 bp in the extracellular region of the protein. The position of the deletion is indicated by the dotted line with the number of amino acids remaining at both the 5' and 3' end of the deletion indicated. The location of the two probes using in Northern analysis (probes 1 and 2) are indicated. TM, transmembrane peptide; DI, phosphatase domain I; DII, phosphatase domain II. FIG. 7B shows the results of Northern analysis. poly-A⁺ RNA (1 μg) isolated from the Lan 5 neuroblastoma cell line was separated on a RNA formaldehyde gel and probed with human probe 1 (P1) that contains 1.3 kb of sequences derived from the extreme 5' end of the cDNA clone and human probe 29P2) that contains 1.6 kb of sequences derived from the portion of the full length cDNA clone that is deleted in the variant cDNA clones.

Figure 8A:
Figure 8B:
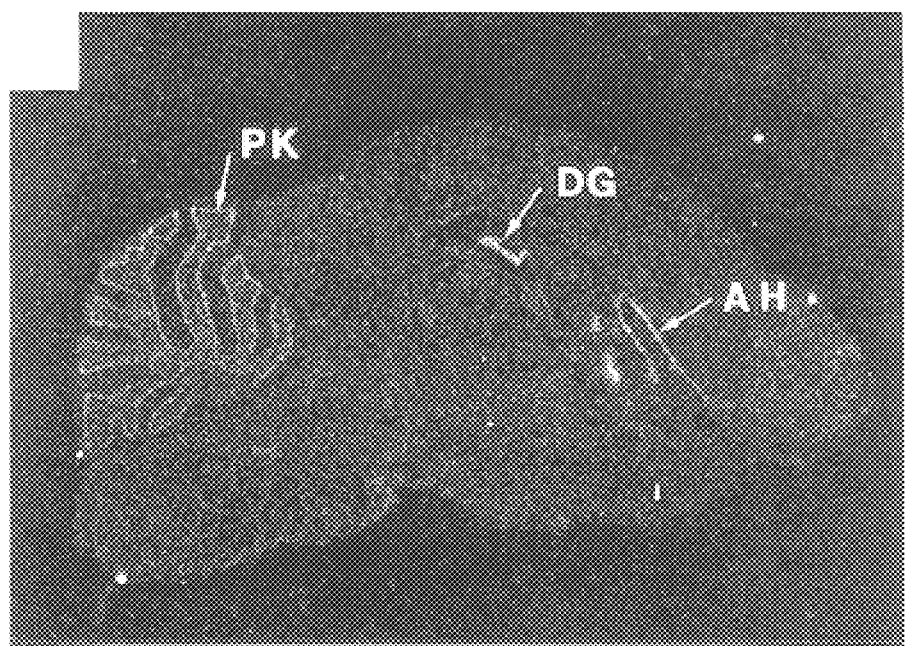

FIGS. 8A and 8B show the results of an in situ hybridization analysis of RPTPβ expression in developing and adult mouse brain. FIG. 8A shows a sagittal section through an embryonic day 20 (E2) mouse, and indicates that RPTPβ was expressed in the developing nervous system. The highest level of expression was observed in the ventricular and subventricular zones (VZ). FIG. 8B is a sagittal section through an adult mouse brain and shows discrete bands of expression in the Purkinje cells of the cerebellum (PK), the dentate gyrus (DG), and the subependymal layer of the anterior horn of the lateral ventricle (AH).

5. DETAILED DESCRIPTION OF THE INVENTION

Through the use of recombinant DNA methods, the present inventor has identified novel mammalian receptor-type (transmembrane) protein tyrosine phosphatases (PTPase; EC 3.1.3.48). In view of their receptor-like structure, and the likelihood that they are part of a family, the inventor has termed these protein, RPTPα, RPTPβ, RPTPγ, etc. (receptor protein tyrosine phosphatase-alpha, beta, gamma, etc.). The family is designated herein as the "RPTPs" (and is also referred to as R-PTPases)

Human RPTPβ is a protein or glycoprotein having 2307 amino acids. In contrast, human RPTPα has 802 amino acids and human RPTPγ has 1445 amino acids. RPTPβ has an extracellular domain, a single transmembrane domain and a cytoplasmic portion with two tandem catalytic phosphatase domains. The extracellular domain contains a stretch of 266 amino acids with striking homology to the zinc-containing enzyme carbonic anhydrase (CAH) indicating that RPTPβ together with RPTPγ (HPTPζ) represent a subfamily of RPTPs.

The gene encoding RPTPβ, denoted RPTPβ (or PTPζ) has been mapped by the present inventor to human chromosome $7_q31-_q33$, a site rather distinct from the site to which RPTPγ was mapped ($3_p14.2-_p21$).

The cDNA cloning of human RPTPβ, and the complete DNA and amino acid sequence of human RPTPβ are described herein. Northern analysis has been used to identify the natural expression of the protein in various cells and tissues. RPTPγ was shown to be expressed in anatomically distinct regions of rat brain and its expression was found to be developmentally regulated.

Remarkably, in addition to being composed of intracellular domains having enzymatic activity, the receptor family to which RPTPs belong includes transmembrane proteins having and N-terminal extracellular domains, analogous to the tyrosine kinase enzyme family (Tonks, N. K. et al. (1988) *Biochemistry* 27:8695–8701; Charbonneau, H. et al. (1988) *Proc. Natl. Acad. Sci. USA* 85:7182–7186; Streuli, M. et al. (1988) *J. Exp. Med.* 168:1523–2530; Streuli, M. et al. (1989) *Proc. Natl. Acad. Sci. USA* 86:8698–8702). The present inventor has therefore concluded that ligands in the extracellular environment can control the activity of this membrane-associated subclass of PTPases.

The present inventor has further produced a polyclonal antibody to RPTPβ by immunization or rabbits with a 15 amino acid synthetic peptide of RPTPβ conjugated to a carrier.

RPTPβ is useful in methods for screening drugs and other agents which are capable of activating or inhibiting the PTPase enzymatic activity, and thereby affecting major pathways of cellular metabolism. By attaching an intact RPTPβ, or the ligand-binding portion thereof, to a solid phase matrix, an affinity probe is created which can be used to screen biological products or chemical agents for their capacity to interact with the receptor on the basis of their binding activity. Bound material can then be eluted from the affinity probe in purified form.

Methods for coupling proteins and peptides to the solid phase, the solid phase substances useful in these methods, and means for elution, are well known to those of skill in the art.

The RPTPβ protein or derivatives thereof having enzymatic activity can be used for testing of compounds capable of enhancing or inhibiting the phosphatase activity. The ability of a compound under test to modify phosphatase activity can be tested in an in vitro system wherein the test compound is added to purified RPTPβ protein, or an enzymatically active derivative thereof, and the affects on enzyme activity measured using standard enzymological procedures well known to those of skill in the art.

Alternatively, the action of a compound on RPTPβ enzymatic activity can be measured in a whole cell preparation using live or fixed cells, or a membrane fraction derived from live or fixed cells. This method is useful for screening compounds acting via the extracellular receptor portion of the protein, as well as compounds acting directly on the enzymatic portion of the protein. A test compound is incubated with cells, or with a membrane preparation derived therefrom, which express high amounts of the RPTPβ, such as transfected COS or NIH-3T3 cells. The amount of cellular phosphotyrosine is then measured, using methods well-known in the art (Honegger, A. M. et al., *Cell* 51:199–209 (1987); Margolis, B. et al., *Cell* 57:1101–1107 (1989)). The results are compared to results obtained in the absence of the test compound, or in the absence or presence of a known activator of RPTPβ enzymatic. In such studies, the action of the test compound in the presence of an activator of tyrosine kinase can also be measured. A compound which stimulates RPTPβ enzymatic activity will result in a net decrease in the amount of phosphotyrosine, whereas a compound which inhibits RPTPβ enzymatic activity will result in a net increase in the amount of phosphotyrosine.

In the case of growth factor receptors which are tyrosine kinases, such as the receptors for epidermal growth factor (EGF) and for platelet-derived growth factor (PDGF), tyrosine phosphorylation is linked to cell growth and to oncogenic transformation. Activation of a PTPase, leading to dephosphorylation, would serve as a counterregulatory mechanism to prevent or inhibit growth, and might serve as an endogenous regulatory mechanism against cancer. Thus, mutation or dysregulation of this receptor/enzyme system may promote susceptibility to cancer.

The insulin receptor is also a tyrosine kinase, and phosphorylation of tyrosine in cells bearing insulin receptors would be associated with normal physiological function. In contrast to the case of cell growth and cancer, activation of an RPTP would counteract insulin effects. Subnormal RPTP levels or enzymatic activity would act to remove a normal counterregulatory mechanisms. Perhaps more important, though, over-activity, or inappropriate activation, of an RPTP such as RPTPβ would be expected to partially or totally inhibit the action of insulin on cells, leading to diabetes (of an insulin-resistant variety). Thus, susceptibility to diabetes may be associated with RPTPβ dysregulation.

Therefore, the methods of the present invention for identifying normal or mutant RPTPβ genes, or for measuring the amount or activity of RPTPβ associated with a cell or tissue, can serve as methods for identifying susceptibility to cancer, diabetes, or other diseases associated with alterations in cellular phosphotyrosine metabolism.

The present invention provides methods for evaluating the presence of, and the level of, normal or mutant RPTPβ in a cell or in a subject. Absence, or more typically, low expression of RPTPβ, or presence of a mutant RPTPβ, in an individual may serve as an important predictor of susceptibility to oncogenic transformation and the development of cancer. Alternatively, over-expression of RPTPβ, possibly due to a mutant receptor/enzyme system insensitive to negative regulation, or due to overabundance of a stimulatory ligand in the body, may serve as an important predictor of susceptibility to diabetes.

An oligonucleotide probe encoding a part of the RPTPβ sequence (see below) is used to test cells from a subject for the presence DNA or RNA sequences encoding the RPTPβ. A preferred probe would be one directed to the nucleic acid sequence encoding at least 4 amino acid residues, and preferably at least 5 amino acid residues, of the RPTPβ. Qualitative or quantitative assays can be performed using such probes. For example, Northern analysis (see Sections 8 and 10 below) is used to measure expression of an RPTPβ mRNA in a cell or tissue preparation.

Such methods can be used even with very small amounts of DNA obtained from an individual, following use of selective amplification techniques. Recombinant DNA methodologies capable of amplifying purified nucleic acid fragments have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Sambrook et al. *Molecular Cloning: A Laboratory Manual*, Second Edition, Cold Spring Harbor Press, Cold Spring Harbor, N.Y. (1989), which references are herein incorporated by reference).

An in vitro, enzymatic method which is capable of increasing the concentration of such desired nucleic acid molecules is called the "polymerase chain reaction or "PCR" (Mullis, K. et al., *Cold Spring Harbor Symp. Quant. Biol.* 51:263–273 (1986); Erlich, H. et al., EP 50,424; EP 84,796, EP 258,017, EP 237,362; Mullis, K., EP 201,184; Mullis, K. et al., U.S. Pat. No. 4,683,202; Erlich, H., U.S. Pat. No. 4,582,788; and Saiki, R. et al., U.S. Pat. No. 4,683,194).

The PCR provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotide probes to serve as primers for the template-dependent, polymerase mediated replication of a desired nucleic acid molecule.

The precise nature of the two oligonucleotide probes of the PCR method is critical to the success of the method. Polymerase dependent amplification of a nucleic acid molecule proceeds by the addition of a 5' nucleotide triphosphate to the 3' hydroxyl end of a nucleic acid molecule. Thus, the action of a polymerase extends the 3' end of a nucleic acid molecule. These inherent properties are exploited in the selection of the oligonucleotide probes of the PCR. The oligonucleotide sequences of the probes of the PCR method are selected such that they contain sequences identical to, or complementary to, sequences which flank the particular nucleic acid sequence whose amplification is desired. More specifically, the oligonucleotide sequences of the "first" probe is selected such that it is capable of hybridizing to an oligonucleotide sequence located 3' to the desired sequence, whereas the oligonucleotide sequence of the "second" probe is selected such that it contains an oligonucleotide sequence identical to one present 5' to the desired region. Both probes possess 3' hydroxy groups, and therefore can serve as primers for nucleic acid synthesis.

PCR reaction conditions are cycled between (a) those conducive to hybridization and nucleic acid polymerization, and (b) those which result in the denaturation of duplex molecules. In the first step of the reaction, the nucleic acids of the sample are transiently heated, and then cooled, in order to denature any double-stranded molecules which may be present. The "first" and "second" probes are then added to the sample at a concentration which greatly exceeds that of the desired nucleic acid molecule. When the sample is incubated under conditions conducive to hybridization and polymerization, the "first" probe will hybridize to the nucleic acid molecule of the sample at a position 3' to the sequence to be amplified. If the nucleic acid molecule of the sample was initially double-stranded, the "second" probe will hybridize to the complementary strand of the nucleic acid molecule at a position 3' to the sequence which is the complement of the sequence whose amplification is desired. Upon addition of a polymerase, the 3' ends of the "first" and (if the nucleic acid molecule was double-stranded) "second" probes will be extended. The extension of the "first" probe will result in the synthesis of an oligonucleotide having the exact sequence of the desired nucleic acid. Extension of the "second" probe will result in the synthesis of an oligonucleotide having the exact sequence of the complement of the desired nucleic acid.

The PCR reaction is capable of exponential amplification of specific nucleic acid sequences because the extension product of the "first" probe, of necessity, contains a sequence which is complementary to a sequence of the "second" probe, and thus can serve as a template for the production of an extension product of the "second" probe. Similarly, the extension product of the "second" probe, of necessity, contains a sequence which is complementary to a sequence of the "first" probe, and thus can serve as a template for the production of an extension product of the "first" probe. Thus, by permitting cycles of polymerization, and denaturation, a geometric increase in the concentration of the desired nucleic acid molecule can be achieved. Reviews of the PCR are provided by Mullis, K. B. (*Cold Spring Harbor Symp. Quant. Biol.* 51:263–273 (1986)); Saiki, R. K., et al. (*Bio/Technology* 3:1008–1012 (1985)); and Mullis, K. B., et al. (*Meth. Enzymol.* 155:335–350 (1987)).

In one embodiment, the present invention is directed to a naturally occurring mammalian RPTPβ. In another embodiment, the invention is directed to a recombinant mammalian RPTPβ. The preferred mammalian RPTPβ of the present invention is of human origin. The invention provides the naturally occurring molecule substantially free of other proteins with which it is natively associated. "Substantially free of other proteins or glycoproteins" indicates that the protein has been purified away from at least 90 percent (on a weight basis), and from even at least 99 percent if desired, of other proteins and glycoproteins with which it is natively associated, and is therefore substantially free of them. That can be achieved by subjecting the cells, tissue or fluid containing the RPTPβ to standard protein purification techniques such as immunoabsorbent columns bearing an antibody specific for the protein. Other forms of affinity purification can utilize solid-phase substrates which can bind the PTPase domain, or a ligand that will bind to the receptor domain. Alternatively, the purification can be achieved by a combination of standard methods, such as ammonium sulfate precipitation, molecular sieve chromatography, and ion exchange chromatography.

It will be understood that the RPTPβ of the present invention can be biochemically purified from a variety of cell or tissue sources. For preparation of naturally occurring RPTPβ, tissues such as mammalian brain, especially of human origin, are preferred.

Alternatively, because the gene for the RPTPβ can be isolated or synthesized, the polypeptide can be synthesized substantially free of other proteins or glycoproteins of mammalian origin in a prokaryotic organism or in a non-mammalian eukaryotic organism, if desired. As intended by the present invention, a recombinant RPTPβ molecule produced in mammalian cells, such as transfected COS, NIH-3T3, or CHO cells, for example, is a protein with a naturally occurring amino acid sequence or is a functional derivative thereof. Where a naturally occurring protein or glycoprotein is produced by recombinant means, it is provided substantially free of the other proteins and glycoproteins with which it is natively associated.

Alternatively, methods are well known for the synthesis of polypeptides of desired sequence on solid phase supports and their subsequent separation from the support.

In a further embodiment, the invention provides "functional derivatives" of the RPTPβ. By "functional derivative" is meant a "fragment," "variant," "analog," or "chemical derivative" of RPTPβ, which terms are defined below. A function al derivative retains at least a portion of the function of the RPTPβ, such as (a) binding to a specific antibody, (b) phosphatase enzymatic activity or (c) binding of the extracellular "receptor" domain to a ligand, which permits its utility in accordance with the present invention.

A "fragment" of the RPTPβ refers to any subset of the molecule, that is, a shorter peptide.

A "variant" of the RPTPβ refers to a molecule substantially similar to either the entire peptide or a fragment thereof. Variant peptides may be conveniently prepared by direct chemical synthesis of the variant peptide, using methods well-known in the art.

Alternatively, amino acid sequence variants of the peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure (see European Patent Publication No. EP 75,444).

At the genetic level, these variants ordinarily are prepared by site-directed mutagenesis (as exemplified by Adelman et al., DNA 2:183 (1983)) of nucleotides in the DNA encoding the peptide molecule, thereby producing DNA encoding the variant, and thereafter expressing the DNA in recombinant cell culture. The variants typically exhibit the same qualitative biological activity as the nonvariant peptide.

An "analog" of the RPTPβ refers to a non-natural molecule substantially similar to either the entire molecule or a fragment thereof.

A "chemical derivative" of the RPTPβ contains additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2chloromercuri-4-nitrophenol, or chloro-7-nitrobenzo-2-oxa-1,3-diazole.

Histidyl residues are derivatized by reaction with diethylprocarbonate, pH 5.5–7.0, because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3- butanedione, 1,2-cyclohexanedione, and ninhydrin. Derivatization of arginine residues requires that the reaction be performed in alkaline conditions because of the high $PK_a$ of the guanidine functional group. Furthermore, these reagents may react with the groups of lysine as well as the arginine ε-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides (R'—N—C—N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues may be deamidated to the corresponding glutamyl and aspartyl residues, under mildly acidic conditions. Either form of these residues falls within the scope of this invention.

Derivatization with bifunctional agents is useful for crosslinking the protein or peptide to a water-insoluble support matrix or to other macromolecular carriers. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'- dithiobis(succinimidyl-propionate), and bifunctional maleimides such as bis-N-maleimido-1,8-octane. Derivatizing agents such as methyl-3-[(p-azidophenyl) dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691, 016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the X-amino groups of lysine, arginine, and histidine side chains (T. E. Creighton, *Proteins: Structure and Molecule Properties*, W. H. Freeman & Co., San Francisco, pp. 79–86 (1983)), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *Remington's Pharmaceutical Sciences*, 16th ed., Mack Publishing Co., Easton, Pa. (1980)

This invention is also directed to an antibody specific for an epitope of RPTPβ, preferably, of human RPTPβ, and the use of such antibody to detect the presence of, or measure the quantity or concentration of, the RPTPβ in a cell, a cell or tissue extract, or a biological fluid.

The term "antibody" is meant to include polyclonal antibodies, monoclonal antibodies (mAbs), chimeric antibodies, and anti-idiotypic (anti-Id) antibodies.

Polyclonal antibodies are heterogeneous populations of antibody molecules derived from the sera of animals immunized with an antigen.

Monoclonal antibodies are a substantially homogeneous population of antibodies to specific antigens. MAbs may be obtained by methods known to those skilled in the art. See, for example Kohler and Milstein, *Nature* 256:495–497 (1975) and U.S. Pat. No. 4,376,110. Such antibodies may be of any immunoglobulin class including IgG, IgM, IgE, IgA, and any subclass thereof. The hybridoma producing the mAbs of this invention may be cultivated in vitro or in vivo. Production of high titers of mAbs in vivo production makes this the presently preferred method of production. Briefly, cells from the individual hybridomas are injected intraperitoneally into pristane-primed BALB/c mice to produce ascites fluid containing high concentrations of the desired mAbs. MAbs of isotype IgM or IgG may be purified from such ascites fluids, or from culture supernatants, using column chromatography methods well known to those of skill in the art.

Chimeric antibodies are molecules different portions of which are derived from different animal species, such as those having variable region derived from a murine mAb and a human immunoglobulin constant region. Chimeric antibodies and methods for their production are known in the art (Cabilly et al, *Proc. Natl. Acad. Sci. USA* 81:3273–3277 (1984); Morrison et al., *Proc. Natl. Acad. Sci. USA* 81:6851–6855 (1984); Boulianne et al., *Nature* 312:643–646 (1984); Neuberger et al., *Nature* 314:268–270 (1985); Taniguchi et al., European Patent Application 171496 (published Feb. 19, 1985); Morrison et al., European Patent Application 173494 (published Mar. 5, 1986); Neuberger et al., PCT Application WO 86/01533 (published Mar. 13, 1986); Kudo et al., European Patent Application 184187 (published Jun. 11, 1986); Morrison et al., European Patent Application 173494 (published Mar. 5, 1986); Sahagan et al., J. Immunol. 137:1066–1074 (1986); Robinson et al., International Patent Publication #PCT/US86/02269 (published May 7, 1987); Liu et al., *Proc. Natl. Acad. Sci. USA* 84:3439–3443 (1987); Sun et al., *Proc. Natl. Acad. Sci. USA* 84:214–218 (1987); Better et al., *Science* 240:1041–1043 (1988)). These references are hereby incorporated by reference.

An anti-idiotypic (anti-Id) antibody is an antibody which recognizes unique determinants generally associated with the antigen-binding site of an antibody. An anti-Id antibody can be prepared by immunizing an animal of the same species and genetic type (e.g. mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other hybrid clones expressing antibodies of identical specificity.

Accordingly, mAbs generated against RPTPβ may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for an RPTPβ epitope.

The anti-Id mAbs thus have their own idiotypic epitopes, or "idiotopes" structurally similar to the epitope being evaluated, such as an epitope of RPTPβ.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')$_2$ and other fragments of the antibodies useful in the present invention may be used for the detection and quantitation of RPTPβ according to the methods disclosed herein for intact antibody molecules. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics. An "antigen" is a molecule or a portion of a molecule capable of being bound by an antibody which is additionally capable of inducing an animal to produce antibody capable of binding to an epitope of that antigen. An antigen may have one, or more than one epitope.

An antibody is said to be specific for an antigen because it reacts in a highly selective manner, with that antigen and not with the multitude of other antigens which are structurally distinct.

The antibodies, or fragments of antibodies, useful in the present invention may be used to quantitatively or qualitatively detect the presence of cells which express the RPTPβ protein. This can be accomplished by immunofluorescence techniques employing a fluorescently labeled antibody (see below) coupled with light microscopic, flow cytometric, or fluorimetric detection. For such methods, the antibody is preferably specific for an extracellular epitopic of RPTPβ.

The antibodies (or fragments thereof) useful in the present invention may be employed histologically, as in immunofluorescence or immunoelectron microscopy, for in situ detection of RPTP. In situ detection may be accomplished by removing a histological specimen from a patient, and providing the a labeled antibody of the present invention to such a specimen. The antibody (or fragment) is preferably provided by applying or by overlaying the labeled antibody (or fragment) to a biological sample. Through the use of such a procedure, it is possible to determine not only the presence of the RPTPβ but also its distribution on the examined tissue. Using the present invention, those of ordinary skill will readily perceive that any of a wide variety of histological methods (such as staining procedures) can be modified in order to achieve such in situ detection. Such assays for RPTPβ typically comprise incubating a biological sample, such as a biological fluid, a tissue extract, freshly harvested cells such as lymphocytes or leucocytes, or cells which have been incubated in tissue culture, in the presence of a detectably labeled antibody specific for RPTPβ, and detecting the antibody by any of a number of techniques well-known in the art.

The biological sample may be treated with a solid phase support or carrier such as nitrocellulose, or other solid support which is capable of immobilizing cells, cell particles or soluble proteins. The support may then be washed with suitable buffers followed by treatment with the detectably labeled RPTPβ-specific antibody. The solid phase support may then be washed with the buffer a second time to remove unbound antibody. The amount of bound label on said solid support may then be detected by conventional means.

By "solid phase support" is intended any support capable of binding antigen or antibodies. Well-known supports, or carriers, include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-RPTPβ antibody may be determined according to well-known methods. Those skilled in the art will be able to determine operative and optimal assay conditions for each determination by employing routine experimentation.

One of the ways in which the RPTPβ-specific antibody can be detectably labeled is by linking the antibody, or linking a second antibody which binds to the anti-RPTPγ antibody, to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactively labeling the antibodies or antibody fragments, it is possible to detect R-PTPase through the use of a radioimmunoassay (RIA) (see, for example, Work, T. S. et al., *Laboratory Techniques and Biochemistry in Molecular Biology*, North Holland Publishing Company, New York, 1978, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The antibody molecules of the present invention may be adapted for utilization in an immunometric assay, also known as a "two-site" or "sandwich" assay. In a typical immunometric assay, a quantity of unlabeled antibody (or fragment of antibody) is bound to a solid support and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support through the unlabeled antibody, the solid support is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncompleted labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

The presence of normally functioning RPTPβ in a subject can also be tested using direct enzymatic assays, for the tyrosine phosphatase activity. Such biochemical measurements can be performed in vitro, using purified enzymes, allowing precise measurements of enzyme activity, or with membrane preparations, or whole cells, where the net phosphotyrosine level is determined.

In additional embodiments of the present invention, a nucleic acid molecule, preferably DNA, comprising a sequence encoding an RPTPβ protein molecule and methods for expressing the DNA sequence are provided. One of ordinary skill in the art will know how to identify and clone additional PTPase molecules, of human or other mammalian species, which have sequence homology to the RPTPβ molecules described herein, using the genetic sequences and oligonucleotides of the present invention without undue experimentation. Furthermore, manipulation of the genetic constructs of the present invention allow the grafting of a particular ligand-binding receptor domain onto the transmembrane and catalytic portions of the RPTPβ resulting in chimeric molecules. Non-limiting examples of such chimeric molecules include the RPTPβ wherein the receptor is an epidermal growth factor receptor, a fibroblast growth factor receptor, and the like. Genetically engineered chimeric receptors are known in the art (see, for example, Riedel, H. et al., Nature 324:628–670 (1986)).

Genetic constructs encoding RPTPβ, functional derivative thereof, and chimeric molecules such as those described above, can be used in gene therapy. An abnormal or dysfunctional RPTPβ, which results in disease, may be replaced by infusion of cells of the desired lineage (such as hemopoietic cells, neurons, etc.) transfected with DNA encoding normal RPTPβ. Alternatively, or additionally, cells carrying a chimeric RPTPβ having a receptor to a ligand of choice (e.g., EGF) can be used for such gene therapy.

The recombinant DNA molecules of the present invention can be produced through any of a variety of means, such as, for example, DNA or RNA synthesis, or more preferably, by application of recombinant DNA techniques. Techniques for synthesizing such molecules are disclosed by, for example, Wu, R., et al. (*Prog. Nucl. Acid. Res. Molec. Biol.* 21:101–141 (1978)). Procedures for constructing recombinant molecules in accordance with the above-described method are disclosed by Sambrook et al. (supra).

Oligonucleotides representing a portion of an RPTPβ are useful for screening for the presence of genes encoding such proteins and for the cloning of an RPTPβ gene. Techniques for synthesizing such oligonucleotides are disclosed by, for example, Wu et al., supra).

Protein molecules are fragmented as with cyanogen bromide, or with proteases such as papain, chymotrypsin, trypsin, etc. (Oike, Y., et al., *J. Biol. Chem.* 257:9751–9758 (1982); Liu, C., et al., *Int. J. Pept. Protein Res.* 21:209–215 (1983)). Because the genetic code is degenerate, more than one codon may be used to encode a particular amino acid (Watson, J. D., In: *Molecular Biology of the Gene*, 4th Ed., Benjamin/Cummings Publishing Co., Inc., Menlo Park, Calif. (1987)). Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic cells. Such "codon usage rules" are disclosed by Lathe, R., et al.,*J. Molec. Biol.* 183:1–12 (1985). Using such "codon usage rules", a single oligonucleotide, or a set of oligonucleotides, that contains a theoretical "most probable" nucleotide sequence capable of encoding RPTPβ is identified.

Although occasionally an amino acid sequence may be encoded by only a single oligonucleotide, frequently the amino acid sequence may be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the RPTPβ.

The oligonucleotide, or set of oligonucleotides, containing the theoretical "most probable" sequence capable of encoding the RPTPβ fragment is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the RPTPβ gene (Sambrook et al., supra).

A suitable oligonucleotide, or set of oligonucleotides, which is capable of encoding a fragment of the RPTPβ gene (or complementary to such an oligonucleotide) is identified as above and synthesized, using procedures well known in the art (Belagaje, R., et al., *J. Biol. Chem.* 254:5765–5780 (1979); Maniatis, T., et al., In: *Molecular Mechanisms in the Control of Gene Expression*, Nierlich, D. P., et al., Eds., Acad. Press, N.Y. (1976); Wu, R., et al., *Prog. Nucl. Acid Res. Molec. Biol.* 21:101–141 (1978); Khorana, R. G., *Science* 203:614–625 (1979)). DNA synthesis may be achieved using an automated synthesizers. The oligonucleotide probe or set is hybridized by means well known in the art, against a DNA or, more preferably, a cDNA preparation derived from cells which are capable of expressing the RPTPβ gene. Techniques of nucleic acid hybridization are disclosed by Sambrook et al. (supra), and by, S Haymes, B. D., et al. (In: *Nucleic Acid Hybridization, A Practical Approach*, IRL Press, Washington, D.C. (1985)), which references are herein incorporated by reference. Techniques such as, or similar to, those described above have successfully enabled the cloning of genes for human aldehyde dehydrogenases (Hsu, L. C., et al., *Proc. Natl. Acad. Sci. USA* 82:3771–3775 (1985)), fibronectin (Suzuki, S., et al., *EMBO J.* 4:2519–2524 (1985)), the human estrogen receptor gene (Walter, P., et al., *Proc. Natl. Acad. Sci. USA* 82:7889–7893 (1985)), tissue-type plasminogen activator (Pennica, D., et al., *Nature* 301:214–221 (1983)) and human term placental alkaline phosphatase complementary DNA (Kam, W., et al., *Proc. Natl. Acad. Sci. USA* 82: (715–8719 (1985)).

In a alternative way of cloning the RPTPβ gene, a library of expression vectors is prepared by cloning DNA or, more preferably, cDNA (from a cell capable of expressing RPTPβ) into an expression vector. The library is then screened for members capable of expressing a protein which binds to anti-RPTPβ antibody, and which has a nucleotide sequence that is capable of encoding a polypeptide that has the same amino acid sequence as all or part of RPTPβ. In this embodiment, DNA, or more preferably cDNA, is extracted and purified from a cell which is capable of expressing RPTPβ protein. The purified cDNA is fragmented (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or cDNA fragment.

An "expression vector" is a vector which (due to the presence of appropriate transcriptional and/or translational control sequences) is capable of expressing a DNA molecule which has been cloned into the vector and of thereby producing a peptide or protein. Expression of the cloned sequences occurs when the expression vector is introduced into an appropriate host cell. If a prokaryotic expression vector is employed, then the appropriate host cell would be any prokaryotic cell capable of expressing the cloned sequences. If a eukaryotic expression vector is employed, then the appropriate host cell would be any eukaryotic cell capable of expressing the cloned sequences. Importantly, since eukaryotic DNA may contain intervening sequences, and since such sequences cannot be correctly processed in prokaryotic cells, it is preferable to employ cDNA from a cell which is capable of expressing RPTPγ in order to produce a prokaryotic genomic expression vector library. Procedures for preparing cDNA and for producing a genomic library are disclosed by Sambrook et al. (supra).

A DNA sequence encoding the RPTPβ of the present invention, or its functional derivatives, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Sambrook et al., supra, and are well known in the art.

A nucleic acid molecule, such as DNA, is said to be "capable of expressing" a polypeptide if it contains nucleotide sequences which contain transcriptional and translational regulatory information and such sequences are "operably linked" to a polypeptide coding sequence. An operable linkage is a linkage in which the regulatory DNA sequences and coding sequence are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the TATA box, capping sequence, CAAT sequence, and the like.

If desired, the non-coding region 3' to the coding sequence may be obtained by the above-described methods. This region may be retained for its transcriptional termination regulatory sequences, such as termination and polyadenylation. Thus, by retaining the 3'-region naturally contiguous to the DNA coding sequence, the transcriptional termination signals may be provided. Where the transcriptional termination signals are not satisfactorily functional in the desired host cell, then a 3' region functional in the host cell may be substituted.

Two DNA sequences (such as a promoter region sequence and a RPTPβ coding sequence) are said to be operably linked if the nature of the linkage between the two DNA sequences does not (1) result in the introduction of a frame-shift mutation, (2) interfere with the ability of the promoter to regulate direct the transcription of the RPTPβ coding sequence. A promoter region is operably linked to a DNA coding sequence if the promoter is capable of effecting transcription of the coding sequence. Thus, to express the protein, transcriptional and translational signals recognized by an appropriate host are necessary. In order to be "operably linked" it is not necessary that two sequences be immediately adjacent to one another.

A promoter is a double-stranded DNA (or RNA) molecule which is capable of binding to RNA polymerase and promoting the transcription of an "operably linked" nucleic acid coding sequence. As used herein, a "promoter sequence" is the sequence of the promoter which is found on that strand of the DNA (or RNA) which is transcribed by the RNA polymerase. A "promoter sequence complement" has a sequence which is the complement of the "promoter sequence." Hence, upon extension of a primer DNA or RNA adjacent to a single-stranded "promoter sequence complement" or, of a "promoter sequence," a double-stranded molecule is created which will contain a functional promoter, if that extension proceeds towards the "promoter sequence" or the "promoter sequence complement." This functional promoter will direct the transcription of a nucleic acid molecule which is operably linked to that strand of the double-stranded molecule which contains the "promoter sequence" (and not that strand of the molecule which contains the "promoter sequence complement").

Certain RNA polymerases exhibit a high specificity for such promoters. The RNA polymerases of the bacteriophages T7, T3, and SP-6 are especially well characterized, and exhibit high promoter specificity. The promoter sequences which are specific for each of these RNA polymerases also direct the polymerase to transcribe from only one strand of a duplex DNA template. Strand selection is determined by the orientation of the promoter sequence, and determines the direction of transcription since RNA is only polymerized enzymatically by the addition of a nucleotide 5' phosphate to a 3' hydroxyl terminus.

The promoter sequences of the present invention may be either prokaryotic, eukaryotic or viral. Suitable promoters are repressible, or, more preferably, constitutive. Examples of suitable prokaryotic promoters include promoters capable of recognizing the T4 (Malik, S. et al., *J. Biol. Chem.* 263:1174–1181 (1984); Rosenberg, A. H. et al., *Gene* 59:191–200 (1987); Shinedling, S. et al., *J. Molec. Biol.* 195:471–480 (1987); Hu, M. et al., *Gene* 42:21–30 (1986)), T3, Sp6, and T7 (Chamberlin, M. et al., *Nature* 228:227–231 (1970); Bailey, J. N. et al., *Proc. Natl. Acad. Sci. (U.S.A.)* 80:2814–2818 (1983); Davanloo, P. et al., *Proc. Natl. Acad. Sci. (U.S.A.)* 81:2035–2039 (1984)) polymerases; the $P_R$ and $P_L$ promoters of bacteriophage λ (The Bacteriophage Lambda, Hershey, A. D., Ed., Cold Spring Harbor Press, Cold Spring Harbor, N.Y. (1973); Lambda II, Hendrix, R. W., Ed., Cold Spring Harbor Press, Cold Spring Harbor, N.Y. (1980)); the trD, recA, heat shock, and lacZ promoters of *E. coli*; the α-amylase (Ulmanen, I., et al., *J. Bacteriol.* 162:176–182 (1985)) and the σ-28-specific promoters of *B. subtilis* (Gilman, M. Z., et al., *Gene* 32:11–20 (1984)); the promoters of the bacteriophages of Bacillus (Gryczan, T. J., In: *The Molecular Biology of the Bacilli*, Academic Press, Inc., N.Y. (1982)); Streptomyces promoters (Ward, J. M., et al., *Mol. Gen. Genet.* 203:468–478 (1986)); the int promoter of bacteriophage λ; the bla promoter of the β-lactamase gene of pBR322, and the CAT promoter of the chloramphenicol acetyl transferase gene of pPR325, etc. Prokaryotic promoters are reviewed by Glick, B. R. (*J. Ind. Microbiol.* 1:277–282 (1987)); Cenatiempo, Y. (*Biochimie* 68:505–516 (1986)); Watson, J. D. et al. (In: *Molecular Biology of the Gene*, Fourth Edition, Benjamin Cummins, Menlo Park, Calif. (1987)); and Gottesman, S. (*Ann. Rev. Genet.* 18:415–442 (1984)). Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature* (London) 290:304–310 (1981)); and the yeast gal4 gene promoter (Johnston, S. A., et al., *Proc. Natl. Acad. Sci. (USA)* 79:6971–6975 (1982); Silver, P. A., et al., *Proc. Natl. Acad. Sci. (USA)* 81:5951–5955 (1984)). All of the above listed references are incorporated by reference herein.

Strong promoters are preferred. Examples of such preferred promoters are those which recognize the T3, SP6 and T7 polymerases, the $P_L$ promoter of bacteriophage λ, the recA promoter and the promoter of the mouse metallothionein I gene. A most preferred promoter for eukaryotic expression of RPTP is an SV40 promoter such as that driving transcription in the pLSV vector (Livneh, E., et al., (1986) *J. Biol. Chem.* 261, 12490–12497). The sequences of such polymerase recognition sites are disclosed by Watson, J. D. et al. (In: *Molecular Biology of the Gene*, Fourth Edition, Benjamin/Cummings Publishing Co., Inc., Menlo Park, Calif., (1987)).

Having now generally described the invention, the same will be more readily understood through reference to the following example which is provided by way of illustration, and is not intended to be limiting of the present invention, unless specified.

6. EXAMPLE

ISOLATION AND CHARACTERIZATION OF HUMAN RPTPβ cDNA 6.1. MATERIALS

Restriction endonucleases and modifying enzymes were purchases from Boehringer-Mannheim or New England Biolabs. Taq DNA polymerase was from Perkin-Elmer/Cetus. The λgt11 forward and reverse primers (24-mers) used in the polymerase chain reactions as well as all sequencing primers, were synthesized on an automated DNA synthesizer (Applied Biosystems, model 380A) using either methoxy or β-cyanoethyl phosphoramidites (House, C., et al., *J. Biol. Chem.*, 262:772–777 (1987)). The λgt11 human brainstem cDNA library was obtained form the American Type Culture Collection (no. 37432). The LCA (CD45) clone used as a probe for screening the library was received from E. H. Fischer (University of Washington, Seattle). All sequencing reactions were performed using the Sequenase kit (United States Biochemical).

6.2. METHODS

A cDNA clone containing a portion of the coding sequences for RPTPβ was isolated after screening a λgt11 human infant brain stem cDNA library under conditions of reduced stringency with a nick translated LCA probe that included both phosphatase domains (Kaplan et al., *Proc. Natl. Acad. Sci. USA* 87:7000–7004 (1990)). Since the 5' end of this gene was not present in the original clone, the library was rescreened with a DNA fragment that was generated from the 5' end of the original clone. The probe was labeled with $^{32}$P-dCTP utilizing the random prime method (USB) and hybridization was performed under moderately stringent conditions at 42° C. in a buffer containing 50% formamide, 5×SSC, 20 mM Tris-HCl pH 7.6, 1× Denhardt's solution, 0.1% SDS and 100 μg/ml of sheared and denatured salmon sperm DNA. After hybridization, phage filters were washed three times for 20 min at 50° C. in a buffer containing 0.1×SSC/0.1% SDS and then were processed for autoradiography. The brainstem library was rescreened a total of three times in order to isolate overlapping cDNA clones that contained the entire coding sequence for RPTPβ.

cDNA inserts from positive recombinant plaque-purified phage were subcloned into the plasmid vector, BlueScript (Stratagene, La Jolla, Calif.), and sequenced by the dideoxy chain termination method using the Sequenase Version 2.0 Kit (USB).

6.3. RESULTS

The present inventors previously isolated a portion of a novel RPTP denoted RPTPβ (co-pending commonly assigned U.S. patent application Ser. No. 07/654,188, filed Feb. 26, 1991, from which the present application claims priority; Kaplan et al., 1990, supra). A similar phosphatase was independently cloned by another group and was termed called PTPζ (Krueger et al., 1990, supra; Krueger et al., 1992, supra). The reasons for the sequence differences between RPTPβ disclosed herein and PTPζ are not yet clear. Four overlapping cDNA clones containing the entire coding sequence for RPTPβ were isolated from a human brain stem library. The deduced amino acid sequence reveals an open reading frame of 2307 amino acids (FIGS. 2A–2B). RPTPβ belongs to the high molecular weight, transmembrane class of PTPases. The sequence contains a signal peptide (underlined in FIGS. 2A–2B) followed by a long extracellular domain of 1611 amino acids containing 21 potential N-glycosylation sites (indicated by arrows in FIG. 2A–2B). A hydrophobic, transmembrane peptide (bold sequences in FIG. 2A–2B) joins the extracellular portion of the protein to two tandemly repeated and conserved phosphatase domains (designated DI and DII). One distinguishing feature of this phosphatase is the homology it shares with different isoforms of carbonic anhydrase (CAH) over a stretch of 283 amino acids located at the extreme amino terminus of the protein (designated CAH in FIGS. 2A–2B). In addition to RPTPβ, the extracellular domain of a related RPTP, RPTPγ, shares homology with CAH (co-pending commonly assigned U.S. patent application Ser. No. 07/654,188, filed Feb. 26, 1991, from which the present application claims priority; co-pending commonly assigned U.S. patent application Ser. No. 08/015,986, filed May 10, 1993, titled "Novel Receptor-Type Phosphotyrosine Phosphatase-Gamma).

Alignment of the CAH-related domains of RPTPβ and RPTPγ with the six known isoforms of CAH is shown in FIGS. 3A–3C. FIG. 3D shows the percent similarity, taking into account conservative amino acid substitutions, between the CAH-related domain of RPTPβ, the corresponding domain of RPTPβ and the six CAH enzymes. The amino acid sequence similarity of the CAH-related domain of RPTPβ to the six CAH isoforms ranges from 45–50%. The highest degree of similarity (58%) exists between the CAH-related sequences of RPTPβ and RPTPγ. Therefore, RPTPβ and RPTPγ represent a new subgroup of RPTPs characterized by the presence of CAH-related regions in the amino terminal portions of their extracellular domains.

7. EXAMPLE

CHROMOSOMAL LOCALIZATION OF THE HUMAN RPTPβ GENE

7.1. METHODS

Isolation, propagation and characterization of parental and somatic cell hybrids used in this study have been described (Durst et al., Proc. Natl. Acad. Sci. USA 84:1070–1074 (1987); Huebner et al., Am. J. Hum. Genet. 48:726–740 (1991)). Presence of specific human chromosomes or regions of chromosomes has been confirmed by DNA hybridization using probes for genes assigned to specific chromosome regions. FIG. 4A depicts diagrammatically the chromosomes or partial chromosomes retained in most of the hybrids used.

Chromosomal in situ hybridization was performed as described (Cannizzaro et al., Cancer Res. 51:3818–3820 (1991)). Slides containing metaphase chromosomes from normal male (46 XY) peripheral blood lymphocytes were aged at 4° C. for 7–10 days and pretreated with ribonuclease A (Sigma) for 1 h at 37° C. The chromosomal DNA was denatured in a hybridization mixture containing 50% formamide, 2× SSC and 10% dextran sulfate (pH 7.0). Hybridization was carried out at 37° C. overnight. After rinsing at 39° C. in three changes of 50% formamide and 2× SSC, and five changes of 2× SSC, slides were dehydrated, air dried, subjected to autoradiography and banded with Wright's-Giemsa stain solution mixed with 1–3 parts of ph 9.2 borate buffer (Cannizzaro et al., supra).

7.2. RESULTS

The chromosomal localization of the human RPTPβ gene was initially determined utilizing a panel of rodent-human hybrids carrying defined human chromosomes or chromosome regions. The results from screening the rodent-human hybrids which are summarized-in FIG. 4A, correlates the presence of the human RPTPβ locus in hybrid cells with human chromosome 7. A more precise localization of the RPTPβf gene was determined by chromosomal in situ hybridization to metaphase chromosomes of normal human lymphocytes. This technique places the RPTPβ gene at 7q31–33 with the most likely position at 7q31.3–q32 which is diagrammatically shown to the right of the chromosome sketch in FIG. 4B.

8. EXAMPLE

EXPRESSION OF RPTPα RNA

8.1. ISOLATION OF MOUSE SEQUENCES HOMOLOGOUS TO HUMAN RPTPβ

Two oligonucleotides in conserved phosphatase domain II were synthesized according to the nucleotide sequence of human RPTPβ. These oligonucleotides in conjunction with phage DNA from a mouse brain cDNA library (Clonetech, Palo Alto, Calif.) were used in the PCR with Taq polymerase (Perkin-Elmer) to amplify homologous mouse RPTPβ sequences. The amplified product was purified and cloned into the BlueScript plasmid vector (Stratagene, La Jolla, Calif.). Homology was confirmed by DNA sequence analysis as described above. This subsoned fragment is called pBSMBDII.

8.2. NORTHERN ANALYSIS

Total cellular RNA was prepared with the Stratagene RNA isolation kit. Poly $A^+$ RNA was further selected utilizing oligo-dt cellulose chromatography (Stratagene). For Northern analysis, the RNA was separated on a 1.0% agarose/2.2M formaldehyde gel and transferred to a Nytran membrane (Schleicher and Schuell) by capillary action. The membrane was prehybridized and hybridized in 0.5M sodium phosphate ph 7.2, 7% SDS, 1 mM EDTA, 100 μg/ml salmon sperm DNA and then washed in 40 mM sodium phosphate ph 7.2, 1% SDS, 1 mM EDTA at 65° C. For the blot containing RNA isolated from various mouse tissues, a $^{32}P$-labeled probe was made utilizing PBSMBDII as template in the random primer labeling reaction (US Biochemicals). The human glioblastoma and neuroblastoma RNA blots were probed with labeled restriction fragments isolated from different parts of the human RPTPβ cDNA clones.

8.3. ANTIBODIES

A peptide derived from the carboxy-terminal 15 amino acids of human RPTPβ was synthesized and coupled to keyhole limpet hemocyanin according to standard procedures. Two rabbits were inoculated to produce polyclonal antisera against RPTPγ. Anti-EGF receptor immunoprecipitates were performed with RK2 antibody which recognizes the EGF receptor (Kris et al., Cell 40:619–625 (1985)).

8.4. CELL LABELING AND IMMUNOPRECIPITATION

The human neuroblastoma cell line, Lan 5, was maintained in Dulbecco's modified Eagle's medium (DMEM) containing 10% fetal bovine serum (FBS). Cultured cells were incubated with 10 μg/ml tunicamycin (Sigma Chemical Co.) for 1 hour prior to [$^{35}S$]-methionine labeling. Treated and untreated cells were washed twice with methionine free DMEM and labeled for 4 hours with 0.15 mCi/ml [$^{35}$S]-methionine (NEN, DuPont) in DMEM lacking methionine and supplemented with 1% dialyzed FBS. During the labeling period, 10 μg/ml tunicamycin-was added to the medium of the treated cells. Cells were then washed with ice cold phosphate buffered saline (PBS) and solubilized in a lysis buffer containing 50 mM N-2-hydroxyethylpiperazine-N'-2-ethanesulfonic acid (HEPES, pH 7.5), 150 mM NaCl, 1.0% Triton X-100, 10% glycerol, 1.5 mM MgCl$_2$, 1 mM ethylene glycol-bis [B-aminoethyl ether]-N,N,N', N'-tetraacetic acid (EGTA), 10 μg of leupeptin per ml, 1 mM phenylmethylsulfonyl fluoride, and 10 μg of aprotinin per ml. Cell lysates were clarified and then immunoprecipitated with normal rabbit serum, rabbit anti-RPTPβ antiserum or RK2 antiserum for 2 hour at 4° C. The immune complexes were precipitated with Protein A-Sepharose (Sigma Chemical Co.) for 45 min at 4° C. and washed 10 times with RIPA buffer (20 mM Tris-HCl, pH 7.6, 300 mM NaCl, 2 mM EDTA, 1.0% Triton X-100, 1.0% sodium deoxycholate and 0.1% SDS). The immunoprecipitated material was analyzed on a 7.5% SDS-polyacrylamide gel and fluorography.

5 8.5. RESULTS: DETECTION OF RPTPβ EXPRESSION IN A HUMAN NEUROBLASTOMA CELL LINE, Lan 5

Since all of the clones encoding the entire sequence for RPTPβ were isolated from a human brain stem library, the expression of RPTPβ mRNA was examined in different human glioblastoma cell lines and a human neuroblastoma cell line, Lan 5 (Sonnenfield et al., *J. Neurosci. Res.* 8:375–391 (1982)). A human RPTPβ probe hybridized to three major transcripts of 8.8, 7.5 and 6.4 kb, respectively (FIG. 5A). These transcripts were only detected in RNA isolated from the Lan 5 neuroblastoma cell line and were absent in the RNA isolated from the four glioblastoma cell lines even though similar amounts of total cellular RNA were loaded as revealed by ethidium bromide staining of the 28S and 18S ribosomal RNAs.

In order to obtain further insights into the nature of the three RPTPβ transcripts, performed an additional Northern analysis was performed on RNA isolated from Lan 5 cells with probes derived from nonconserved sequences in the extracellular domain of RPTPβ. An identical pattern of transcripts was revealed utilizing these probes.

The Lan 5 neuroblastoma cell line was used to study the endogenous expression of RPTPβ protein. Cell lysates prepared from cultures labeled with [$^{35}$S]methionine for 4 hours were immunoprecipitated with normal rabbit serum or anti-RPTPβ antiserum (FIG. 6). A protein with apparent molecular weight of approximately 300 kDa was recognized by the anti-RPTPβ antiserum but not by normal rabbit serum (lanes 1 and 2). Since there are 21 potential N-glycosylation sites, tunicamycin was employed to examine the possibility that the 300 kDa protein immunoprecipitated by the anti-RPTPβ antiserum was a glycosylated form of RPTPβ. The effects of tunicamycin treatment on the mobility of RPTPβ immunoprecipitated from [$^{35}$S]methionine-labeled cells was compared to its ability to inhibit the glycosylation of the EGF receptor which is also expressed in this cell line. Untreated cell lysates and lysates prepared from cells treated with tunicamycin were immunoprecipitated with an anti EGF receptor antibody (RK2) that recognizes the 170 kDa glycosylated and the 135 kDa nonglycosylated forms of the EGF receptor (Kris et al., supra). These results are also shown in FIG. 6, lanes 4 and 5. The protein immunoprecipitated with anti-RPTPβ antiserum from Lan 5 cells that had been metabolically labeled in the presence of tunicamycin (FIG. 6, lane 3) migrated with an apparent molecular weight of 250 kDa. This result was consistent with the predicted molecular weight of 254 kDa deduced from the amino acid sequence of RPTPβ.

9. EXAMPLE

IDENTIFICATION OF A VARIANT FORM OF RPTPβ

The overlapping human cDNA clones collectively contained approximately 8.1 kb of coding and noncoding sequences and appeared to represent the largest transcript that is 8.8 kb in length. In screening the human brain stem library and a human caudate library (Stratagene, La Jolla, Calif.), the present inventors isolated two independent cDNA clones that each contained an identical deletion of 2577 nucleotides from the extracellular domain of RPTPβ. This in-frame deletion joined amino acid 754 to amino acid 1614 (shown by the open arrows in FIGS. 2A–2B and in FIG. 7A) thereby maintaining the transmembrane domain and the two phosphatase domains. A deletion of this size could account for the difference between the 8.8 kb and 6.4 kb transcripts expressed in the Lan 5 neuroblastoma cell line (FIG. 5A). Hence, duplicate blots were made from RNA isolated from the Lan 5 cell line. One blot was analyzed with a probe that should hybridize to both the full length and deleted forms of RPTPγ (P1). The other blot was analyzed with a probe that should only hybridized to the full length form (P2). The location of probes 1 and 2 in the full length RPTPβ cDNA is shown in FIG. 7A. Northern analysis with the two probes shown in FIG. 7B revealed that probe 1 hybridized to the three distinct transcripts (P1) whereas probe 2 hybridized only to the 7.5 and 8.8 kb transcripts (P2). This result suggested that the 6.4 kb transcript represented a deleted variant form of RPTPβ which could be the result of alternative mRNA splicing. However, only the high molecular weight form of RPTPβ was detected following immunoprecipitation with anti RPTPβ antibodies and SDS-PAGE analysis (FIG. 6). The reason for the inability to detect the low molecular weight form in lysates from of RPTPβ in Lan5 cells is not clear.

10. EXAMPLE

TISSUE SPECIFIC EXPRESSION OF RPTPβ
10.1. METHODS: IN SITU HYBRIDIZATION ANALYSIS

Fresh frozen tissue was cut on a cryostat into 20 μm thick sections and thaw mounted onto gelatin coated slides. The sections were fixed in 4% paraformaldehyde in 0.1M sodium phosphate (pH 7.4) for 30 min and rinsed three time for 5 min each in 0. 1M sodium phosphate and once for 10 min in 2× SSC. Two probes were used in the hybridization analysis; (1) a 49 base oligonucleotide complementary to phosphatase domain II, and (2) a 50 base oligonucleotide complementary to the carbonic anhydrase-like domain. The oligonucleotides was labeled with [(α-$^{35}$S]dATP (NEN, DuPont) using terminal deoxynucleotidyl transferase (Boehringer Mannheim) and purified using Sephadex G25 quick spin columns (Boehringer Mannheim). The specific activity of the labeled probes was between 5×10$^8$ and 1×10$^9$ cpm/μg. Prehybridizations and hybridizations were carried out in a buffer containing 50% deionized formamide, 4× SSC, 1× Denhardt's, 500 μg/ml denatured salmon sperm DNA, 250 μg/ml yeast tRNA and 10% dextran sulfate. The tissue was incubated for 12 h at 45° C. in hybridization solution containing the labeled probe (1×10$^6$ cpm/section) and 10 mM dithiothreitol (DTT). Controls for specificity were performed on adjacent sections by diluting the labeled oligonucleotides with a 30-fold concentration of the appropriate unlabeled oligonucleotide and by hybridization with a sense probe. After hybridization, the sections were washed in 2 changes of 2× SSC at room temperature for 1 h, 1× SSC at 55° C. for 30 min, 0.5× SSC at 55° C. for 30 min, 0.5× SSC at room temperature for 15 min and dehydrated in 60%, 80%, and 100% ethanol. After air drying, the sections were exposed to X-ray film for 5–10 d.

10.2. RESULTS 10.2.1. Tissue Specific Expression of RPTPβ

Northern analysis of various tissue RNAs was performed to determine the tissue-specific expression of RPTPβ. The probe used in this analysis was a portion of the murine homolog of RPTPβ that was amplified in the PCR (described above) and contains 405 nucleotides encoding 135 amino acids of Domain II. Based on a nucleotide sequence comparison to the equivalent region of the human cDNA clone, the murine and human clones are 88% identical at the nucleotide level in this region of Domain II of RPTPβ. The results of this Northern analysis (FIG. 5B) indicated the presence of two major transcripts of 8.8 and 6.4 kb, respectively. These two transcripts are similar in size to the largest and smallest transcripts observed in Lan 5 RNA (see FIG. 5A). However, no band corresponding to the 7.5 kb transcript was detected. A minor transcript of approximately 9.4 kb was sometimes observed in RNA prepared from mouse brain tissue and may represent cross-reaction to a highly related phosphatase.

RPTPβ transcripts were not detected in the lung, heart, liver, spleen, kidney, muscle, testes and thymus. The quality of the RNA isolated from the various tissues was compared by parallel hybridization with an actin probe of the same blots (FIG. 5C). Hence, Northern hybridization analysis indicates that RPTPβ mRNA is strictly expressed in the brain of the adult mouse.

10.2.2. Localization of RPTPβ Expression in the Brain

In order to more precisely localize the expression of RPTPα in the brain, in situ hybridization was performed on brain tissue from the adult and the embryonic mouse. The results of this analysis confirmed that RPTPβ was expressed in the central nervous system. In a day 20 embryonic mouse (E20), a high level of expression was observed in the ventricular and subventricular zones of the brain (FIG. 8A), and in the spinal cord.

The level of expression was lower in the adult brain, and was localized to the Purkinje cell layer of the cerebellum, the dentate gyrus, and the subependymal layer of the anterior horn of lateral ventricle (FIG. 8B). Both probes (complementary to the CAH-like domain and the second phosphatase domain) gave identical results. The addition of a 30-fold excess of unlabeled oligonucleotide completely blocked the labeling in all areas. Furthermore, no signal was observed in adjacent sections hybridized with the sense probe, indicating that the probes hybridize to mRNA in a sequence specific manner.

These results demonstrated that RPTPβ has a restricted tissue specificity to specific regions of the nervous system.

11. GENERAL DISCUSSION FOR SECTIONS 6–10

The present inventor has cloned and characterized a human RPTP that is expressed in the central nervous system and cannot be detected in other murine tissues. Amino acid sequence analysis revealed that RPTPβ has a striking degree of sequence homology at it N-terminal end with various isoforms of the enzyme CAH over a stretch of 283 amino acids. RPTPγ was also found to contain a CAH-related sequence near the amino terminus in the extracellular domain. Therefore, RPTPβ and RPTPγ are concluded to be members of a new subgroup of transmembrane phosphatases that can be classified on the basis of a CAH-related domain present in the amino terminal regions of their extracellular domain.

A three dimensional model of the CAH-related domain of RPTPγ based upon the known crystal structure of CAH and a detailed description of this model was provided elsewhere by the present inventors laboratory (see, for example, co-pending commonly assigned U.S. patent application Ser. No. _____, filed May 10, 1993, titled "Novel Receptor-Type Phosphotyrosine Phosphatase-Gamma). Since key residues known to participate in the catalytic activity of CAH are missing from both RPTPβ (as well as from RPTPγ), it is likely that the CAH domains in these two phosphatases do not possess classical carbonic anhydrase activity.

It has been postulated that under-expression or inactivation of PTPases might lead to oncogenesis suggesting that PTPases may function as tumor suppressors. This finds support in the findings from the present inventor's laboratory that RPTPγ maps to human chromosome region 3p21, a region is frequently deleted in both renal cell and lung carcinomas (LaForgia et al., supra). The presently reported localization of the human RPTPβ gene to human chromosome 7q31.3–q32 renders it important to investigate loss of, or mutations in, the RPTPβ gene in certain tumor types, especially those exhibiting deletions of 7q.

In the case of the PTPase termed CD45, alternative mRNA splicing was shown to produce six distinct isoforms, as a result of the differential usage of three exons encoding sequences in the extracellular domain (Streuli et al., *J. Exp. Med.* 166:1548–1566 (1987); Streuli et al., *EMBO J.* 8:787–796 (1989)). Alternative splicing within the first catalytic domain of RPTPα has also been described (Matthews et al., *Proc. Natl. Acad. Sci. USA* 87:4444–4448 (1990)). The results of Northern blot analysis reveal the presence of multiple RPTPβ transcripts in both mouse brain and a human neuroblastoma cell line, Lan 5, that appear to either result from alternatively spliced transcripts or from highly related genes. The Northern blot analyses indicate that the 8.8 kb and the 6.4 kb transcripts are strictly expressed in the brain. Northern blot analysis described in FIGS. 5A–5C in conjunction with the analysis of two independently isolated cDNA clones suggest that the smallest transcript of 6.4 kb may result from a deletion of approximately 2.6 kb encoding a large portion of the extracellular domain of RPTPβ.

The importance of tyrosine phosphorylation in the control and regulation of specific neuronal processes is under intense investigation. It was demonstrated that tyrosine phosphorylation is enhanced at the time of synaptogenesis during development (Cudmore et al., *J. Neurochem.* 57:1240–1248 (1991); Girault et al., *Proc. Natl. Acad. Sci. USA* 89:2769–2773 (1992); Qu et al., *Neuron* 2:367–378 (1990)) and may play a role in synaptic plasticity in the adult (Girault et al., *J. Neurochem.* 58:518–528 (1992)). In addition, NGF and other neurotrophic factors mediate their effects on neuronal survival by binding to and activating receptors with tyrosine kinase activity (Cordon-Cardo et al., *Cell* 66:1–20 (1991); Kaplan et al., *Science* 252:554–557 (1991); Klein et al., *Cell* 65:189–197 (1991); Schlessinger, J. et al., *Neuron* 9:383–391 (1992). Stimulation of other growth factor receptors with tyrosine kinase activities have profound effects on survival and differentiation of cultured neurons (Aizenman et al., *Brain Res.* 406:32–42 (1987); Morrison et al., *Science* 238:72–75 (1987)) suggesting a potential role in normal neuronal development. Finally, several cytoplasmic tyrosine kinases including the products of the proto-oncogenes c-src and c-yes are expressed at high levels in specific regions of neurons of the adult brain (Pang et al., *Proc. Natl. Acad. Sci. USA* 85:762–7661988a; Pang et al., *Soc. Neurosci. Abstr.* 14:44.6 (1988); Maness et al., *Proc. Natl. Acad. Sci. USA* 85:5001–5005 (1988); Sudol et al., *Molec. Cell. Biol.* 9:4545–4549 (1989)).

RPTPβ represents the first cloned mammalian PTPase whose tissue specific expression is restricted to the nervous system. Several Drosophila RPTPs have been identified that are selectively expressed on central nervous system axons in the embryo (Tian et al., *Cell* 67:675–685 (1991); Yang et al., *Cell* 67:661–673 1991). The identification of brain-specific PTPases, such as RPTPβ, is an important initial step towards understanding the regulation of tyrosine phosphorylation by the PTPases in mammalian neural tissues. The relatively high level of RPTPβ expression in the embryonic central nervous system CNS suggests that it plays a role in the development of the nervous system. It is of note that the ventricular and subventricular zones are the primary sites of cell division in the developing brain (Altman et al., *Exp. Neurol.* 107:23–35 (1990). Interestingly, RPTPβ is expressed in the few regions of the adult brain that continue to show mitotic activity such as the dentate gyrus and the subependymal layer of the anterior horn of the lateral ventricle. Immunocytochemical techniques are being applied to determine the precise cellular distribution of RPTPβ protein and to help elucidate its role in the regulation of specific developmental and neuronal processes.

The sequences of the conserved phosphatase domains of the human RPTPβ, as described in detail above, is compared in Table I, below, with RPTPα and RPTPγ and with the sequences of LCA, LAR, and two soluble PTPases, placental phosphatase 1B and T-cell PTPase. The two soluble enzymes have a sequence identity of 70%; however, when each is compared with the RPTPs (Phosphatase domains PD1 or PD2, also referred to above as PDI and PDII), this number drops to 29–42%. In all cases, the soluble PTPases showed a greater identity with PD1 than with PD2 of the RPTPs. RPTPα appears to be most related to LAR, since their PD1 sequences are 56% identical and their PD2 sequences are 52% identical. The conserved domains of RPTPβ and RPTPγ are most related to each other, even more so than are the two soluble PTPases, β and γ being 75% identical in both PD1 and PD2. It is interesting that, in general, the sequence relationship between PD1 and PD2 within any RPTP appears to be no closer than that seen between different members of the family, i.e., the identities between PD1 and PD2 range from a high of 47% for LAR to a low of 29% for RPTP γ.

While the cytoplasmic domains of RPTPα, β, and γ are highly conserved, the extracellular domains of these receptors are unrelated to one another as well as to those of LAR and LCA. This suggests that each of these receptors has its own distinct ligand. It is likely that the binding of such ligands to the RPTPs plays a crucial role, together with growth factor receptors exhibiting PTKase activity, in the regulation of the level of tyrosine phosphorylation of targets proteins involved in signal transduction. The diversity of the RPTPs described herein reveals the existence of a multigene family. Greater understanding of structure-function relationships among these membrane receptors will provide important insights into the mechanisms involved in cell growth, differentiation, and oncogenesis.

Although the inventor does not intend to be bound by any particular theory, the high interspecies conservation of the catalytic domains of the various RPTPs indicates an important role for these receptors in cell growth control.

TABLE 4

Identities Between Conserved Phosphatase Domains (Percent)

| PTPase | PTPase 1B | T-cell PTPase | LCA PD1 | LCA PD2 | LAR PD1 | LAR PD2 | RPTPase-α PD1 | RPTPase-α PD2 | RPTPase-β PD1 | RPTPase-β PD2 | RPTPAse-γ PD1 | RPTPAse-γ PD2 |
|---|---|---|---|---|---|---|---|---|---|---|---|---|
| PTPase 1B | 100 | — | — | — | — | — | — | — | — | — | — | — |
| T-cell PTPase | 70 | 100 | — | — | — | — | — | — | — | — | — | — |
| LCA PD1 | 37 | 36 | 100 | — | — | — | — | — | — | — | — | — |
| LCA PD2 | 30 | 26 | 31 | 100 | — | — | — | — | — | — | — | — |
| LAR PD1 | 39 | 42 | 50 | 28 | 100 | — | — | — | — | — | — | — |
| LAR PD2 | 29 | 33 | 42 | 34 | 45 | 100 | — | — | — | — | — | — |
| R-PTPase-α PD1 | 36 | 38 | 50 | 32 | 56 | 45 | 100 | — | — | — | — | — |
| R-PTPase-α PD2 | 33 | 34 | 40 | 32 | 41 | 52 | 43 | 100 | — | — | — | — |
| R-PTPase-β PD1 | 35 | 39 | 41 | 31 | 33 | 41 | 47 | 33 | 100 | — | — | — |
| R-PTPase-β PD2 | 29 | 30 | 31 | 30 | 31 | 34 | 31 | 37 | 30 | 100 | — | — |
| R-PTPase-γ PD1 | 35 | 34 | 32 | 29 | 39 | 36 | 34 | 32 | 75 | 27 | 100 | — |
| R-PTPase-γ PD2 | 29 | 29 | 30 | 28 | 32 | 36 | 31 | 34 | 33 | 75 | 29 | 100 |

Alignments of the conserved phosphatase domains were carried out as described above. The regions compared are designated in FIG. 3C and FIGS. 5A–5C. PD = phosphatase domain.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

5,925,536

What is claimed is:

1. A method for identifying a compound that interacts with a polypeptide encoded by the nucleic acid molecule set forth in SEQ. ID NO:2, or a naturally occurring mammalian variant thereof, comprising:

(a) contacting the polypeptide with a compound for a time sufficient to allow interaction of the compound with the polypeptide;

(b) removing compound which has not interacted with the polypeptide; and (c) assaying for the presence of the compound, so that presence of the compound identifies a compound that interacts with the polypeptide.

2. The method of claim 1, wherein the polypeptide is a naturally occurring human polypeptide.

3. The method of claim 1, wherein the polypeptide comprises a polypeptide having the amino acid sequence depicted in SEQ. ID NO:1.

4. The method of claim 1, wherein the polypeptide comprises the ligand-binding portion of the polypeptide set forth in SEQ. ID NO:1, or a naturally occurring mammalian variant thereof.

5. The method of claim 1, wherein the polypeptide contains an amino acid sequence as depicted by amino acid residues 25–1653 of SEQ. ID NO:1.

6. The method of claim 1, wherein the polypeptide is a glycoprotein.

7. The method of claim 1, wherein the polypeptide is attached to a solid support.

8. A method for identifying an agent that modifies the enzymatic activity of a polypeptide encoded by the nucleic acid molecule set forth in SEQ. ID NO:2, or a naturally occurring mammalian variant thereof, comprising:

(a) contacting and incubating the agent with the polypeptide in pure form, in a membrane preparation, or in a whole cell; and
(b) comparing the enzymatic activity of the polypeptide in the incubated mixture of step (a) to that of the polypeptide incubated in the absence of agent, so that if there is a difference between the polypeptide enzymatic activity in the presence and absence of the agent, an agent which modifies the enzymatic activity of the polypeptide has been identified.

9. The method of claim 8 wherein the agent stimulates the polypeptide enzymatic activity.

10. The method of claim 8 wherein the agent inhibits the polypeptide enzymatic activity.

\* \* \* \* \*

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 2308 amino acids
      (B) TYPE: amino acid
      (D) TOPOLOGY: linear (ii) MOLECULE TYPE: protein (xi) SEQUENCE DESCRIPTION: SEQ ID NO:1:

```
Met Arg Ile Leu Lys Arg Phe Leu Ala Cys Ile Gln Leu Leu Cys Val
 1               5                  10                  15

Cys Arg Leu Asp Trp Ala Asn Gly Tyr Tyr Arg Gln Gln Arg Lys Leu
                20                  25                  30

Val Glu Glu Ile Gly Trp Ser Tyr Thr Gly Ala Leu Asn Gln Lys Asn
            35                  40                  45

Trp Gly Lys Lys Tyr Pro Thr Cys Asn Ser Pro Lys Gln Ser Pro Ile
        50                  55                  60

Asn Ile Asp Glu Asp Leu Thr Gln Val Asn Val Asn Leu Lys Lys Leu
65                  70                  75                  80

Lys Phe Gln Gly Trp Asp Lys Thr Ser Leu Glu Asn Thr Phe Ile His
                85                  90                  95

Asn Thr Gly Lys Thr Val Glu Ile Asn Leu Thr Asn Asp Tyr Arg Val
               100                 105                 110

Ser Gly Gly Val Ser Glu Met Val Phe Lys Ala Ser Lys Ile Thr Phe
               115                 120                 125

His Trp Gly Lys Cys Asn Met Ser Ser Asp Gly Ser Glu His Ser Leu
           130                 135                 140

Glu Gly Gln Lys Phe Pro Leu Glu Met Gln Ile Tyr Cys Phe Asp Ala
145                 150                 155                 160

Asp Arg Phe Ser Ser Phe Glu Glu Ala Val Lys Gly Lys Gly Lys Leu
                165                 170                 175

Arg Ala Leu Ser Ile Leu Phe Glu Val Gly Thr Glu Glu Asn Leu Asp
            180                 185                 190

Phe Lys Ala Ile Ile Asp Gly Val Glu Ser Val Ser Arg Phe Gly Lys
        195                 200                 205

Gln Ala Ala Leu Asp Pro Phe Ile Leu Leu Asn Leu Leu Pro Asn Ser
    210                 215                 220

Thr Asp Lys Tyr Tyr Ile Tyr Asn Gly Ser Leu Thr Ser Pro Pro Cys
225                 230                 235                 240

Thr Asp Thr Val Asp Trp Ile Val Phe Lys Asp Thr Val Ser Ile Ser
                245                 250                 255

Glu Ser Gln Leu Ala Val Phe Cys Glu Val Leu Thr Met Gln Gln Ser
            260                 265                 270

Gly Tyr Val Met Leu Met Asp Tyr Leu Gln Asn Asn Phe Arg Glu Gln
        275                 280                 285

Gln Tyr Lys Phe Ser Arg Gln Val Phe Ser Ser Tyr Thr Gly Lys Glu
    290                 295                 300

Glu Ile His Glu Ala Val Cys Ser Ser Glu Pro Glu Asn Val Gln Ala
305                 310                 315                 320

Asp Pro Glu Asn Tyr Thr Ser Leu Leu Val Thr Trp Glu Arg Pro Arg
```

```
                        325                 330                 335
Val Val Tyr Asp Thr Met Ile Glu Lys Phe Ala Val Leu Tyr Gln Gln
                340                 345                 350
Leu Asp Gly Glu Asp Gln Thr Lys His Glu Phe Leu Thr Asp Gly Tyr
        355                 360                 365
Gln Asp Leu Gly Ala Ile Leu Asn Asn Leu Leu Pro Asn Met Ser Tyr
    370                 375                 380
Val Leu Gln Ile Val Ala Ile Cys Thr Asn Gly Leu Tyr Gly Lys Tyr
385                 390                 395                 400
Ser Asp Gln Leu Ile Val Asp Met Pro Thr Asp Asn Pro Glu Leu Asp
                405                 410                 415
Leu Phe Pro Glu Leu Ile Gly Thr Glu Glu Ile Ile Lys Glu Glu Glu
                420                 425                 430
Glu Gly Lys Asp Ile Glu Glu Gly Ala Ile Val Asn Pro Gly Arg Asp
            435                 440                 445
Ser Ala Thr Asn Gln Ile Arg Lys Lys Glu Pro Gln Ile Ser Thr Thr
        450                 455                 460
Thr His Tyr Asn Arg Ile Gly Thr Lys Tyr Asn Glu Ala Lys Thr Asn
465                 470                 475                 480
Arg Ser Pro Thr Arg Gly Ser Glu Phe Ser Gly Lys Gly Asp Val Pro
                485                 490                 495
Asn Thr Ser Leu Asn Ser Thr Ser Gln Pro Val Thr Lys Leu Ala Thr
                500                 505                 510
Glu Lys Asp Ile Ser Leu Thr Ser Gln Thr Val Thr Glu Leu Pro Pro
            515                 520                 525
His Thr Val Glu Gly Thr Ser Ala Ser Leu Asn Asp Gly Ser Lys Thr
        530                 535                 540
Val Leu Arg Ser Pro His Met Asn Leu Ser Gly Thr Ala Glu Ser Leu
545                 550                 555                 560
Asn Thr Val Ser Ile Thr Glu Tyr Glu Glu Glu Ser Leu Leu Thr Ser
                565                 570                 575
Phe Lys Leu Asp Thr Gly Ala Glu Asp Ser Ser Gly Ser Ser Pro Ala
                580                 585                 590
Thr Ser Ala Ile Pro Phe Ile Ser Glu Asn Ile Ser Gln Gly Tyr Ile
            595                 600                 605
Phe Ser Ser Glu Asn Pro Glu Thr Ile Thr Tyr Asp Val Leu Ile Pro
        610                 615                 620
Glu Ser Ala Arg Asn Ala Ser Glu Asp Ser Thr Ser Ser Gly Ser Glu
625                 630                 635                 640
Glu Ser Leu Lys Asp Pro Ser Met Glu Gly Asn Val Trp Phe Pro Ser
                645                 650                 655
Ser Thr Asp Ile Thr Ala Gln Pro Asp Val Gly Ser Gly Arg Glu Ser
                660                 665                 670
Phe Leu Gln Thr Asn Tyr Thr Glu Ile Arg Val Asp Glu Ser Glu Lys
        675                 680                 685
Thr Thr Lys Ser Phe Ser Ala Gly Pro Val Met Ser Gln Gly Pro Ser
    690                 695                 700
Val Thr Asp Leu Glu Met Pro His Tyr Ser Thr Phe Ala Tyr Phe Pro
705                 710                 715                 720
Thr Glu Val Thr Pro His Ala Phe Thr Pro Ser Ser Arg Gln Gln Asp
                725                 730                 735
Leu Val Ser Thr Val Asn Val Val Tyr Ser Gln Thr Thr Gln Pro Val
                740                 745                 750
```

```
Tyr Asn Gly Glu Thr Pro Leu Gln Pro Ser Tyr Ser Ser Glu Val Phe
    755                 760                 765

Pro Leu Val Thr Pro Leu Leu Leu Asp Asn Gln Ile Leu Asn Thr Thr
    770                 775                 780

Pro Ala Ala Ser Ser Ser Asp Ser Ala Leu His Ala Thr Pro Val Phe
785                 790                 795                 800

Pro Ser Val Asp Val Ser Phe Glu Ser Ile Leu Ser Ser Tyr Asp Gly
                805                 810                 815

Ala Pro Leu Leu Pro Phe Ser Ala Ser Phe Ser Ser Glu Leu Phe
                820                 825                 830

Arg His Leu His Thr Val Ser Gln Ile Leu Pro Gln Val Thr Ser Ala
                835                 840                 845

Thr Glu Ser Asp Lys Val Pro Leu His Ala Ser Leu Pro Val Ala Gly
    850                 855                 860

Gly Asp Leu Leu Glu Pro Ser Leu Ala Gln Tyr Ser Asp Val Leu
865                 870                 875                 880

Ser Thr Thr His Ala Ala Ser Lys Thr Leu Glu Phe Gly Ser Glu Ser
                885                 890                 895

Gly Val Leu Tyr Lys Thr Leu Met Phe Ser Gln Val Glu Pro Pro Ser
                900                 905                 910

Ser Asp Ala Met Met His Ala Arg Ser Ser Gly Pro Glu Pro Ser Tyr
                915                 920                 925

Ala Leu Ser Asp Asn Glu Gly Ser Gln His Ile Phe Thr Val Ser Tyr
    930                 935                 940

Ser Ser Ala Ile Pro Val His Asp Ser Val Gly Val Thr Tyr Gln Gly
945                 950                 955                 960

Ser Leu Phe Ser Gly Pro Ser His Ile Pro Ile Pro Lys Ser Ser Leu
                965                 970                 975

Ile Thr Pro Thr Ala Ser Leu Leu Gln Pro Thr His Ala Leu Ser Gly
                980                 985                 990

Asp Gly Glu Trp Ser Gly Ala Ser Ser Asp Ser Glu Phe Leu Leu Pro
                995                1000                1005

Asp Thr Asp Gly Leu Thr Ala Leu Asn Ile Ser Ser Pro Val Ser Val
    1010                1015                1020

Ala Glu Phe Thr Tyr Thr Thr Ser Val Phe Gly Asp Asp Asn Lys Ala
1025                1030                1035                1040

Leu Ser Lys Ser Glu Ile Ile Tyr Gly Asn Glu Thr Glu Leu Gln Ile
                1045                1050                1055

Pro Ser Phe Asn Glu Met Val Tyr Pro Ser Glu Ser Thr Val Met Pro
                1060                1065                1070

Asn Met Tyr Asp Asn Val Asn Lys Leu Asn Ala Ser Leu Gln Glu Thr
                1075                1080                1085

Ser Val Ser Ile Ser Ser Thr Lys Gly Met Phe Pro Gly Ser Leu Ala
    1090                1095                1100

His Thr Thr Thr Lys Val Phe Asp His Glu Ile Ser Gln Val Pro Glu
1105                1110                1115                1120

Asn Asn Phe Ser Val Gln Pro Thr His Thr Val Ser Gln Ala Ser Gly
                1125                1130                1135

Asp Thr Ser Leu Lys Pro Val Leu Ser Ala Asn Ser Glu Pro Ala Ser
                1140                1145                1150

Ser Asp Pro Ala Ser Ser Glu Met Leu Ser Pro Ser Thr Gln Leu Leu
                1155                1160                1165

Phe Tyr Glu Thr Ser Ala Ser Phe Ser Thr Glu Val Leu Leu Gln Pro
                1170                1175                1180
```

-continued

```
Ser Phe Gln Ala Ser Asp Val Asp Thr Leu Leu Lys Thr Val Leu Pro
1185                1190                1195                1200

Ala Val Pro Ser Asp Pro Ile Leu Val Glu Thr Pro Lys Val Asp Lys
            1205                1210                1215

Ile Ser Ser Thr Met Leu His Leu Ile Val Ser Asn Ser Ala Ser Ser
            1220                1225                1230

Glu Asn Met Leu His Ser Thr Ser Val Pro Val Phe Asp Val Ser Pro
            1235                1240                1245

Thr Ser His Met His Ser Ala Ser Leu Gln Gly Leu Thr Ile Ser Tyr
            1250                1255                1260

Ala Ser Glu Lys Tyr Glu Pro Val Leu Leu Lys Ser Glu Ser Ser His
1265                1270                1275                1280

Gln Val Val Pro Ser Leu Tyr Ser Asn Asp Glu Leu Phe Gln Thr Ala
                1285                1290                1295

Asn Leu Glu Ile Asn Gln Ala His Pro Pro Lys Gly Arg His Val Phe
            1300                1305                1310

Ala Thr Pro Val Leu Ser Ile Asp Glu Pro Leu Asn Thr Leu Ile Asn
            1315                1320                1325

Lys Leu Ile His Ser Asp Glu Ile Leu Thr Ser Thr Lys Ser Ser Val
            1330                1335                1340

Thr Gly Lys Val Phe Ala Gly Ile Pro Thr Val Ala Ser Asp Thr Phe
1345                1350                1355                1360

Val Ser Thr Asp His Ser Val Pro Ile Gly Asn Gly His Val Ala Ile
            1365                1370                1375

Thr Ala Val Ser Pro His Arg Asp Gly Ser Val Thr Ser Thr Lys Leu
            1380                1385                1390

Leu Phe Pro Ser Lys Ala Thr Ser Glu Leu Ser His Ser Ala Lys Ser
            1395                1400                1405

Asp Ala Gly Leu Val Gly Gly Gly Glu Asp Gly Asp Thr Asp Asp Asp
            1410                1415                1420

Gly Asp Asp Asp Asp Asp Asp Arg Gly Ser Asp Gly Leu Ser Ile His
1425                1430                1435                1440

Lys Cys Met Ser Cys Ser Ser Tyr Arg Glu Ser Gln Glu Lys Val Met
                1445                1450                1455

Asn Asp Ser Asp Thr His Glu Asn Ser Leu Met Asp Gln Asn Asn Pro
            1460                1465                1470

Ile Ser Tyr Ser Leu Ser Glu Asn Ser Glu Glu Asp Asn Arg Val Thr
            1475                1480                1485

Ser Val Ser Ser Asp Ser Gln Thr Gly Met Asp Arg Ser Pro Gly Lys
            1490                1495                1500

Ser Pro Ser Ala Asn Gly Leu Ser Gln Lys His Asn Asp Gly Lys Glu
1505                1510                1515                1520

Glu Asn Asp Ile Gln Thr Gly Ser Ala Leu Leu Pro Leu Ser Pro Glu
                1525                1530                1535

Ser Lys Ala Trp Ala Val Leu Thr Ser Asp Glu Glu Ser Gly Ser Gly
            1540                1545                1550

Gln Gly Thr Ser Asp Ser Leu Asn Glu Asn Glu Thr Ser Thr Asp Phe
            1555                1560                1565

Ser Phe Ala Asp Thr Asn Glu Lys Asp Ala Asp Gly Ile Leu Ala Ala
            1570                1575                1580

Gly Asp Ser Glu Ile Thr Pro Gly Phe Pro Gln Ser Pro Thr Ser Ser
1585                1590                1595                1600

Val Thr Ser Glu Asn Ser Glu Val Phe His Val Ser Glu Ala Glu Ala
```

-continued

```
                1605                1610                1615
Ser Asn Ser Ser His Glu Ser Arg Ile Gly Leu Ala Glu Gly Leu Glu
                    1620                1625                1630

Ser Glu Lys Lys Ala Val Ile Pro Leu Val Ile Val Ser Ala Leu Thr
                    1635                1640                1645

Phe Ile Cys Leu Val Val Leu Val Gly Ile Leu Ile Tyr Trp Arg Lys
                    1650                1655                1660

Cys Phe Gln Thr Ala His Phe Tyr Leu Glu Asp Ser Thr Ser Pro Arg
1665                1670                1675                1680

Val Ile Ser Thr Pro Pro Thr Pro Ile Phe Pro Ile Ser Asp Asp Val
                    1685                1690                1695

Gly Ala Ile Pro Ile Lys His Phe Pro Lys His Val Ala Asp Leu His
                    1700                1705                1710

Ala Ser Ser Gly Phe Thr Glu Glu Phe Glu Glu Val Gln Ser Cys Thr
                    1715                1720                1725

Val Asp Leu Gly Ile Thr Ala Asp Ser Ser Asn His Pro Asp Asn Lys
                    1730                1735                1740

His Lys Asn Arg Tyr Ile Asn Ile Val Ala Tyr Asp His Ser Arg Val
1745                1750                1755                1760

Lys Leu Ala Gln Leu Ala Glu Lys Asp Gly Lys Leu Thr Asp Tyr Ile
                    1765                1770                1775

Asn Ala Asn Tyr Val Asp Gly Tyr Asn Arg Pro Lys Ala Tyr Ile Ala
                    1780                1785                1790

Ala Gln Gly Pro Leu Lys Ser Thr Ala Glu Asp Phe Trp Arg Met Ile
                    1795                1800                1805

Trp Glu His Asn Val Glu Val Ile Val Met Ile Thr Asn Leu Val Glu
                    1810                1815                1820

Lys Gly Arg Arg Lys Cys Asp Gln Tyr Trp Pro Ala Asp Gly Ser Glu
1825                1830                1835                1840

Glu Tyr Gly Asn Phe Leu Val Thr Gln Lys Ser Val Gln Val Leu Ala
                    1845                1850                1855

Tyr Tyr Thr Val Arg Asn Phe Thr Leu Arg Asn Thr Lys Ile Lys Lys
                    1860                1865                1870

Gly Ser Gln Lys Gly Arg Pro Ser Gly Arg Val Val Thr Gln Tyr His
                    1875                1880                1885

Tyr Thr Gln Trp Pro Asp Met Gly Val Pro Glu Tyr Ser Leu Pro Val
                    1890                1895                1900

Leu Thr Phe Val Arg Lys Ala Ala Tyr Ala Lys Arg His Ala Val Gly
1905                1910                1915                1920

Pro Val Val Val His Cys Ser Ala Gly Val Gly Arg Thr Gly Thr Tyr
                    1925                1930                1935

Ile Val Leu Asp Ser Met Leu Gln Gln Ile Gln His Glu Gly Thr Val
                    1940                1945                1950

Asn Ile Phe Gly Phe Leu Lys His Ile Arg Ser Gln Arg Asn Tyr Leu
                    1955                1960                1965

Val Gln Thr Glu Glu Gln Tyr Val Phe Ile His Asp Thr Leu Val Glu
                    1970                1975                1980

Ala Ile Leu Ser Lys Glu Thr Glu Val Leu Asp Ser His Ile His Ala
1985                1990                1995                2000

Tyr Val Asn Ala Leu Leu Ile Pro Gly Pro Ala Gly Lys Thr Lys Leu
                    2005                2010                2015

Glu Lys Gln Phe Gln Leu Leu Ser Gln Ser Asn Ile Gln Gln Ser Asp
                    2020                2025                2030
```

```
Tyr Ser Ala Ala Leu Lys Gln Cys Asn Arg Glu Lys Asn Arg Thr Ser
        2035                2040                2045

Ser Ile Ile Pro Val Glu Arg Ser Arg Val Gly Ile Ser Ser Leu Ser
        2050                2055                2060

Gly Glu Gly Thr Asp Tyr Ile Asn Ala Ser Tyr Ile Met Gly Tyr Tyr
2065            2070                2075                2080

Gln Ser Asn Glu Phe Ile Ile Thr Gln His Pro Leu His Thr Ile
        2085                2090                2095

Lys Asp Phe Trp Arg Met Ile Trp Asp His Asn Ala Gln Leu Val Val
        2100                2105                2110

Met Ile Pro Asp Gly Gln Asn Met Ala Glu Asp Glu Phe Val Tyr Trp
        2115                2120                2125

Pro Asn Lys Asp Glu Pro Ile Asn Cys Glu Ser Phe Lys Val Thr Leu
        2130                2135                2140

Met Ala Glu Glu His Lys Cys Leu Ser Asn Glu Glu Lys Leu Ile Ile
2145            2150                2155                2160

Gln Asp Phe Ile Leu Glu Ala Thr Gln Asp Asp Tyr Val Leu Glu Val
        2165                2170                2175

Arg His Phe Gln Cys Pro Lys Trp Pro Asn Pro Asp Ser Pro Ile Ser
        2180                2185                2190

Lys Thr Phe Glu Leu Ile Ser Val Ile Lys Glu Glu Ala Ala Asn Arg
        2195                2200                2205

Asp Gly Pro Met Ile Val His Asp Glu His Gly Gly Val Thr Ala Gly
        2210                2215                2220

Thr Phe Cys Ala Leu Thr Thr Leu Met His Gln Leu Glu Lys Glu Asn
2225            2230                2235                2240

Ser Val Asp Val Tyr Gln Val Ala Lys Met Ile Asn Leu Met Arg Pro
        2245                2250                2255

Gly Val Phe Ala Asp Ile Glu Gln Tyr Gln Phe Leu Tyr Lys Val Ile
        2260                2265                2270

Leu Ser Leu Val Ser Thr Arg Gln Glu Glu Asn Pro Ser Thr Ser Leu
        2275                2280                2285

Asp Ser Asn Gly Ala Ala Leu Pro Asp Gly Asn Ile Ala Glu Ser Leu
        2290                2295                2300

Glu Ser Leu Val
2305

(2) INFORMATION FOR SEQ ID NO:2:

(i) SEQUENCE CHARACTERISTICS:
          (A) LENGTH: 6924 base pairs
          (B) TYPE: nucleic acid
          (C) STRANDEDNESS: double
          (D) TOPOLOGY: unknown (ii) MOLECULE TYPE: cDNA (ix) FEATURE:
          (A) NAME/KEY: CDS
          (B) LOCATION: 1..6924

(xi) SEQUENCE DESCRIPTION: SEQ ID NO:2:

ATG CGA ATC CTA AAG CGT TTC CTC GCT TGC ATT CAG CTC CTC TGT GTT      48
Met Arg Ile Leu Lys Arg Phe Leu Ala Cys Ile Gln Leu Leu Cys Val
1               5                   10                  15

TGC CGC CTG GAT TGG GCT AAT GGA TAC TAC AGA CAA CAG AGA AAA CTT      96
Cys Arg Leu Asp Trp Ala Asn Gly Tyr Tyr Arg Gln Gln Arg Lys Leu
                20                  25                  30

GTT GAA GAG ATT GGC TGG TCC TAT ACA GGA GCA CTG AAT CAA AAA AAT     144
```

-continued

| | | | | | | | | | | | | | | |
|---|---|---|---|---|---|---|---|---|---|---|---|---|---|---|
| Val | Glu | Glu | Ile | Gly | Trp | Ser | Tyr | Thr | Gly | Ala | Leu | Asn | Gln | Lys | Asn |
| | | 35 | | | | 40 | | | | 45 | | | | |

```
TGG GGA AAG AAA TAT CCA ACA TGT AAT AGC CCA AAA CAA TCT CCT ATC        192
Trp Gly Lys Lys Tyr Pro Thr Cys Asn Ser Pro Lys Gln Ser Pro Ile
    50              55              60

AAT ATT GAT GAA GAT CTT ACA CAA GTA AAT GTG AAT CTT AAG AAA CTT        240
Asn Ile Asp Glu Asp Leu Thr Gln Val Asn Val Asn Leu Lys Lys Leu
65              70              75              80

AAA TTT CAG GGT TGG GAT AAA ACA TCA TTG GAA AAC ACA TTC ATT CAT        288
Lys Phe Gln Gly Trp Asp Lys Thr Ser Leu Glu Asn Thr Phe Ile His
                85              90              95

AAC ACT GGG AAA ACA GTG GAA ATT AAT CTC ACT AAT GAC TAC CGT GTC        336
Asn Thr Gly Lys Thr Val Glu Ile Asn Leu Thr Asn Asp Tyr Arg Val
            100             105             110

AGC GGA GGA GTT TCA GAA ATG GTG TTT AAA GCA AGC AAG ATA ACT TTT        384
Ser Gly Gly Val Ser Glu Met Val Phe Lys Ala Ser Lys Ile Thr Phe
        115             120             125

CAC TGG GGA AAA TGC AAT ATG TCA TCT GAT GGA TCA GAG CAC AGT TTA        432
His Trp Gly Lys Cys Asn Met Ser Ser Asp Gly Ser Glu His Ser Leu
    130             135             140

GAA GGA CAA AAA TTT CCA CTT GAG ATG CAA ATC TAC TGC TTT GAT GCA        480
Glu Gly Gln Lys Phe Pro Leu Glu Met Gln Ile Tyr Cys Phe Asp Ala
145             150             155             160

GAC CGA TTT TCA AGT TTT GAG GAA GCA GTC AAA GGA AAA GGG AAG TTA        528
Asp Arg Phe Ser Ser Phe Glu Glu Ala Val Lys Gly Lys Gly Lys Leu
                165             170             175

AGA GCT TTA TCC ATT TTG TTT GAG GTT GGG ACA GAA GAA AAT TTG GAT        576
Arg Ala Leu Ser Ile Leu Phe Glu Val Gly Thr Glu Glu Asn Leu Asp
            180             185             190

TTC AAA GCG ATT ATT GAT GGA GTC GAA AGT GTT AGT CGT TTT GGG AAG        624
Phe Lys Ala Ile Ile Asp Gly Val Glu Ser Val Ser Arg Phe Gly Lys
        195             200             205

CAG GCT GCT TTA GAT CCA TTC ATA CTG TTG AAC CTT CTG CCA AAC TCA        672
Gln Ala Ala Leu Asp Pro Phe Ile Leu Leu Asn Leu Leu Pro Asn Ser
    210             215             220

ACT GAC AAG TAT TAC ATT TAC AAT GGC TCA TTG ACA TCT CCT CCC TGC        720
Thr Asp Lys Tyr Tyr Ile Tyr Asn Gly Ser Leu Thr Ser Pro Pro Cys
225             230             235             240

ACA GAC ACA GTT GAC TGG ATT GTT TTT AAA GAT ACA GTT AGC ATC TCT        768
Thr Asp Thr Val Asp Trp Ile Val Phe Lys Asp Thr Val Ser Ile Ser
                245             250             255

GAA AGC CAG TTG GCT GTT TTT TGT GAA GTT CTT ACA ATG CAA CAA TCT        816
Glu Ser Gln Leu Ala Val Phe Cys Glu Val Leu Thr Met Gln Gln Ser
            260             265             270

GGT TAT GTC ATG CTG ATG GAC TAC TTA CAA AAC AAT TTT CGA GAG CAA        864
Gly Tyr Val Met Leu Met Asp Tyr Leu Gln Asn Asn Phe Arg Glu Gln
        275             280             285

CAG TAC AAG TTC TCT AGA CAG GTG TTT TCC TCA TAC ACT GGA AAG GAA        912
Gln Tyr Lys Phe Ser Arg Gln Val Phe Ser Ser Tyr Thr Gly Lys Glu
    290             295             300

GAG ATT CAT GAA GCA GTT TGT AGT TCA GAA CCA GAA AAT GTT CAG GCT        960
Glu Ile His Glu Ala Val Cys Ser Ser Glu Pro Glu Asn Val Gln Ala
305             310             315             320

GAC CCA GAG AAT TAT ACC AGC CTT CTT GTT ACA TGG GAA AGA CCT CGA       1008
Asp Pro Glu Asn Tyr Thr Ser Leu Leu Val Thr Trp Glu Arg Pro Arg
                325             330             335

GTC GTT TAT GAT ACC ATG ATT GAG AAG TTT GCA GTT TTG TAC CAG CAG       1056
Val Val Tyr Asp Thr Met Ile Glu Lys Phe Ala Val Leu Tyr Gln Gln
            340             345             350

TTG GAT GGA GAG GAC CAA ACC AAG CAT GAA TTT TTG ACA GAT GGC TAT       1104
```

```
Leu Asp Gly Glu Asp Gln Thr Lys His Glu Phe Leu Thr Asp Gly Tyr
            355                 360                 365

CAA GAC TTG GGT GCT ATT CTC AAT AAT TTG CTA CCC AAT ATG AGT TAT    1152
Gln Asp Leu Gly Ala Ile Leu Asn Asn Leu Leu Pro Asn Met Ser Tyr
    370                 375                 380

GTT CTT CAG ATA GTA GCC ATA TGC ACT AAT GGC TTA TAT GGA AAA TAC    1200
Val Leu Gln Ile Val Ala Ile Cys Thr Asn Gly Leu Tyr Gly Lys Tyr
385                 390                 395                 400

AGC GAC CAA CTG ATT GTC GAC ATG CCT ACT GAT AAT CCT GAA CTT GAT    1248
Ser Asp Gln Leu Ile Val Asp Met Pro Thr Asp Asn Pro Glu Leu Asp
                405                 410                 415

CTT TTC CCT GAA TTA ATT GGA ACT GAA GAA ATA ATC AAG GAG GAG GAA    1296
Leu Phe Pro Glu Leu Ile Gly Thr Glu Glu Ile Ile Lys Glu Glu Glu
            420                 425                 430

GAG GGA AAA GAC ATT GAA GAA GGC GCT ATT GTG AAT CCT GGT AGA GAC    1344
Glu Gly Lys Asp Ile Glu Glu Gly Ala Ile Val Asn Pro Gly Arg Asp
        435                 440                 445

AGT GCT ACA AAC CAA ATC AGG AAA AAG GAA CCC CAG ATT TCT ACC ACA    1392
Ser Ala Thr Asn Gln Ile Arg Lys Lys Glu Pro Gln Ile Ser Thr Thr
    450                 455                 460

ACA CAC TAC AAT CGC ATA GGG ACG AAA TAC AAT GAA GCC AAG ACT AAC    1440
Thr His Tyr Asn Arg Ile Gly Thr Lys Tyr Asn Glu Ala Lys Thr Asn
465                 470                 475                 480

CGA TCC CCA ACA AGA GGA AGT GAA TTC TCT GGA AAG GGT GAT GTT CCC    1488
Arg Ser Pro Thr Arg Gly Ser Glu Phe Ser Gly Lys Gly Asp Val Pro
                485                 490                 495

AAT ACA TCT TTA AAT TCC ACT TCC CAA CCA GTC ACT AAA TTA GCC ACA    1536
Asn Thr Ser Leu Asn Ser Thr Ser Gln Pro Val Thr Lys Leu Ala Thr
            500                 505                 510

GAA AAA GAT ATT TCC TTG ACT TCT CAG ACT GTG ACT GAA CTG CCA CCT    1584
Glu Lys Asp Ile Ser Leu Thr Ser Gln Thr Val Thr Glu Leu Pro Pro
        515                 520                 525

CAC ACT GTG GAA GGT ACT TCA GCC TCT TTA AAT GAT GGC TCT AAA ACT    1632
His Thr Val Glu Gly Thr Ser Ala Ser Leu Asn Asp Gly Ser Lys Thr
    530                 535                 540

GTT CTT AGA TCT CCA CAT ATG AAC TTG TCG GGG ACT GCA GAA TCC TTA    1680
Val Leu Arg Ser Pro His Met Asn Leu Ser Gly Thr Ala Glu Ser Leu
545                 550                 555                 560

AAT ACA GTT TCT ATA ACA GAA TAT GAG GAG GAG AGT TTA TTG ACC AGT    1728
Asn Thr Val Ser Ile Thr Glu Tyr Glu Glu Glu Ser Leu Leu Thr Ser
                565                 570                 575

TTC AAG CTT GAT ACT GGA GCT GAA GAT TCT TCA GGC TCC AGT CCC GCA    1776
Phe Lys Leu Asp Thr Gly Ala Glu Asp Ser Ser Gly Ser Ser Pro Ala
            580                 585                 590

ACT TCT GCT ATC CCA TTC ATC TCT GAG AAC ATA TCC CAA GGG TAT ATA    1824
Thr Ser Ala Ile Pro Phe Ile Ser Glu Asn Ile Ser Gln Gly Tyr Ile
        595                 600                 605

TTT TCC TCC GAA AAC CCA GAG ACA ATA ACA TAT GAT GTC CTT ATA CCA    1872
Phe Ser Ser Glu Asn Pro Glu Thr Ile Thr Tyr Asp Val Leu Ile Pro
    610                 615                 620

GAA TCT GCT AGA AAT GCT TCC GAA GAT TCA ACT TCA TCA GGT TCA GAA    1920
Glu Ser Ala Arg Asn Ala Ser Glu Asp Ser Thr Ser Ser Gly Ser Glu
625                 630                 635                 640

GAA TCA CTA AAG GAT CCT TCT ATG GAG GGA AAT GTG TGG TTT CCT AGC    1968
Glu Ser Leu Lys Asp Pro Ser Met Glu Gly Asn Val Trp Phe Pro Ser
                645                 650                 655

TCT ACA GAC ATA ACA GCA CAG CCC GAT GTT GGA TCA GGC AGA GAG AGC    2016
Ser Thr Asp Ile Thr Ala Gln Pro Asp Val Gly Ser Gly Arg Glu Ser
            660                 665                 670

TTT CTC CAG ACT AAT TAC ACT GAG ATA CGT GTT GAT GAA TCT GAG AAG    2064
```

```
        Phe Leu Gln Thr Asn Tyr Thr Glu Ile Arg Val Asp Glu Ser Glu Lys
                    675                 680                 685

ACA ACC AAG TCC TTT TCT GCA GGC CCA GTG ATG TCA CAG GGT CCC TCA         2112
Thr Thr Lys Ser Phe Ser Ala Gly Pro Val Met Ser Gln Gly Pro Ser
        690                 695                 700

GTT ACA GAT CTG GAA ATG CCA CAT TAT TCT ACC TTT GCC TAC TTC CCA         2160
Val Thr Asp Leu Glu Met Pro His Tyr Ser Thr Phe Ala Tyr Phe Pro
705                 710                 715                 720

ACT GAG GTA ACA CCT CAT GCT TTT ACC CCA TCC TCC AGA CAA CAG GAT         2208
Thr Glu Val Thr Pro His Ala Phe Thr Pro Ser Ser Arg Gln Gln Asp
                725                 730                 735

TTG GTC TCC ACG GTC AAC GTG GTA TAC TCG CAG ACA ACC CAA CCG GTA         2256
Leu Val Ser Thr Val Asn Val Val Tyr Ser Gln Thr Thr Gln Pro Val
            740                 745                 750

TAC AAT GGT GAG ACA CCT CTT CAA CCT TCC TAC AGT AGT GAA GTC TTT         2304
Tyr Asn Gly Glu Thr Pro Leu Gln Pro Ser Tyr Ser Ser Glu Val Phe
                755                 760                 765

CCT CTA GTC ACC CCT TTG TTG CTT GAC AAT CAG ATC CTC AAC ACT ACC         2352
Pro Leu Val Thr Pro Leu Leu Leu Asp Asn Gln Ile Leu Asn Thr Thr
770                 775                 780

CCT GCT GCT TCA AGT AGT GAT TCG GCC TTG CAT GCT ACG CCT GTA TTT         2400
Pro Ala Ala Ser Ser Ser Asp Ser Ala Leu His Ala Thr Pro Val Phe
785                 790                 795                 800

CCC AGT GTC GAT GTG TCA TTT GAA TCC ATC CTG TCT TCC TAT GAT GGT         2448
Pro Ser Val Asp Val Ser Phe Glu Ser Ile Leu Ser Ser Tyr Asp Gly
                805                 810                 815

GCA CCT TTG CTT CCA TTT TCC TCT GCT TCC TTC AGT AGT GAA TTG TTT         2496
Ala Pro Leu Leu Pro Phe Ser Ser Ala Ser Phe Ser Ser Glu Leu Phe
                820                 825                 830

CGC CAT CTG CAT ACA GTT TCT CAA ATC CTT CCA CAA GTT ACT TCA GCT         2544
Arg His Leu His Thr Val Ser Gln Ile Leu Pro Gln Val Thr Ser Ala
            835                 840                 845

ACC GAG AGT GAT AAG GTG CCC TTG CAT GCT TCT CTG CCA GTG GCT GGG         2592
Thr Glu Ser Asp Lys Val Pro Leu His Ala Ser Leu Pro Val Ala Gly
        850                 855                 860

GGT GAT TTG CTA TTA GAG CCC AGC CTT GCT CAG TAT TCT GAT GTG CTG         2640
Gly Asp Leu Leu Leu Glu Pro Ser Leu Ala Gln Tyr Ser Asp Val Leu
865                 870                 875                 880

TCC ACT ACT CAT GCT GCT TCA AAG ACG CTG GAA TTT GGT AGT GAA TCT         2688
Ser Thr Thr His Ala Ala Ser Lys Thr Leu Glu Phe Gly Ser Glu Ser
                885                 890                 895

GGT GTT CTT TAT AAA ACG CTT ATG TTT TCT CAA GTT GAA CCA CCC AGC         2736
Gly Val Leu Tyr Lys Thr Leu Met Phe Ser Gln Val Glu Pro Pro Ser
            900                 905                 910

AGT GAT GCC ATG ATG CAT GCA CGT TCT TCA GGG CCT GAA CCT TCT TAT         2784
Ser Asp Ala Met Met His Ala Arg Ser Ser Gly Pro Glu Pro Ser Tyr
        915                 920                 925

GCC TTG TCT GAT AAT GAG GGC TCC CAA CAC ATC TTC ACT GTT TCT TAC         2832
Ala Leu Ser Asp Asn Glu Gly Ser Gln His Ile Phe Thr Val Ser Tyr
930                 935                 940

AGT TCT GCA ATA CCT GTG CAT GAT TCT GTG GGT GTA ACT TAT CAG GGT         2880
Ser Ser Ala Ile Pro Val His Asp Ser Val Gly Val Thr Tyr Gln Gly
945                 950                 955                 960

TCC TTA TTT AGC GGC CCT AGC CAT ATA CCA ATA CCT AAG TCT TCG TTA         2928
Ser Leu Phe Ser Gly Pro Ser His Ile Pro Ile Pro Lys Ser Ser Leu
                965                 970                 975

ATA ACC CCA ACT GCA TCA TTA CTG CAG CCT ACT CAT GCC CTC TCT GGT         2976
Ile Thr Pro Thr Ala Ser Leu Leu Gln Pro Thr His Ala Leu Ser Gly
            980                 985                 990

GAT GGG GAA TGG TCT GGA GCC TCT TCT GAT AGT GAA TTT CTT TTA CCT         3024
```

```
Asp Gly Glu Trp Ser Gly Ala Ser Ser Asp Ser Glu Phe Leu Leu Pro
         995                 1000                1005

GAC ACA GAT GGG CTG ACA GCC CTT AAC ATT TCT TCA CCT GTT TCT GTA      3072
Asp Thr Asp Gly Leu Thr Ala Leu Asn Ile Ser Ser Pro Val Ser Val
1010                1015                1020

GCT GAA TTT ACA TAT ACA ACA TCT GTG TTT GGT GAT GAT AAT AAG GCG      3120
Ala Glu Phe Thr Tyr Thr Thr Ser Val Phe Gly Asp Asp Asn Lys Ala
1025                1030                1035                1040

CTT TCT AAA AGT GAA ATA ATA TAT GGA AAT GAG ACT GAA CTG CAA ATT      3168
Leu Ser Lys Ser Glu Ile Ile Tyr Gly Asn Glu Thr Glu Leu Gln Ile
                1045                1050                1055

CCT TCT TTC AAT GAG ATG GTT TAC CCT TCT GAA AGC ACA GTC ATG CCC      3216
Pro Ser Phe Asn Glu Met Val Tyr Pro Ser Glu Ser Thr Val Met Pro
                1060                1065                1070

AAC ATG TAT GAT AAT GTA AAT AAG TTG AAT GCG TCT TTA CAA GAA ACC      3264
Asn Met Tyr Asp Asn Val Asn Lys Leu Asn Ala Ser Leu Gln Glu Thr
                1075                1080                1085

TCT GTT TCC ATT TCT AGC ACC AAG GGC ATG TTT CCA GGG TCC CTT GCT      3312
Ser Val Ser Ile Ser Ser Thr Lys Gly Met Phe Pro Gly Ser Leu Ala
1090                1095                1100

CAT ACC ACC ACT AAG GTT TTT GAT CAT GAG ATT AGT CAA GTT CCA GAA      3360
His Thr Thr Thr Lys Val Phe Asp His Glu Ile Ser Gln Val Pro Glu
1105                1110                1115                1120

AAT AAC TTT TCA GTT CAA CCT ACA CAT ACT GTC TCT CAA GCA TCT GGT      3408
Asn Asn Phe Ser Val Gln Pro Thr His Thr Val Ser Gln Ala Ser Gly
                1125                1130                1135

GAC ACT TCG CTT AAA CCT GTG CTT AGT GCA AAC TCA GAG CCA GCA TCC      3456
Asp Thr Ser Leu Lys Pro Val Leu Ser Ala Asn Ser Glu Pro Ala Ser
                1140                1145                1150

TCT GAC CCT GCT TCT AGT GAA ATG TTA TCT CCT TCA ACT CAG CTC TTA      3504
Ser Asp Pro Ala Ser Ser Glu Met Leu Ser Pro Ser Thr Gln Leu Leu
                1155                1160                1165

TTT TAT GAG ACC TCA GCT TCT TTT AGT ACT GAA GTA TTG CTA CAA CCT      3552
Phe Tyr Glu Thr Ser Ala Ser Phe Ser Thr Glu Val Leu Leu Gln Pro
        1170                1175                1180

TCC TTT CAG GCT TCT GAT GTT GAC ACC TTG CTT AAA ACT GTT CTT CCA      3600
Ser Phe Gln Ala Ser Asp Val Asp Thr Leu Leu Lys Thr Val Leu Pro
1185                1190                1195                1200

GCT GTG CCC AGT GAT CCA ATA TTG GTT GAA ACC CCC AAA GTT GAT AAA      3648
Ala Val Pro Ser Asp Pro Ile Leu Val Glu Thr Pro Lys Val Asp Lys
                1205                1210                1215

ATT AGT TCT ACA ATG TTG CAT CTC ATT GTA TCA AAT TCT GCT TCA AGT      3696
Ile Ser Ser Thr Met Leu His Leu Ile Val Ser Asn Ser Ala Ser Ser
                1220                1225                1230

GAA AAC ATG CTG CAC TCT ACA TCT GTA CCA GTT TTT GAT GTG TCG CCT      3744
Glu Asn Met Leu His Ser Thr Ser Val Pro Val Phe Asp Val Ser Pro
                1235                1240                1245

ACT TCT CAT ATG CAC TCT GCT TCA CTT CAA GGT TTG ACC ATT TCC TAT      3792
Thr Ser His Met His Ser Ala Ser Leu Gln Gly Leu Thr Ile Ser Tyr
        1250                1255                1260

GCA AGT GAG AAA TAT GAA CCA GTT TTG TTA AAA AGT GAA AGT TCC CAC      3840
Ala Ser Glu Lys Tyr Glu Pro Val Leu Leu Lys Ser Glu Ser Ser His
1265                1270                1275                1280

CAA GTG GTA CCT TCT TTG TAC AGT AAT GAT GAG TTG TTC CAA ACG GCC      3888
Gln Val Val Pro Ser Leu Tyr Ser Asn Asp Glu Leu Phe Gln Thr Ala
                1285                1290                1295

AAT TTG GAG ATT AAC CAG GCC CAT CCC CCA AAA GGA AGG CAT GTA TTT      3936
Asn Leu Glu Ile Asn Gln Ala His Pro Pro Lys Gly Arg His Val Phe
                1300                1305                1310

GCT ACA CCT GTT TTA TCA ATT GAT GAA CCA TTA AAT ACA CTA ATA AAT      3984
```

```
                Ala Thr Pro Val Leu Ser Ile Asp Glu Pro Leu Asn Thr Leu Ile Asn
                    1315                1320                1325

AAG CTT ATA CAT TCC GAT GAA ATT TTA ACC TCC ACC AAA AGT TCT GTT               4032
Lys Leu Ile His Ser Asp Glu Ile Leu Thr Ser Thr Lys Ser Ser Val
        1330                1335                1340

ACT GGT AAG GTA TTT GCT GGT ATT CCA ACA GTT GCT TCT GAT ACA TTT               4080
Thr Gly Lys Val Phe Ala Gly Ile Pro Thr Val Ala Ser Asp Thr Phe
1345                1350                1355                1360

GTA TCT ACT GAT CAT TCT GTT CCT ATA GGA AAT GGG CAT GTT GCC ATT               4128
Val Ser Thr Asp His Ser Val Pro Ile Gly Asn Gly His Val Ala Ile
                1365                1370                1375

ACA GCT GTT TCT CCC CAC AGA GAT GGT TCT GTA ACC TCA ACA AAG TTG               4176
Thr Ala Val Ser Pro His Arg Asp Gly Ser Val Thr Ser Thr Lys Leu
        1380                1385                1390

CTG TTT CCT TCT AAG GCA ACT TCT GAG CTG AGT CAT AGT GCC AAA TCT               4224
Leu Phe Pro Ser Lys Ala Thr Ser Glu Leu Ser His Ser Ala Lys Ser
                1395                1400                1405

GAT GCC GGT TTA GTG GGT GGT GGT GAA GAT GGT GAC ACT GAT GAT GAT               4272
Asp Ala Gly Leu Val Gly Gly Gly Glu Asp Gly Asp Thr Asp Asp Asp
        1410                1415                1420

GGT GAT GAT GAT GAT GAT GAC AGA GGT AGT GAT GGC TTA TCC ATT CAT               4320
Gly Asp Asp Asp Asp Asp Asp Arg Gly Ser Asp Gly Leu Ser Ile His
1425                1430                1435                1440

AAG TGT ATG TCA TGC TCA TCC TAT AGA GAA TCA CAG GAA AAG GTA ATG               4368
Lys Cys Met Ser Cys Ser Ser Tyr Arg Glu Ser Gln Glu Lys Val Met
                1445                1450                1455

AAT GAT TCA GAC ACC CAC GAA AAC AGT CTT ATG GAT CAG AAT AAT CCA               4416
Asn Asp Ser Asp Thr His Glu Asn Ser Leu Met Asp Gln Asn Asn Pro
        1460                1465                1470

ATC TCA TAC TCA CTA TCT GAG AAT TCT GAA GAA GAT AAT AGA GTC ACA               4464
Ile Ser Tyr Ser Leu Ser Glu Asn Ser Glu Glu Asp Asn Arg Val Thr
                1475                1480                1485

AGT GTA TCC TCA GAC AGT CAA ACT GGT ATG GAC AGA AGT CCT GGT AAA               4512
Ser Val Ser Ser Asp Ser Gln Thr Gly Met Asp Arg Ser Pro Gly Lys
        1490                1495                1500

TCA CCA TCA GCA AAT GGG CTA TCC CAA AAG CAC AAT GAT GGA AAA GAG               4560
Ser Pro Ser Ala Asn Gly Leu Ser Gln Lys His Asn Asp Gly Lys Glu
1505                1510                1515                1520

GAA AAT GAC ATT CAG ACT GGT AGT GCT CTG CTT CCT CTC AGC CCT GAA               4608
Glu Asn Asp Ile Gln Thr Gly Ser Ala Leu Leu Pro Leu Ser Pro Glu
                1525                1530                1535

TCT AAA GCA TGG GCA GTT CTG ACA AGT GAT GAA GAA AGT GGA TCA GGG               4656
Ser Lys Ala Trp Ala Val Leu Thr Ser Asp Glu Glu Ser Gly Ser Gly
        1540                1545                1550

CAA GGT ACC TCA GAT AGC CTT AAT GAG AAT GAG ACT TCC ACA GAT TTC               4704
Gln Gly Thr Ser Asp Ser Leu Asn Glu Asn Glu Thr Ser Thr Asp Phe
                1555                1560                1565

AGT TTT GCA GAC ACT AAT GAA AAA GAT GCT GAT GGG ATC CTG GCA GCA               4752
Ser Phe Ala Asp Thr Asn Glu Lys Asp Ala Asp Gly Ile Leu Ala Ala
        1570                1575                1580

GGT GAC TCA GAA ATA ACT CCT GGA TTC CCA CAG TCC CCA ACA TCA TCT               4800
Gly Asp Ser Glu Ile Thr Pro Gly Phe Pro Gln Ser Pro Thr Ser Ser
1585                1590                1595                1600

GTT ACT AGC GAG AAC TCA GAA GTG TTC CAC GTT TCA GAG GCA GAG GCC               4848
Val Thr Ser Glu Asn Ser Glu Val Phe His Val Ser Glu Ala Glu Ala
                1605                1610                1615

AGT AAT AGT AGC CAT GAG TCT CGT ATT GGT CTA GCT GAG GGG TTG GAA               4896
Ser Asn Ser Ser His Glu Ser Arg Ile Gly Leu Ala Glu Gly Leu Glu
        1620                1625                1630

TCC GAG AAG AAG GCA GTT ATA CCC CTT GTG ATC GTG TCA GCC CTG ACT               4944
```

-continued

```
Ser Glu Lys Lys Ala Val Ile Pro Leu Val Ile Val Ser Ala Leu Thr
    1635                1640                1645

TTT ATC TGT CTA GTG GTT CTT GTG GGT ATT CTC ATC TAC TGG AGG AAA        4992
Phe Ile Cys Leu Val Val Leu Val Gly Ile Leu Ile Tyr Trp Arg Lys
    1650                1655                1660

TGC TTC CAG ACT GCA CAC TTT TAC TTA GAG GAC AGT ACA TCC CCT AGA        5040
Cys Phe Gln Thr Ala His Phe Tyr Leu Glu Asp Ser Thr Ser Pro Arg
1665                1670                1675                1680

GTT ATA TCC ACA CCT CCA ACA CCT ATC TTT CCA ATT TCA GAT GAT GTC        5088
Val Ile Ser Thr Pro Pro Thr Pro Ile Phe Pro Ile Ser Asp Asp Val
            1685                1690                1695

GGA GCA ATT CCA ATA AAG CAC TTT CCA AAG CAT GTT GCA GAT TTA CAT        5136
Gly Ala Ile Pro Ile Lys His Phe Pro Lys His Val Ala Asp Leu His
        1700                1705                1710

GCA AGT AGT GGG TTT ACT GAA GAA TTT GAG GAA GTG CAG AGC TGT ACT        5184
Ala Ser Ser Gly Phe Thr Glu Glu Phe Glu Glu Val Gln Ser Cys Thr
    1715                1720                1725

GTT GAC TTA GGT ATT ACA GCA GAC AGC TCC AAC CAC CCA GAC AAC AAG        5232
Val Asp Leu Gly Ile Thr Ala Asp Ser Ser Asn His Pro Asp Asn Lys
1730                1735                1740

CAC AAG AAT CGA TAC ATA AAT ATC GTT GCC TAT GAT CAT AGC AGG GTT        5280
His Lys Asn Arg Tyr Ile Asn Ile Val Ala Tyr Asp His Ser Arg Val
1745                1750                1755                1760

AAG CTA GCA CAG CTT GCT GAA AAG GAT GGC AAA CTG ACT GAT TAT ATC        5328
Lys Leu Ala Gln Leu Ala Glu Lys Asp Gly Lys Leu Thr Asp Tyr Ile
            1765                1770                1775

AAT GCC AAT TAT GTT GAT GGC TAC AAC AGA CCA AAA GCT TAT ATT GCT        5376
Asn Ala Asn Tyr Val Asp Gly Tyr Asn Arg Pro Lys Ala Tyr Ile Ala
        1780                1785                1790

GCC CAA GGC CCA CTG AAA TCC ACA GCT GAA GAT TTC TGG AGA ATG ATA        5424
Ala Gln Gly Pro Leu Lys Ser Thr Ala Glu Asp Phe Trp Arg Met Ile
    1795                1800                1805

TGG GAA CAT AAT GTG GAA GTT ATT GTC ATG ATA ACA AAC CTC GTG GAG        5472
Trp Glu His Asn Val Glu Val Ile Val Met Ile Thr Asn Leu Val Glu
1810                1815                1820

AAA GGA AGG AGA AAA TGT GAT CAG TAC TGG CCT GCC GAT GGG AGT GAG        5520
Lys Gly Arg Arg Lys Cys Asp Gln Tyr Trp Pro Ala Asp Gly Ser Glu
1825                1830                1835                1840

GAG TAC GGG AAC TTT CTG GTC ACT CAG AAG AGT GTG CAA GTG CTT GCC        5568
Glu Tyr Gly Asn Phe Leu Val Thr Gln Lys Ser Val Gln Val Leu Ala
            1845                1850                1855

TAT TAT ACT GTG AGG AAT TTT ACT CTA AGA AAC ACA AAA ATA AAA AAG        5616
Tyr Tyr Thr Val Arg Asn Phe Thr Leu Arg Asn Thr Lys Ile Lys Lys
        1860                1865                1870

GGC TCC CAG AAA GGA AGA CCC AGT GGA CGT GTG GTC ACA CAG TAT CAC        5664
Gly Ser Gln Lys Gly Arg Pro Ser Gly Arg Val Val Thr Gln Tyr His
    1875                1880                1885

TAC ACG CAG TGG CCT GAC ATG GGA GTA CCA GAG TAC TCC CTG CCA GTG        5712
Tyr Thr Gln Trp Pro Asp Met Gly Val Pro Glu Tyr Ser Leu Pro Val
1890                1895                1900

CTG ACC TTT GTG AGA AAG GCA GCC TAT GCC AAG CGC CAT GCA GTG GGG        5760
Leu Thr Phe Val Arg Lys Ala Ala Tyr Ala Lys Arg His Ala Val Gly
1905                1910                1915                1920

CCT GTT GTC GTC CAC TGC AGT GCT GGA GTT GGA AGA ACA GGC ACA TAT        5808
Pro Val Val Val His Cys Ser Ala Gly Val Gly Arg Thr Gly Thr Tyr
            1925                1930                1935

ATT GTG CTA GAC AGT ATG TTG CAG CAG ATT CAA CAC GAA GGA ACT GTC        5856
Ile Val Leu Asp Ser Met Leu Gln Gln Ile Gln His Glu Gly Thr Val
        1940                1945                1950

AAC ATA TTT GGC TTC TTA AAA CAC ATC CGT TCA CAA AGA AAT TAT TTG        5904
```

```
Asn Ile Phe Gly Phe Leu Lys His Ile Arg Ser Gln Arg Asn Tyr Leu
    1955                1960                1965

GTA CAA ACT GAG GAG CAA TAT GTC TTC ATT CAT GAT ACA CTG GTT GAG        5952
Val Gln Thr Glu Glu Gln Tyr Val Phe Ile His Asp Thr Leu Val Glu
1970                1975                1980

GCC ATA CTT AGT AAA GAA ACT GAG GTG CTG GAC AGT CAT ATT CAT GCC        6000
Ala Ile Leu Ser Lys Glu Thr Glu Val Leu Asp Ser His Ile His Ala
1985                1990                1995                2000

TAT GTT AAT GCA CTC CTC ATT CCT GGA CCA GCA GGC AAA ACA AAG CTA        6048
Tyr Val Asn Ala Leu Leu Ile Pro Gly Pro Ala Gly Lys Thr Lys Leu
                2005                2010                2015

GAG AAA CAA TTC CAG CTC CTG AGC CAG TCA AAT ATA CAG CAG AGT GAC        6096
Glu Lys Gln Phe Gln Leu Leu Ser Gln Ser Asn Ile Gln Gln Ser Asp
        2020                2025                2030

TAT TCT GCA GCC CTA AAG CAA TGC AAC AGG GAA AAG AAT CGA ACT TCT        6144
Tyr Ser Ala Ala Leu Lys Gln Cys Asn Arg Glu Lys Asn Arg Thr Ser
            2035                2040                2045

TCT ATC ATC CCT GTG GAA AGA TCA AGG GTT GGC ATT TCA TCC CTG AGT        6192
Ser Ile Ile Pro Val Glu Arg Ser Arg Val Gly Ile Ser Ser Leu Ser
    2050                2055                2060

GGA GAA GGC ACA GAC TAC ATC AAT GCC TCC TAT ATC ATG GGC TAT TAC        6240
Gly Glu Gly Thr Asp Tyr Ile Asn Ala Ser Tyr Ile Met Gly Tyr Tyr
2065                2070                2075                2080

CAG AGC AAT GAA TTC ATC ATT ACC CAG CAC CCT CTC CTT CAT ACC ATC        6288
Gln Ser Asn Glu Phe Ile Ile Thr Gln His Pro Leu Leu His Thr Ile
                2085                2090                2095

AAG GAT TTC TGG AGG ATG ATA TGG GAC CAT AAT GCC CAA CTG GTG GTT        6336
Lys Asp Phe Trp Arg Met Ile Trp Asp His Asn Ala Gln Leu Val Val
        2100                2105                2110

ATG ATT CCT GAT GGC CAA AAC ATG GCA GAA GAT GAA TTT GTT TAC TGG        6384
Met Ile Pro Asp Gly Gln Asn Met Ala Glu Asp Glu Phe Val Tyr Trp
            2115                2120                2125

CCA AAT AAA GAT GAG CCT ATA AAT TGT GAG AGC TTT AAG GTC ACT CTT        6432
Pro Asn Lys Asp Glu Pro Ile Asn Cys Glu Ser Phe Lys Val Thr Leu
    2130                2135                2140

ATG GCT GAA GAA CAC AAA TGT CTA TCT AAT GAG GAA AAA CTT ATA ATT        6480
Met Ala Glu Glu His Lys Cys Leu Ser Asn Glu Glu Lys Leu Ile Ile
2145                2150                2155                2160

CAG GAC TTT ATC TTA GAA GCT ACA CAG GAT GAT TAT GTA CTT GAA GTG        6528
Gln Asp Phe Ile Leu Glu Ala Thr Gln Asp Asp Tyr Val Leu Glu Val
                2165                2170                2175

AGG CAC TTT CAG TGT CCT AAA TGG CCA AAT CCA GAT AGC CCC ATT AGT        6576
Arg His Phe Gln Cys Pro Lys Trp Pro Asn Pro Asp Ser Pro Ile Ser
        2180                2185                2190

AAA ACT TTT GAA CTT ATA AGT GTT ATA AAA GAA GAA GCT GCC AAT AGG        6624
Lys Thr Phe Glu Leu Ile Ser Val Ile Lys Glu Glu Ala Ala Asn Arg
            2195                2200                2205

GAT GGG CCT ATG ATT GTT CAT GAT GAG CAT GGA GGA GTG ACG GCA GGA        6672
Asp Gly Pro Met Ile Val His Asp Glu His Gly Gly Val Thr Ala Gly
    2210                2215                2220

ACT TTC TGT GCT CTG ACA ACC CTT ATG CAC CAA CTA GAA AAA GAA AAT        6720
Thr Phe Cys Ala Leu Thr Thr Leu Met His Gln Leu Glu Lys Glu Asn
2225                2230                2235                2240

TCC GTG GAT GTT TAC CAG GTA GCC AAG ATG ATC AAT CTG ATG AGG CCA        6768
Ser Val Asp Val Tyr Gln Val Ala Lys Met Ile Asn Leu Met Arg Pro
                2245                2250                2255

GGA GTC TTT GCT GAC ATT GAG CAG TAT CAG TTT CTC TAC AAA GTG ATC        6816
Gly Val Phe Ala Asp Ile Glu Gln Tyr Gln Phe Leu Tyr Lys Val Ile
        2260                2265                2270

CTC AGC CTT GTG AGC ACA AGG CAG GAA GAG AAT CCA TCC ACC TCT CTG        6864
```

-continued

```
Leu Ser Leu Val Ser Thr Arg Gln Glu Glu Asn Pro Ser Thr Ser Leu
    2275                2280                2285

GAC AGT AAT GGT GCA GCA TTG CCT GAT GGA AAT ATA GCT GAG AGC TTA      6912
Asp Ser Asn Gly Ala Ala Leu Pro Asp Gly Asn Ile Ala Glu Ser Leu
    2290                2295                2300

GAG TCT TTA GTT                                                       6924
Glu Ser Leu Val
2305
```

(2) INFORMATION FOR SEQ ID NO:3:

(i) SEQUENCE CHARACTERISTICS:
        (A) LENGTH: 267 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:3:

```
Gly Asp Pro Tyr Trp Ala Tyr Ser Gly Ala Tyr Gly Pro Glu His Trp
1               5                   10                  15

Val Thr Ser Ser Val Ser Cys Gly Gly Arg His Gln Ser Pro Ile Asp
                20                  25                  30

Ile Leu Asp Gln Tyr Ala Arg Val Gly Glu Glu Tyr Gln Glu Leu Gln
            35                  40                  45

Leu Asp Gly Phe Asp Asn Glu Ser Ser Asn Lys Thr Trp Met Lys Asn
        50                  55                  60

Thr Gly Lys Thr Val Ala Ile Leu Leu Lys Asp Asp Tyr Phe Val Ser
65                  70                  75                  80

Gly Ala Gly Leu Pro Gly Arg Phe Lys Ala Glu Lys Val Glu Phe His
                85                  90                  95

Trp Gly His Ser Asn Gly Ser Ala Gly Ser Glu His Ser Ile Asn Gly
                100                 105                 110

Arg Arg Phe Pro Val Glu Met Gln Ile Phe Phe Tyr Asn Pro Asp Asp
            115                 120                 125

Phe Asp Ser Phe Gln Thr Ala Ile Ser Glu Asn Arg Ile Ile Gly Ala
        130                 135                 140

Met Ala Ile Phe Phe Gln Val Ser Pro Arg Asp Asn Ser Ala Leu Asp
145                 150                 155                 160

Pro Ile Ile His Gly Leu Lys Gly Val His His Glu Lys Glu Thr
                165                 170                 175

Phe Leu Asp Pro Phe Val Leu Arg Asp Leu Leu Pro Ala Ser Leu Gly
            180                 185                 190

Ser Tyr Tyr Arg Tyr Thr Gly Ser Leu Thr Thr Pro Pro Cys Ser Glu
        195                 200                 205

Ile Val Glu Trp Ile Val Phe Arg Arg Pro Val Pro Ile Ser Tyr His
210                 215                 220

Gln Leu Glu Ala Phe Tyr Ser Ile Phe Thr Thr Glu Gln Gln Asp His
225                 230                 235                 240

Val Lys Ser Val Glu Tyr Leu Arg Asn Asn Phe Arg Pro Gln Gln Arg
                245                 250                 255

Leu His Asp Arg Val Val Ser Lys Ser Ala Val
                260                 265
```

(2) INFORMATION FOR SEQ ID NO:4:

(i) SEQUENCE CHARACTERISTICS:
        (A) LENGTH: 260 amino acids (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:4:

Ala Ser Pro Asp Trp Gly Tyr Asp Asp Lys Asn Gly Pro Glu Gln Trp
   1               5                   10                  15

Ser Lys Leu Tyr Pro Ile Ala Asn Gly Asn Asn Gln Ser Pro Val Asp
                   20                  25                  30

Ile Lys Thr Ser Glu Thr Lys His Asp Thr Ser Leu Lys Pro Ile Ser
                   35                  40                  45

Val Ser Tyr Asn Pro Ala Thr Ala Lys Glu Ile Ile Asn Val Gly His
   50                      55                  60

Ser Phe His Val Asn Phe Glu Asp Asn Asp Asn Arg Ser Val Leu Lys
   65                  70                  75                  80

Gly Gly Pro Phe Ser Asp Ser Tyr Arg Leu Phe Gln Phe His Phe His
                       85                  90                  95

Trp Gly Ser Thr Asn Glu His Gly Ser Glu His Thr Val Asp Gly Val
                   100                 105                 110

Lys Tyr Ser Ala Glu Leu His Val Ala His Trp Asn Ser Ala Lys Tyr
                   115                 120                 125

Ser Ser Leu Ala Glu Ala Ala Ser Lys Ala Asp Gly Leu Ala Val Ile
           130                 135                 140

Gly Val Leu Met Lys Val Gly Glu Ala Asn Pro Lys Leu Gln Lys Val
   145                 150                 155                 160

Leu Asp Ala Leu Gln Ala Ile Lys Thr Lys Gly Lys Arg Ala Pro Phe
                       165                 170                 175

Thr Asn Phe Asp Pro Ser Thr Leu Leu Pro Ser Ser Leu Asp Phe Trp
                   180                 185                 190

Thr Tyr Pro Gly Ser Leu Thr His Pro Pro Leu Tyr Glu Ser Val Thr
                   195                 200                 205

Trp Ile Ile Cys Lys Glu Ser Ile Ser Val Ser Ser Glu Gln Leu Ala
                   210                 215                 220

Gln Phe Arg Ser Leu Leu Ser Asn Val Glu Gly Asp Asn Ala Val Pro
   225                 230                 235                 240

Met Gln His Asn Asn Arg Pro Thr Gln Pro Leu Lys Gly Arg Thr Val
                       245                 250                 255

Arg Ala Ser Phe
                260

(2) INFORMATION FOR SEQ ID NO:5:

(i) SEQUENCE CHARACTERISTICS:
        (A) LENGTH: 259 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:5:

Ser His His Trp Gly Tyr Gly Lys His Asn Gly Pro Glu His Trp His
   1               5                   10                  15

Lys Asp Phe Pro Ile Ala Lys Gly Glu Arg Gln Ser Pro Val Asp Ile
                   20                  25                  30

Asp Thr His Thr Ala Lys Tyr Asp Pro Ser Leu Lys Pro Leu Ser Val
                   35                  40                  45

```
    Ser Tyr Asp Gln Ala Thr Ser Leu Arg Ile Leu Asn Asn Gly His Ala
        50                  55                  60

Phe Asn Val Glu Phe Asp Asp Ser Gln Asp Lys Ala Val Leu Lys Gly
     65                  70                  75                  80

Gly Pro Leu Asp Gly Thr Tyr Arg Leu Ile Gln Phe His Phe His Trp
                         85                  90                  95

Gly Ser Leu Asp Gly Gln Gly Ser Glu His Thr Val Asp Lys Lys Lys
                    100                 105                 110

Tyr Ala Ala Glu Leu His Leu Val His Trp Asn Thr Lys Tyr Gly Asp
                115                 120                 125

Phe Gly Lys Ala Val Gln Gln Pro Asp Gly Leu Ala Val Leu Gly Ile
    130                 135                 140

Phe Leu Lys Val Gly Ser Ala Lys Pro Gly Leu Gln Lys Val Val Asp
    145                 150                 155                 160

Val Leu Asp Ser Ile Lys Thr Lys Gly Lys Ser Ala Asp Phe Thr Asn
                    165                 170                 175

Phe Asp Pro Arg Gly Leu Leu Pro Glu Ser Leu Asp Tyr Trp Thr Tyr
                180                 185                 190

Pro Gly Ser Leu Thr Thr Pro Pro Leu Leu Glu Cys Val Thr Trp Ile
                195                 200                 205

Val Leu Lys Glu Pro Ile Ser Val Ser Ser Glu Gln Val Leu Lys Phe
                210                 215                 220

Arg Lys Leu Asn Phe Asn Gly Glu Gly Glu Pro Glu Glu Leu Met Val
    225                 230                 235                 240

Asp Asn Trp Arg Pro Ala Gln Pro Leu Lys Asn Arg Gln Ile Lys Ala
                    245                 250                 255

Ser Phe Lys (2) INFORMATION FOR SEQ ID NO:6:

(i) SEQUENCE CHARACTERISTICS:
        (A) LENGTH: 259 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:6:

Ala Lys Glu Trp Gly Tyr Ala Ser His Asn Gly Pro Asp His Trp His
     1               5                  10                  15

Glu Leu Phe Pro Asn Ala Lys Gly Glu Asn Gln Ser Pro Ile Glu Leu
                     20                  25                  30

His Thr Lys Asp Ile Arg His Asp Pro Ser Leu Gln Pro Trp Ser Val
                 35                  40                  45

Ser Tyr Asp Gly Gly Ser Ala Lys Thr Ile Leu Asn Asn Gly Lys Thr
         50                  55                  60

Cys Arg Val Val Phe Asp Asp Thr Tyr Asp Arg Ser Met Leu Arg Gly
     65                  70                  75                  80

Gly Pro Leu Pro Gly Pro Tyr Arg Leu Arg Gln Phe His Leu His Trp
                     85                  90                  95

Gly Ser Ser Asp Asp His Gly Ser Glu His Thr Val Asp Gly Val Lys
                    100                 105                 110

Tyr Ala Ala Glu Leu His Leu Val His Trp Asn Pro Lys Tyr Asn Thr
                115                 120                 125

Phe Lys Glu Ala Leu Lys Gln Arg Asp Gly Ile Ala Val Ile Gly Ile
```

```
                130                  135                   140
    Phe Leu Lys Ile Gly His Glu Asn Gly Glu Phe Gln Ile Phe Leu Asp
    145                 150                 155                 160

Ala Leu Asp Lys Ile Lys Thr Lys Gly Lys Glu Ala Pro Phe Thr Lys
                    165                 170                 175

Phe Asp Pro Ser Cys Leu Phe Pro Ala Cys Arg Asp Tyr Trp Thr Tyr
                180                 185                 190

Gln Gly Ser Phe Thr Thr Pro Pro Cys Glu Glu Cys Ile Val Trp Leu
                195                 200                 205

Leu Leu Lys Glu Pro Met Thr Val Ser Ser Asp Gln Met Ala Lys Leu
    210                 215                 220

Arg Ser Leu Leu Ser Ser Ala Glu Asn Glu Pro Pro Val Pro Leu Val
    225                 230                 235                 240

Ser Asn Trp Arg Pro Pro Gln Pro Ile Asn Asn Arg Val Val Arg Ala
                    245                 250                 255

Ser Phe Lys
```

(2) INFORMATION FOR SEQ ID NO:7:

(i) SEQUENCE CHARACTERISTICS:
        (A) LENGTH: 268 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:7:

```
    Ala Glu Ser His Trp Cys Tyr Glu Val Gln Ala Glu Ser Ser Asn Tyr
    1               5                   10                  15

Pro Cys Leu Val Pro Val Lys Trp Gly Gly Asn Cys Gln Lys Asp Arg
                    20                  25                  30

Gln Ser Pro Ile Asn Ile Val Thr Thr Lys Ala Lys Val Asp Lys Lys
                35                  40                  45

Leu Gly Arg Phe Phe Phe Ser Gly Tyr Asp Lys Lys Gln Thr Trp Thr
    50                  55                  60

Val Gln Asn Asn Gly His Ser Val Met Met Leu Leu Glu Asn Lys Ala
    65                  70                  75                  80

Ser Ile Ser Gly Gly Gly Leu Pro Ala Pro Tyr Gln Ala Lys Gln Leu
                    85                  90                  95

His Leu His Trp Ser Asp Leu Pro Tyr Lys Gly Ser Glu His Ser Leu
                    100                 105                 110

Asp Gly Glu His Phe Ala Met Glu Met His Ile Val His Glu Lys Glu
                115                 120                 125

Lys Gly Thr Ser Arg Asn Val Lys Glu Ala Gln Asp Pro Glu Asp Glu
    130                 135                 140

Ile Ala Val Leu Ala Phe Leu Val Glu Ala Gly Thr Gln Val Asn Glu
    145                 150                 155                 160

Gly Phe Gln Pro Leu Val Glu Ala Leu Ser Asn Ile Pro Lys Pro Glu
                    165                 170                 175

Met Ser Thr Thr Met Ala Glu Ser Ser Leu Leu Asp Leu Leu Pro Lys
                180                 185                 190

Glu Glu Lys Leu Arg His Tyr Phe Arg Tyr Leu Gly Ser Leu Thr Thr
                195                 200                 205

Pro Thr Cys Asp Glu Lys Val Val Trp Thr Val Phe Arg Glu Pro Ile
    210                 215                 220
```

```
     Gln Leu His Arg Glu Gln Ile Leu Ala Phe Ser Gln Lys Leu Tyr Tyr
     225                 230                 235                 240

Asp Lys Glu Gln Thr Val Ser Met Lys Asp Asn Val Arg Pro Leu Gln
                     245                 250                 255

Gln Leu Gly Gln Arg Thr Val Ile Lys Ser Gly Ala
                 260                 265
```

(2) INFORMATION FOR SEQ ID NO:8:

(i) SEQUENCE CHARACTERISTICS:
        (A) LENGTH: 262 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:8:

```
     Gln His Val Ser Asp Trp Thr Tyr Ser Glu Gly Ala Leu Asp Glu Ala
     1               5                   10                  15

His Trp Pro Gln His Tyr Pro Ala Cys Gly Gly Gln Arg Gln Ser Pro
                     20                  25                  30

Ile Asn Leu Gln Arg Thr Lys Val Arg Tyr Asn Pro Ser Leu Lys Gly
                 35                  40                  45

Leu Asn Met Thr Gly Tyr Glu Thr Gln Ala Gly Glu Phe Pro Met Val
     50                  55                  60

Asn Asn Gly His Thr Val Gln Ile Gly Leu Pro Ser Thr Met Arg Met
     65                  70                  75                  80

Thr Val Ala Asp Gly Ile Val Tyr Ile Ala Gln Gln Met His Phe His
                     85                  90                  95

Trp Gly Gly Ala Ser Ser Glu Ile Ser Gly Ser Glu His Thr Val Asp
                     100                 105                 110

Gly Ile Arg His Val Ile Glu Ile His Ile Val His Tyr Asn Ser Lys
                 115                 120                 125

Tyr Lys Thr Tyr Asp Ile Ala Gln Asp Ala Pro Asp Gly Leu Ala Val
     130                 135                 140

Leu Ala Ala Phe Val Glu Val Lys Asn Tyr Pro Glu Asn Thr Tyr Tyr
     145                 150                 155                 160

Ser Asn Phe Ile Ser His Leu Ala Asn Ile Lys Tyr Pro Gly Gln Arg
                     165                 170                 175

Thr Thr Leu Thr Gly Leu Asp Val Gln Asp Met Leu Pro Arg Asn Leu
                     180                 185                 190

Gln His Tyr Tyr Thr Tyr His Gly Ser Leu Thr Thr Pro Pro Cys Thr
                 195                 200                 205

Glu Asn Val His Trp Phe Val Leu Ala Asp Phe Val Lys Leu Ser Arg
     210                 215                 220

Thr Gln Val Trp Lys Leu Glu Asn Ser Leu Leu Asp His Arg Asn Lys
     225                 230                 235                 240

Thr Ile His Asn Asp Tyr Arg Arg Thr Gln Pro Leu Asn His Arg Val
                     245                 250                 255

Val Glu Ser Asn Phe Pro
                     260
```

(2) INFORMATION FOR SEQ ID NO:9:

(i) SEQUENCE CHARACTERISTICS:
        (A) LENGTH: 261 amino acids
        (B) TYPE: amino acid
        (C) STRANDEDNESS: single -continued

```
        (D) TOPOLOGY: unknown (ii) MOLECULE TYPE: protein (xi) SEQUENCE DESCRIPTION: SEQ ID NO:9:

Gly His His Gly Trp Gly Tyr Gly Gln Asp Asp Gly Pro Ala Ser His
1               5                   10                  15

Trp His Lys Leu Tyr Pro Ile Ala Gln Gly Asp Arg Gln Ser Pro Ile
                20                  25                  30

Asn Ile Ile Ser Ser Gln Ala Val Tyr Ser Pro Ser Leu Gln Pro Leu
                35                  40                  45

Glu Leu Ser Tyr Glu Ala Cys Met Ser Leu Ser Ile Thr Asn Asn Gly
        50              55                  60

His Ser Val Gln Val Asp Phe Asn Asp Ser Asp Asp Arg Thr Val Val
65                  70                  75                  80

Thr Gly Gly Pro Leu Glu Gly Pro Tyr Arg Leu Lys Gln Phe His Phe
                    85                  90                  95

His Trp Gly Lys Lys His Asp Val Gly Ser Glu His Thr Val Asp Gly
                100                 105                 110

Lys Ser Phe Pro Ser Glu Leu His Leu Val His Trp Asn Ala Lys Lys
                115                 120                 125

Tyr Ser Thr Phe Gly Glu Ala Ala Ser Ala Pro Asp Gly Leu Ala Val
                130                 135                 140

Gly Val Phe Leu Glu Thr Gly Asp Glu His Pro Ser Met Asn Arg Leu
145                 150                 155                 160

Thr Asp Ala Leu Tyr Met Val Arg Phe Lys Gly Thr Lys Ala Gln Phe
                    165                 170                 175

Ser Cys Phe Asn Pro Lys Cys Leu Leu Pro Ala Ser Arg His Tyr Trp
                180                 185                 190

Thr Tyr Pro Gly Ser Leu Thr Thr Pro Pro Leu Ser Glu Ser Val Thr
                195                 200                 205

Trp Ile Val Leu Arg Glu Pro Ile Cys Ile Ser Glu Arg Gln Met Gly
210                 215                 220

Lys Phe Arg Ser Leu Leu Phe Thr Ser Glu Asp Asp Glu Arg Ile His
225                 230                 235                 240

Met Val Asn Asn Phe Arg Pro Pro Gln Pro Leu Lys Gly Arg Val Val
                245                 250                 255

Lys Ala Ser Phe Arg
                260
```